(12) United States Patent
Vestweber et al.

(10) Patent No.: US 8,852,756 B2
(45) Date of Patent: *Oct. 7, 2014

(54) MATERIALS FOR ORGANIC ELECTROLUMINESCENT DEVICES

(75) Inventors: Horst Vestweber, Gilserberg (DE); Holger Heil, Darmstadt (DE); Philipp Stoessel, Frankfurt am Main (DE); Arne Buesing, Frankfurt am Main (DE); Amir Hossain Parham, Frankfurt (DE); Rocco Fortte, Frankfurt (DE)

(73) Assignee: Merck Patent GmbH (DE)

( * ) Notice: Subject to any disclaimer, the term of this patent is extended or adjusted under 35 U.S.C. 154(b) by 1359 days.

This patent is subject to a terminal disclaimer.

(21) Appl. No.: 11/914,824

(22) PCT Filed: Apr. 21, 2006

(86) PCT No.: PCT/EP2006/003670
§ 371 (c)(1),
(2), (4) Date: Jan. 30, 2008

(87) PCT Pub. No.: WO2006/122630
PCT Pub. Date: Nov. 23, 2006

(65) Prior Publication Data
US 2008/0220285 A1 Sep. 11, 2008

(30) Foreign Application Priority Data
May 20, 2005 (DE) .......................... 10 2005 023 437

(51) Int. Cl.
| | | |
|---|---|---|
| H01L 51/54 | (2006.01) | |
| C09K 11/06 | (2006.01) | |
| C07F 9/6568 | (2006.01) | |
| C07D 321/10 | (2006.01) | |
| C07D 319/08 | (2006.01) | |
| C07D 307/91 | (2006.01) | |
| C07C 45/00 | (2006.01) | |
| C07D 491/04 | (2006.01) | |
| C07C 45/63 | (2006.01) | |
| H01L 51/50 | (2006.01) | |
| C07D 495/04 | (2006.01) | |
| C07C 13/62 | (2006.01) | |
| C07F 9/6571 | (2006.01) | |
| C07D 333/76 | (2006.01) | |
| C07D 311/96 | (2006.01) | |
| C09B 57/00 | (2006.01) | |
| C07C 205/06 | (2006.01) | |
| C07D 215/44 | (2006.01) | |
| C07D 333/50 | (2006.01) | |
| C07F 9/53 | (2006.01) | |
| C07C 49/813 | (2006.01) | |
| C07D 487/04 | (2006.01) | |
| C07D 311/78 | (2006.01) | |
| C07C 211/61 | (2006.01) | |
| C07C 17/263 | (2006.01) | |
| C07C 49/792 | (2006.01) | |
| C07C 17/12 | (2006.01) | |
| C07D 493/04 | (2006.01) | |
| C07C 49/697 | (2006.01) | |
| C07D 279/24 | (2006.01) | |
| C07D 209/88 | (2006.01) | |
| C07C 13/72 | (2006.01) | |
| H01L 51/00 | (2006.01) | |

(52) U.S. Cl.
CPC .......... *H01L 51/006* (2013.01); *C07C 2103/90* (2013.01); *C07F 9/65685* (2013.01); *H01L 51/0054* (2013.01); *C09K 2211/1096* (2013.01); *C07D 321/10* (2013.01); *C07D 319/08* (2013.01); *H01L 51/0072* (2013.01); *C07C 2103/54* (2013.01); *C07D 307/91* (2013.01); *C07C 45/00* (2013.01); *C09K 2211/1037* (2013.01); *C07D 491/04* (2013.01); *H01L 51/002* (2013.01); *C07C 45/63* (2013.01); *Y02E 10/549* (2013.01); *H01L 51/5052* (2013.01); *C07D 495/04* (2013.01); *C07C 13/62* (2013.01); *H01L 51/0085* (2013.01); *C09K 2211/1014* (2013.01); *C07F 9/657163* (2013.01); *C07D 333/76* (2013.01); *C09K 2211/1011* (2013.01); *C07D 311/96* (2013.01); *H01L 51/0058* (2013.01); *C09B 57/00* (2013.01); *C07C 205/06* (2013.01); *C09K 2211/1007* (2013.01); *C07D 215/44* (2013.01); *C07D 333/50* (2013.01); *C07F 9/5325* (2013.01); *C07C 49/813* (2013.01); *C07D 487/04* (2013.01); *C07F 9/5329* (2013.01); *H01L 51/0055* (2013.01); *C09K 2211/1033* (2013.01); *C07D 311/78* (2013.01); *C07C 211/61* (2013.01); *C07C 17/2632* (2013.01); *C07C 49/792* (2013.01); *C09K 2211/1029* (2013.01); *C07C 17/12* (2013.01); *C09K 11/06* (2013.01); *H01L 51/0061* (2013.01); *C07D 493/04* (2013.01); *H01L 51/5036* (2013.01); *C09K 2211/1044* (2013.01); *C07C 49/697* (2013.01); *C07D 279/24* (2013.01); *H01L 51/5092* (2013.01); *C07D 209/88* (2013.01); *C07C 13/72* (2013.01); *H01L 51/0081* (2013.01); *C09K 2211/185* (2013.01)
USPC ............. 428/690; 42/917; 313/504; 313/506; 252/301.16; 257/40; 257/102; 257/103; 546/264; 564/426

(58) Field of Classification Search
None
See application file for complete search history.

(56) References Cited

U.S. PATENT DOCUMENTS

| | | |
|---|---|---|
| 5,840,217 A | 11/1998 | Lupo et al. |
| 7,241,513 B2 | 7/2007 | Suzuki et al. |
| 2001/0046612 A1 | 11/2001 | Lee et al. |
| 2002/0132134 A1 | 9/2002 | Hu et al. |
| 2003/0008174 A1 | 1/2003 | Suzuki et al. |
| 2004/0131880 A1 | 7/2004 | Zheng et al. |
| 2006/0058494 A1* | 3/2006 | Busing et al. .................. 528/86 |
| 2006/0228898 A1 | 10/2006 | Wajda et al. |
| 2007/0134511 A1 | 6/2007 | Kawamura et al. |
| 2008/0145698 A1 | 6/2008 | Heil et al. |
| 2008/0193797 A1 | 8/2008 | Heil et al. |
| 2008/0303003 A1 | 12/2008 | Heil et al. |

| | | | |
|---|---|---|---|
| 2009/0066225 A1 | 3/2009 | Kimura et al. | |
| 2009/0261717 A1 | 10/2009 | Buesing et al. | |
| 2010/0013381 A1 | 1/2010 | Stoessel et al. | |
| 2011/0168990 A1 | 7/2011 | Tanaka et al. | |

FOREIGN PATENT DOCUMENTS

| | | | | |
|---|---|---|---|---|
| JP | 62-264056 | A | 11/1987 | |
| JP | 4358884 | A | 12/1992 | |
| JP | 07-278537 | A | 10/1995 | |
| JP | 10340785 | A | 12/1998 | |
| JP | H11-162642 | A * | 6/1999 | H05B 33/14 |
| JP | 11-224779 | A | 8/1999 | |
| JP | 2000026324 | | 1/2000 | |
| JP | 2000-327639 | A | 11/2000 | |
| JP | 2001-039933 | A | 2/2001 | |
| JP | 2001-131541 | A | 5/2001 | |
| JP | 2001-220380 | A | 8/2001 | |
| JP | 2002-154993 | A | 5/2002 | |
| JP | 2002319490 | A | 10/2002 | |
| JP | 2002-326965 | A | 11/2002 | |
| JP | 2002-329582 | A | 11/2002 | |
| JP | 2003-128651 | A | 5/2003 | |
| JP | 2003-229273 | A | 8/2003 | |
| JP | 2003-261471 | A | 9/2003 | |
| JP | 2003-261473 | A | 9/2003 | |
| JP | 2004-042485 | A | 2/2004 | |
| JP | 2004-043349 | A | 2/2004 | |
| JP | 2004-083481 | A | 3/2004 | |
| JP | 2005-082702 | A | 3/2005 | |
| JP | 2005089674 | A | 4/2005 | |
| JP | 2005-119994 | A | 5/2005 | |
| JP | 2006512395 | A | 4/2006 | |
| JP | 2007-119454 | A | 5/2007 | |
| JP | 2008504247 | A | 2/2008 | |
| JP | 2008-537848 | A | 9/2008 | |
| JP | 2009-505995 | A | 2/2009 | |
| JP | 2009518328 | A | 5/2009 | |
| JP | 2009203183 | A | 9/2009 | |
| JP | 2009542735 | A | 12/2009 | |
| JP | 2009544743 | A | 12/2009 | |
| KR | 20070110371 | A | 11/2007 | |
| WO | WO-01/55719 | A2 | 8/2001 | |
| WO | WO 2004/037887 | A2 * | 5/2004 | C08G 61/12 |
| WO | WO 2004/041901 | A1 * | 5/2004 | C08G 61/00 |
| WO | WO-2004/061047 | A2 | 7/2004 | |
| WO | WO-2006/062078 | A1 | 6/2006 | |
| WO | WO-2006/100896 | A1 | 9/2006 | |
| WO | WO-2007/077810 | A1 | 7/2007 | |

OTHER PUBLICATIONS

English machine translation of JP H11-162642 A, 1999.*
Xiao-Yu, et al., "Giant Extended-Conjugated Dendrimers Containing the 10,15-Dihydro-5H-diindeno[1,2-a;1',2'-c]fluorene Chromophore: Synthesis, NMR Behaviors, Optical Properties, and Electroluminescence," *J. Org. Chem.* (2004), vol. 69, pp. 6050-6058.
James F. Ambrose, et al., "Electrochemical and Spectroscopic Properties of Cation Raicals", Journal of Electrochemical Society, vol. 122, No. 7, pp. 876-894, 1975.
A. Balionyte et al., "Photoconductive, photoluminescent and glass-forming 6,6'-di(N-diphenylamino)-9,9'-dialkyl-3,3'-bicarbazoles", Journal of Photochemistry and Photobiology, A Chemistry, vol. 162, No. 1, pp. 187-191, 2004.
Barnett, E., et al., "Beiträge zur Kenntnis der Anthracen-Derivate", (1933), pp. 1876-1891.
Pathak, R., et al., "A concise synthesis of novel naptho[a] carbazoles and benzo[c] carbazoles", Tetrahedron, vol. 62, (2006), pp. 2820-2830.
Office Action from corresponding Canadian Application No. 2,608,765 dated Mar. 18, 2013.
Office Action from corresponding Korean Application No. 2007-7029742 dated Mar. 29, 2013.

* cited by examiner

*Primary Examiner* — Michael H Wilson
(74) *Attorney, Agent, or Firm* — Drinker Biddle & Reath LLP

(57) ABSTRACT

The present invention relates to the improvement of organic electroluminescent devices, in particular blue-emitting devices, by using compounds of the formula (1) as dopants in the emitting layer.

(1)

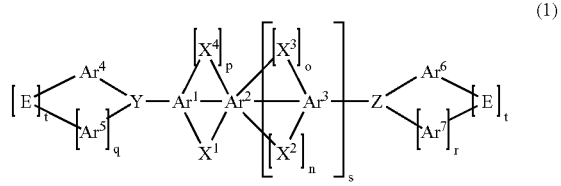

21 Claims, No Drawings

MATERIALS FOR ORGANIC ELECTROLUMINESCENT DEVICES

RELATED APPLICATIONS

This application is a national stage application (under 35 U.S.C. 371) of PCT/EP2006/003670 filed Apr. 21, 2006, which claims benefit of German application 10 2005 023 437.2 filed May 20, 2005.

The present invention describes novel compounds and the use thereof in organic electronic devices.

The general structure of organic electroluminescent devices is described, for example, in U.S. Pat. Nos. 4,539,507, 5,151,629, EP 0676461 and WO 98/27136. However, these devices still exhibit considerable problems which require urgent improvement:

1. The efficiency, especially in the case of fluorescent OLEDs, is still too low and must be improved.
2. The operating lifetime is still low, in particular in the case of blue emission, meaning that it has hitherto only been possible to achieve simple applications commercially.
3. The operating voltage is quite high, especially in the case of fluorescent OLEDs, and should therefore be further reduced in order to improve the power efficiency. This is of particularly great importance for mobile applications.
4. Many blue-emitting emitters which comprise both aromatic amines and also vinyl groups are thermally unstable and decompose on sublimation or on vapour deposition. The use of these systems is consequently only possible with great losses and with high technical complexity, if at all.
5. In hole-transport materials in accordance with the prior art, the voltage is dependent on the layer thickness of the transport layer. In practice, a greater layer thickness of the hole-transport layer would be desirable. However, this cannot be achieved with materials in accordance with the prior art owing to the associated increase in voltage.

As closest prior art, the use of certain arylvinylamines by Idemitsu (for example WO 04/013073, WO 04/016575, WO 04/018587) can be mentioned. Very good lifetimes with dark-blue emission are cited therewith. However, these results are highly dependent on the host material used, meaning that the lifetimes cited cannot be compared as absolute values, but instead always only on use in an optimised system. Furthermore, these compounds are thermally unstable and cannot be evaporated without decomposition, which therefore requires high technical complexity for the OLED production and thus represents a significant technical disadvantage. A further disadvantage is the emission colour of these compounds. While Idemitsu cites dark-blue emission (CIE y coordinates in the range 0.15-0.18), it has not been possible to reproduce these colour coordinates in simple devices in accordance with the prior art. On the contrary, green-blue emission is obtained here. It is not clear how blue emission can in fact be produced using these compounds.

There thus continues to be a demand for blue-emitting compounds which result in good efficiencies in organic electroluminescent devices and at the same time result in long lifetimes and can be processed without technical problems. Surprisingly, it has now been found that organic electroluminescent devices which comprise certain compounds—mentioned below—as blue-emitting dopants in a host material have significant improvements over the prior art. It is possible with these materials to obtain longer life-times at the same time as higher efficiency. In addition, these compounds can, in contrast to materials in accordance with the prior art, be sublimed without notable decomposition, even in relatively large amounts, and are therefore significantly easier to handle than materials in accordance with the prior art. The present invention therefore relates to these compounds and to the use thereof in OLEDs.

The invention relates to compounds of the formula (1)

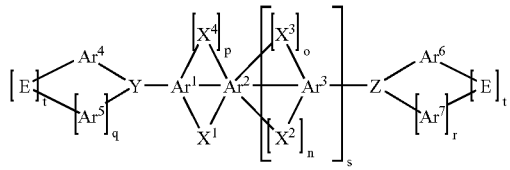

Formel (1)

where the following applies to the symbols and indices used:

Y, Z are, identically or differently, N, P, P=O, $PF_2$, P=S, As, As=O, As=S, Sb, Sb=O, Sb=S, Bi, Bi=O, Bi=S, C=O, O, S, Se, Te, S=O, $SO_2$, Se=O, $SeO_2$, Te=O or $TeO_2$;

$Ar^1$, $Ar^2$, $Ar^3$ are on each occurrence, identically or differently, an aryl or heteroaryl group having 5 to 24 aromatic ring atoms, which may be substituted by one or more radicals $R^1$;

$Ar^4$, $Ar^5$, $Ar^6$, $Ar^7$ are on each occurrence, identically or differently, an aromatic or heteroaromatic ring system having 5 to 40 aromatic ring atoms, which may be substituted by one or more radicals $R^1$;

E is on each occurrence, identically or differently, a single bond, $N(R^1)$, O, S, $C(R^1)_2$, $Si(R^1)_2$ or $B(R^1)$;

$R^1$ is on each occurrence, identically or differently, H, F, Cl, Br, I, CN, $NO_2$, $B(OR^2)_2$, $Si(R^2)_3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by —$R^2$C=$CR^2$—, —C≡C—, $Si(R^2)_2$, $Ge(R^2)_2$, $Sn(R^2)_2$, C=O, C=S, C=Se, C=$NR^2$, —O—, —S—, —COO— or —$CONR^2$— and where one or more H atoms may be replaced by F, Cl, Br, I, CN or $NO_2$, or an aromatic or heteroaromatic ring system having 5 to 40 aromatic ring atoms, which may be substituted by one or more non-aromatic radicals $R^1$, or an aryloxy or heteroaryloxy group having 5 to 40 aromatic ring atoms, which may be substituted by one or more non-aromatic radicals $R^1$, or a combination of these systems; two or more substituents $R^1$ here may also form a mono- or poly-cyclic ring system with one another;

$R^2$ is on each occurrence, identically or differently, H or an aliphatic or aromatic hydrocarbon radical having 1 to 20 C atoms;

$X^1$, $X^4$ are on each occurrence, identically or differently, a bridge which, with $Ar^1$ and $Ar^2$, defines a cyclic system selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$, P(=O)$R^1$, P(=S)$R^1$ or a combination of two, three or four of these groups;

$X^2$, $X^3$ are on each occurrence, identically or differently, a bridge which, with Ar2 and $Ar^3$, defines a cyclic ring system selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$, P(=O)$R^1$, P(=S)$R^1$ or a combination of two, three or four of these groups;

n, o, p are on each occurrence, identically or differently, 0 or 1, with the proviso that n, p and o may only simultaneously be 0 if $X^1$ is a group other than a $C(R^1)_2$ bridge where $R^1$=an open-chain alkyl radical; n=0 and o=0 and p=0 here mean that two H or $R^1$ radicals are present instead of the bridge;

q, r are on each occurrence 1 if the corresponding central atom of the group Y or Z is an element from the 5th main group and on each occurrence are equal to 0 if the corresponding central atom of the group Y or Z is an element from the 4th or 6th main group;

s is 1, 2 or 3;

t is on each occurrence, identically or differently, 0 or 1, where t=0 means that $R^1$ radicals are bonded instead of the group E; furthermore t=0 if q=0.

For the purposes of this invention, an aryl group or a heteroaryl group is taken to mean an aromatic group or heteroaromatic group respectively having a common aromatic electron system, where an aryl group contains 6 to 24 C atoms and a heteroaryl group contains 2 to 24 C atoms and a total of at least 5 aromatic ring atoms. The hetero atoms are preferably selected from N, O and/or S. For the purposes of this invention, this can be a single homo- or heterocyclic ring, for example benzene, pyridine, thiophene, etc., or it can be a fused aromatic ring system in which at least two aromatic or heteroaromatic rings, for example benzene rings, are fused to one another, i.e. have at least one common edge and thus also a common aromatic system. This aryl or heteroaryl group may be substituted or unsubstituted; any substituents present may likewise form further ring systems. Thus, for example, systems such as naphthalene, anthracene, phenanthrene, pyrene, etc., are to be regarded as aryl groups for the purposes of this invention and quinoline, acridine, benzothiophene, carbazole, etc., are to be regarded as heteroaryl groups for the purposes of this invention, while, for example, biphenyl, fluorene, spirobifluorene, etc., are not aryl groups since separate aromatic electron systems are present here.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is taken to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, a C, N or O atom. Thus, for example, systems such as 9,9'-spirobifluorene, 9,9-diarylfluorene, triarylamine, diaryl ether, etc., are also to be regarded as aromatic ring systems for the purposes of this invention.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{24}$-aryl or -heteroaryl group, which can be monovalent or divalent depending on the use, may also be substituted by the above-mentioned radicals $R^1$ and may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. For the purposes of this invention, aromatic and heteroaromatic ring systems are taken to mean, in particular, biphenylene, terphenylene, fluorene, spirobifluorene, dihydrophenanthrene, tetrahydropyrene and cis- or trans-indenofluorene, in addition to the above-mentioned aryl and heteroaryl groups.

Preference is given to compounds of the formula (1) in which the symbols Y and Z, identically or differently, stand for nitrogen, C=O, phosphorus or P=O, particularly preferably for nitrogen, C=O or P=O. Y and Z very particularly preferably stand for nitrogen.

Preference is furthermore given to compounds of the formula (1) in which the symbols $Ar^1$, $Ar^2$ and $Ar^3$, identically or differently on each occurrence, stand for an aryl or heteroaryl group having 5 to 16 aromatic ring atoms, which may be substituted by one or two radicals $R^1$, particularly preferably for an aryl or heteroaryl group selected from benzene, naphthalene, anthracene, phenanthrene, pyridine, pyrene and thiophene, in particular benzene, each of which may be substituted by one or two radicals $R^1$. The direct linking between Y, $Ar^1$, $Ar^2$, $Ar^3$ and Z particularly preferably takes place via the para-positions of the benzene (or the corresponding positions of the other aromatic compounds).

Particular preference is thus given to compounds of the formula (1a)

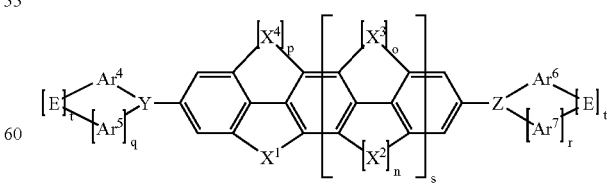

Formula (1a)

where the symbols and indices have the same meanings as described above.

Preference is furthermore given to compounds of the formulae (1) and (1a) in which the symbols $Ar^4$, $Ar^5$, $Ar^6$ and $Ar^7$, identically or differently on each occurrence, stand for an aromatic or heteroaromatic ring system having 5 to 16 aromatic ring atoms, for a triarylamine or for spirobifluorene, each of which may be substituted by one or more radicals $R^1$, particularly preferably for an aromatic or heteroaromatic ring system selected from benzene, naphthalene, anthracene, phenanthrene, pyridine, pyrene, thiophene, triphenylamine, diphenyl-1-naphthylamine, diphenyl-2-naphthylamine, phenyldi(1-naphthyl)amine, and phenyldi-(2-naphthyl)amine, each of which may be substituted by $R^1$. The symbols $Ar^4$, $Ar^5$, $Ar^6$ and $Ar^7$ very particularly preferably stand, identically or differently on each occurrence, for phenyl, 1-naphthyl or 2-naphthyl, each of which may be substituted by one or two radicals $R^1$.

Preference is furthermore given to compounds of the formulae (1) and (1a) in which the index t=0 or in which the index t=1 and the corresponding symbol E stands for a single bond, O, S or $N(R^1)$. Very particular preference is given to compounds of the formulae (1) and (1a) in which the index t=0 or in which the index t=1 and the corresponding symbol E stands for a single bond.

Preference is furthermore given to compounds of the formula (1) in which the symbol $R^1$, identically or differently on each occurrence, stands for H, F, CN, a straight-chain alkyl group having 1 to 5 C atoms or a branched alkyl group having 3 to 5 C atoms, where in each case one or more non-adjacent $CH_2$ groups may be replaced by $—R^2C=CR^2—$, $—C\equiv C—$, $—O—$ or $—S—$ and where one or more H atoms may be replaced by F, or a monovalent aryl or heteroaryl group having 5 to 16 aromatic ring atoms, which may be substituted by one or more non-aromatic radicals $R^1$, where two or more radicals $R^1$ may form a ring system with one another; $R^1$ particularly preferably stands for H, F, CN, methyl, tert-butyl or a monovalent aryl or heteroaryl group having 4 to 6 C atoms, which may be substituted by one or more non-aromatic radicals $R^1$, where two aromatic radicals $R^1$ may form a ring system with one another. $R^1$ very particularly preferably =H if it is bonded directly to one of the groups $Ar^1$ to $Ar^7$.

$R^1$ is preferably, if it is bonded to a group $X^1$, $X^2$, $X^3$ and/or $X^4$, is furthermore preferably a straight-chain alkyl group having 1 to 10 C atoms or a branched or cyclic alkyl group having 3 to 10 C atoms, where in each case one or more non-adjacent $CH_2$ groups may be replaced by $—R^2C=CR^2—$, $—C\equiv C—$, $—O—$, or $—S—$ and where one or more H atoms may be replaced by F, or a monovalent aryl or heteroaryl group having 5 to 16 aromatic ring atoms, which may be substituted by one or more non-aromatic radicals $R^1$; two radicals $R^1$ here may also form a ring system with one another.

Preference is furthermore given to compounds in which p=0 and one of the two indices n and o=1, while the other of the two indices=0; particularly preferably, p and n=0 and o=1.

Particular preference is therefore given to the structures of the formulae (1b) and (1c), in particular of the formula (1c), shown below

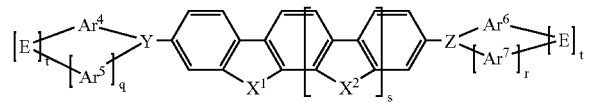

Formula (1b)

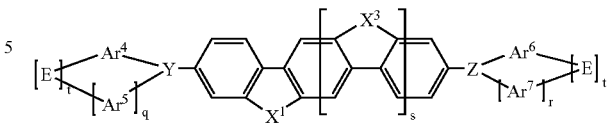

Formula (1c)

where the symbols and indices have the same meanings as described above.

Preference is furthermore given to compounds of the formulae (1) and (1a) to (1c) in which the symbols $X^1$, $X^2$, $X^3$ and $X^4$ on each occurrence, identically or differently, are a bridge which, with $Ar^1$ and $Ar^2$ or with $Ar^2$ and $Ar^3$, defines a cyclic system selected from $C(R^1)_2$, C=O, $C=NR^1$, O, S, S=O, $SO_2$, $N(R^1)$, $P(R^1)$, $P(=O)R^1$, $C(R^1)_2—C(R^1)_2$, $C(R^1)_2—C(R^1)_2—C(R^1)_2$, $C(R^1)_2—O$, $C(R^1)_2—O—C(R^1)_2$. Very particular preference is given to compounds of the formula (1) in which the symbols $X^1$, $X^2$, $X^3$ and $X^4$ on each occurrence, identically or differently, are selected from $C(R^1)_2$, $N(R^1)$, $P(R^1)$ and $P(=O)(R^1)$, very particularly preferably $C(R^1)_2$ and $N(R^1)$, in particular $C(R^1)_2$.

Very particular preference is therefore given to compounds of the formula (1d)

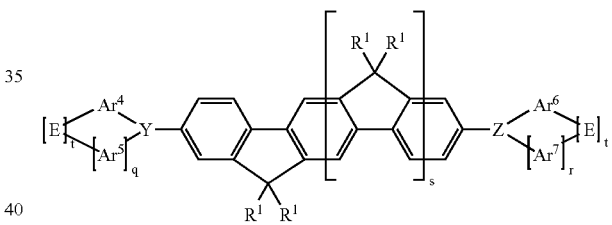

Formula (1d)

where the symbols and indices have the same meanings as described above.

In structures of the formula (1d), the symbols $R^1$ are preferably selected from straight-chain alkyl groups having 1 to 10 C atoms or branched or cyclic alkyl groups having 3 to 10 C atoms, where in each case one or more non-adjacent $CH_2$ groups may be replaced by $—R^2C=CR^2—$, $—C\equiv C—$, $—O—$ or $—S—$ and where one or more H atoms may be replaced by F, or monovalent aryl or heteroaryl groups having 5 to 16 aromatic ring atoms, which may be substituted by one or more non-aromatic radicals $R^1$; two radicals $R^1$ here may also form a ring system with one another. In the radicals $R^1$ are particularly preferably selected from straight-chain alkyl groups having 1 to 4 C atoms and branched alkyl groups having 3 or 4 C atoms, in particular methyl groups, and phenyl groups; two or more radicals $R^1$ here may form a ring system with one another.

If a plurality of radicals $R^1$ form a ring system with one another, a spiro structure is formed. This may be preferred, in particular, if the radicals $R^1$ stand for phenyl groups. This then gives rise to structures of the general formula (1e)

Formula (1e)

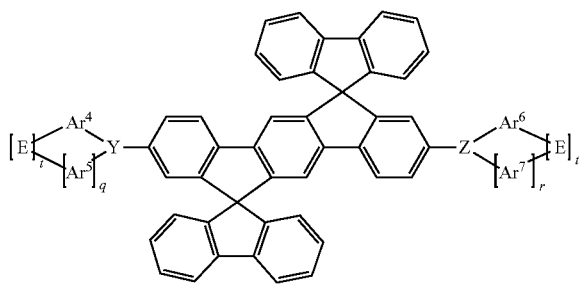

where the symbols and indices have the same meanings as described above and where the spiro systems may each be substituted by one or more non-aromatic radicals $R^1$.

Preference is furthermore given to compounds of the formulae (1) and (1a) to (1d) in which the symbol s=1 or s=2. Very particular preference is given to compounds where s=1.

Preference is furthermore given to compounds of the formulae (1) and (1a) to (1e) in which Y=Z. Very particular preference is given to compounds in which, in addition, $Ar^4=Ar^6$ and, if present, $Ar^5=Ar^7$ and, if present, both groups E are selected identically.

Examples of preferred compounds of the formula (1) are structures (1) to (104) shown below.

(1)

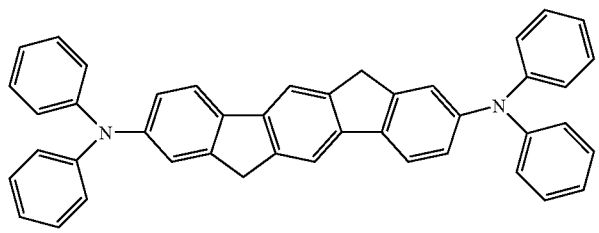

(2)

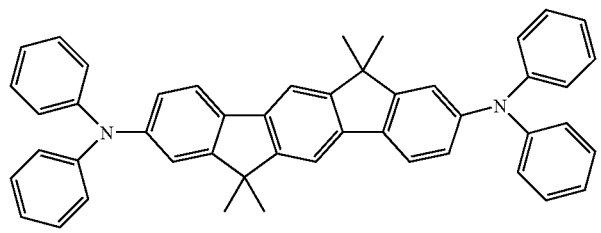

(3)

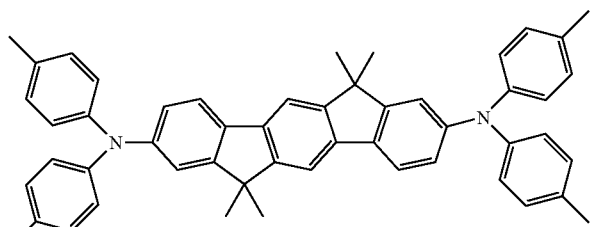

(4)

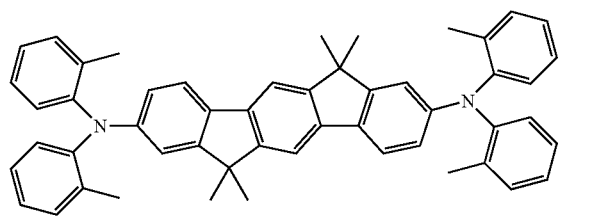

(5)

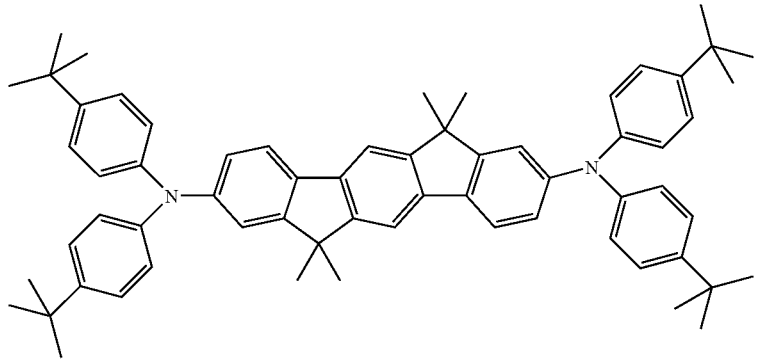

(6)

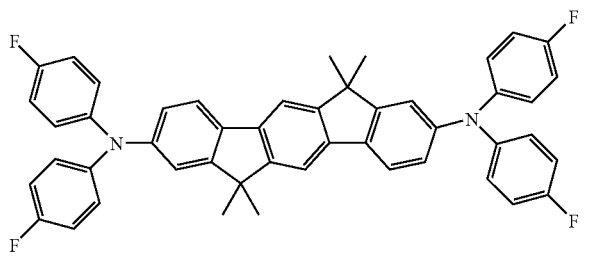

(7)

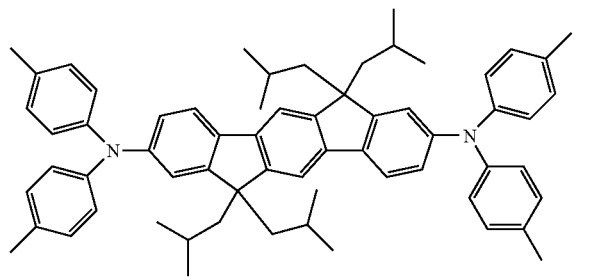

-continued
(8)
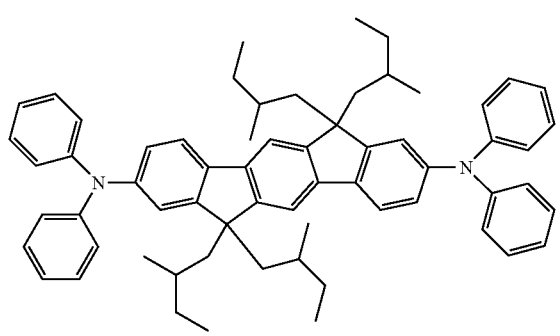
(9)
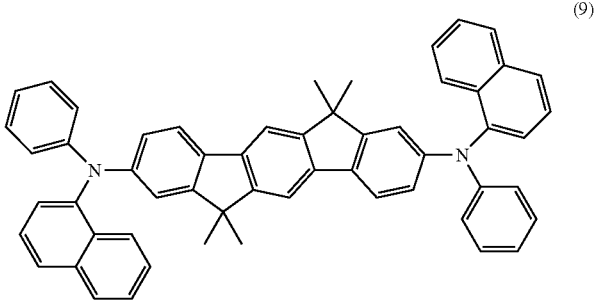
(10)
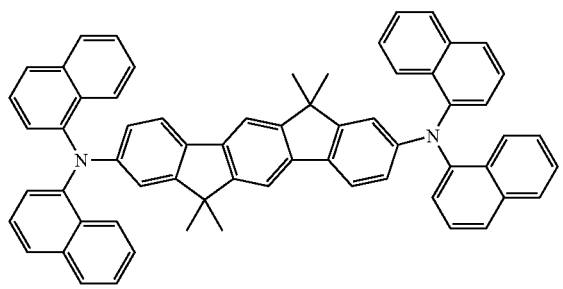
(11)
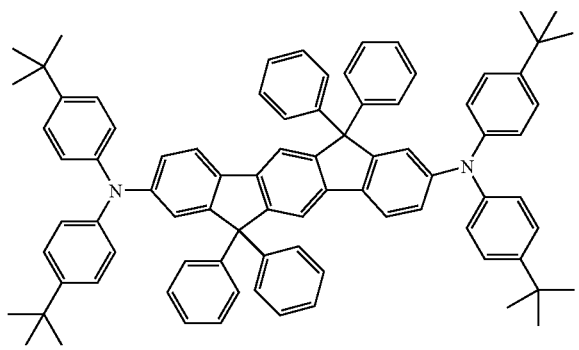
(12)
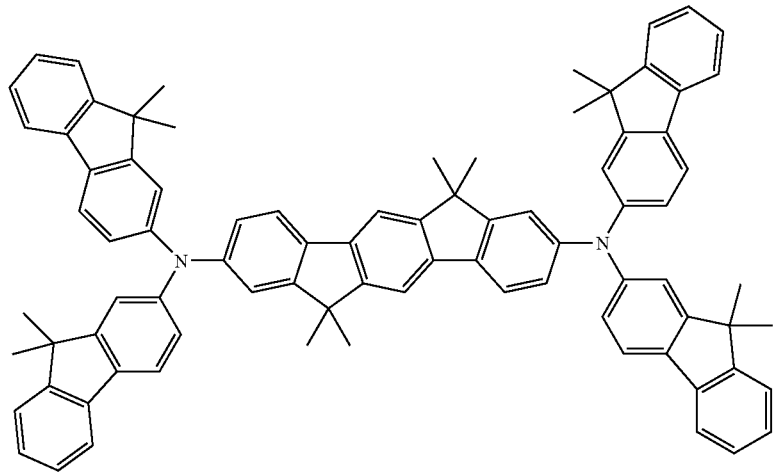
(13)
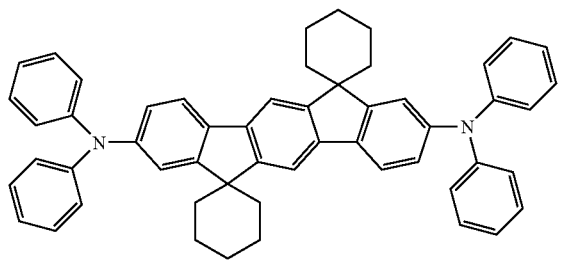
(14)
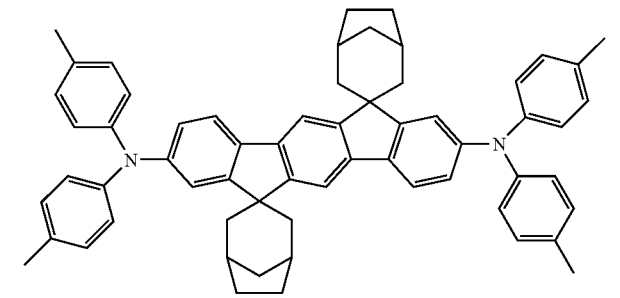

-continued
(15)
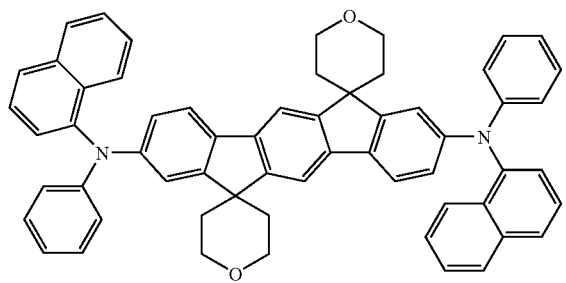
(16)
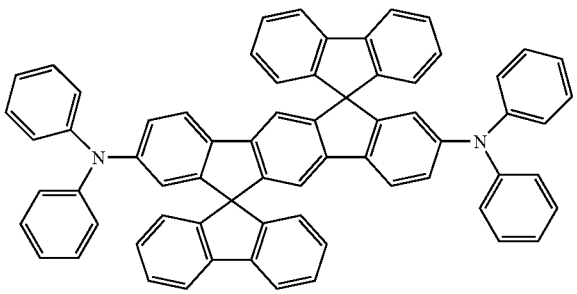
(17)
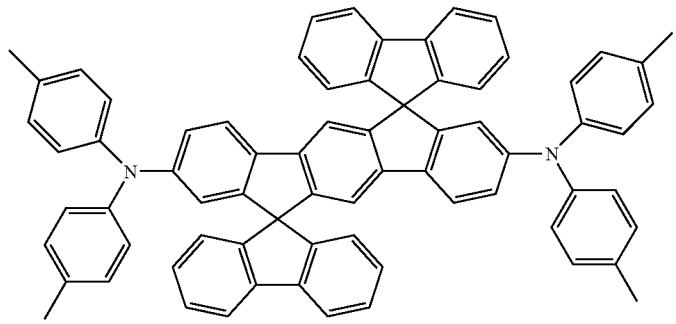
(18)
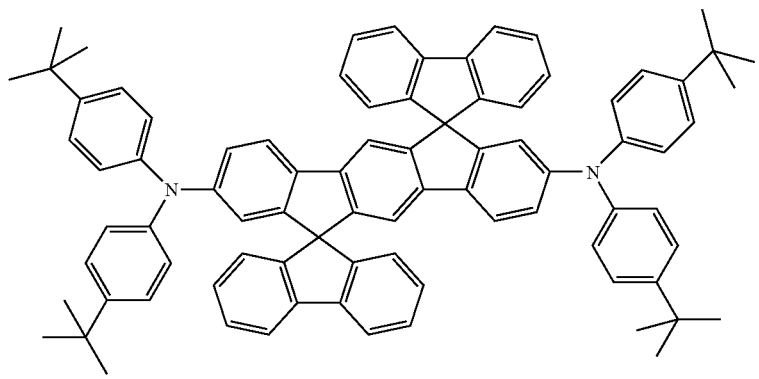
(19)
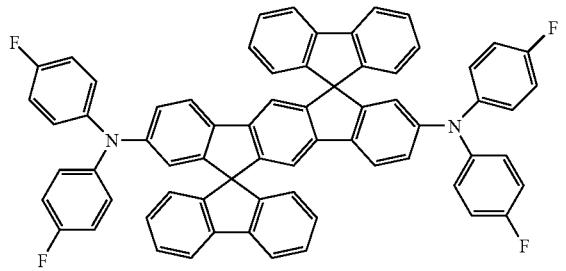
(20)
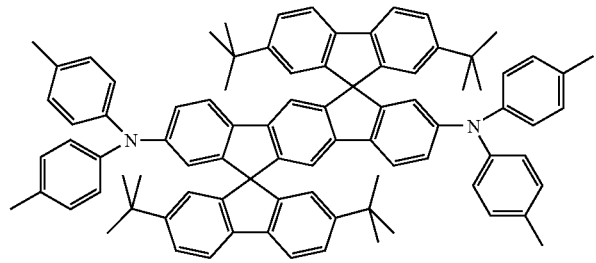
(21)
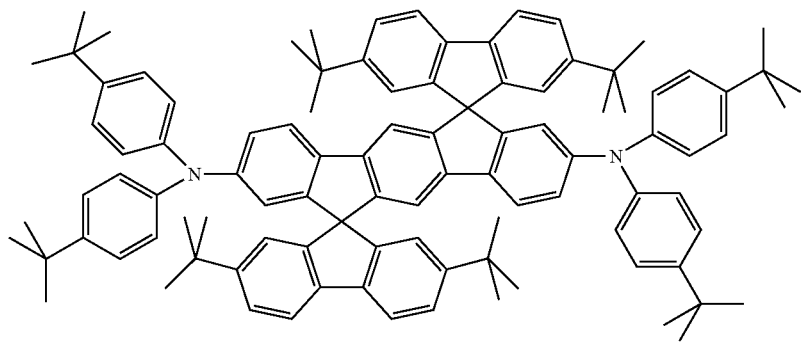

-continued
(22)
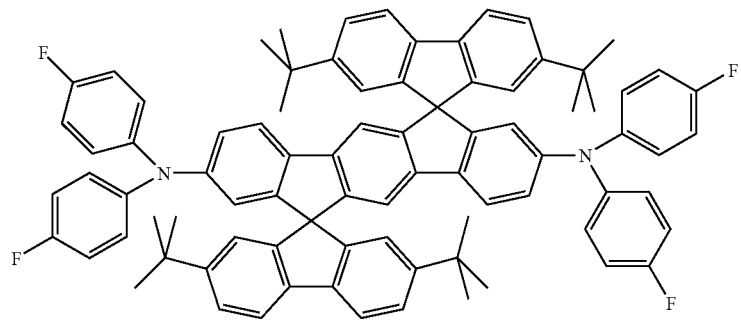
(23) (24)
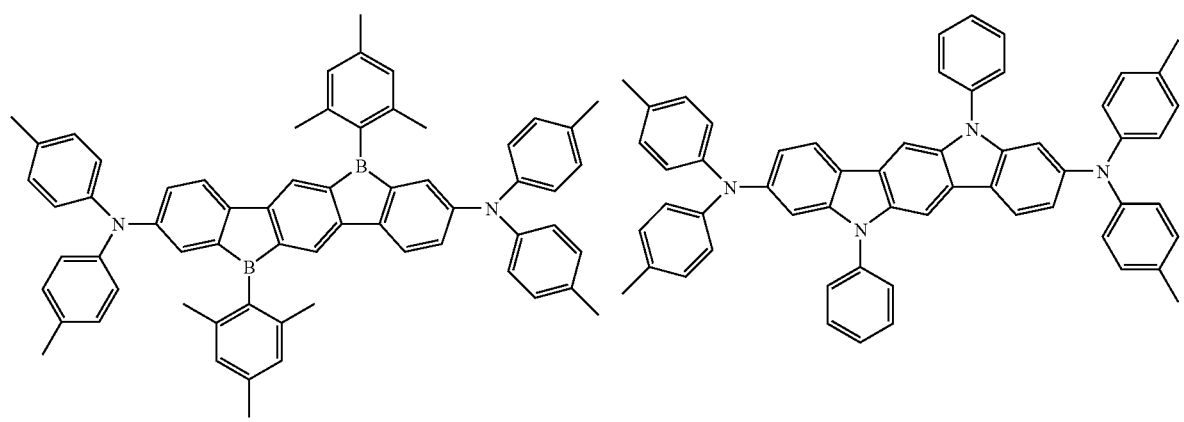
(25) (26)
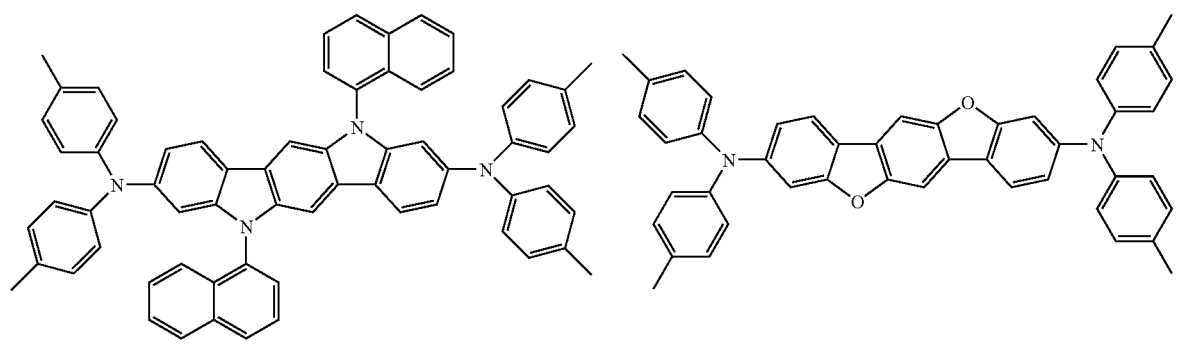
(27) (28)
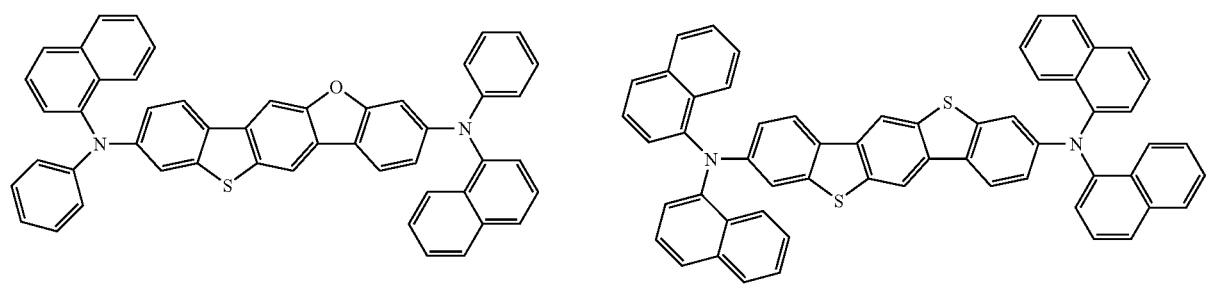

-continued
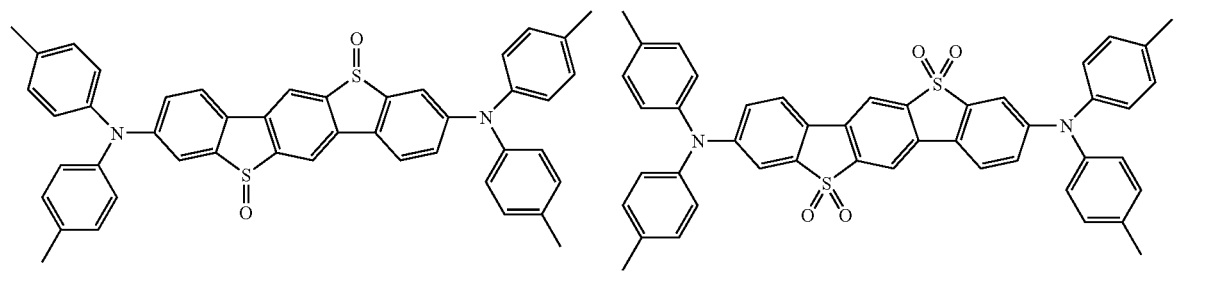
(29) (30)
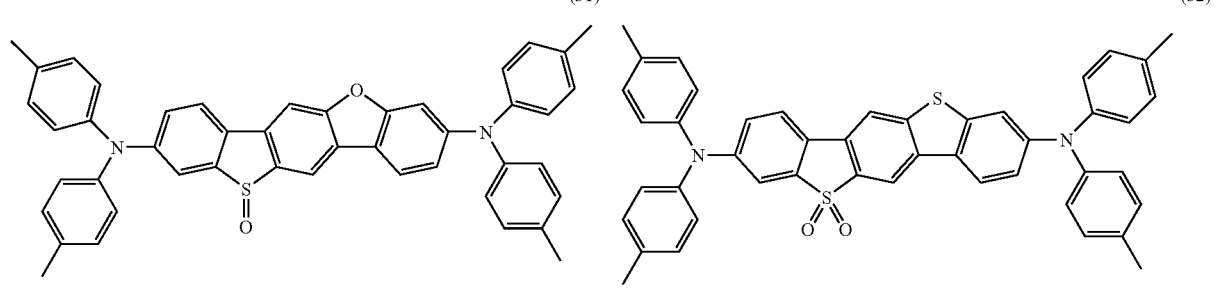
(31) (32)
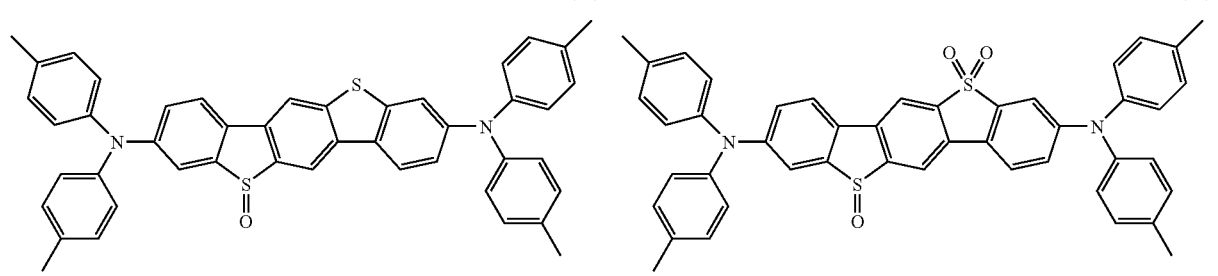
(33) (34)
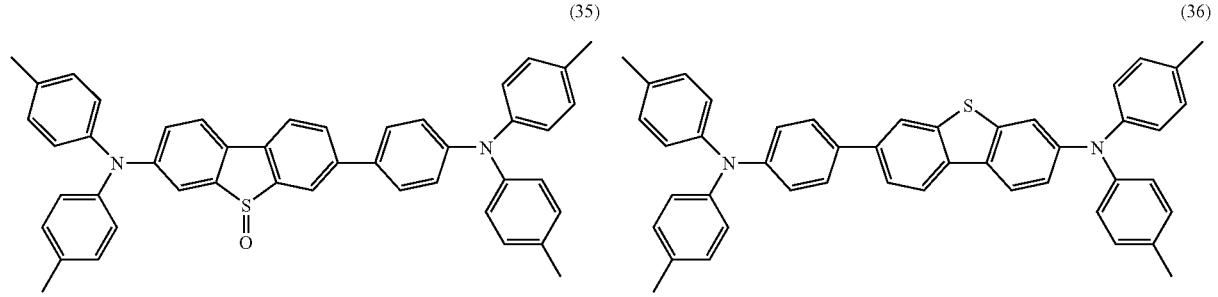
(35) (36)
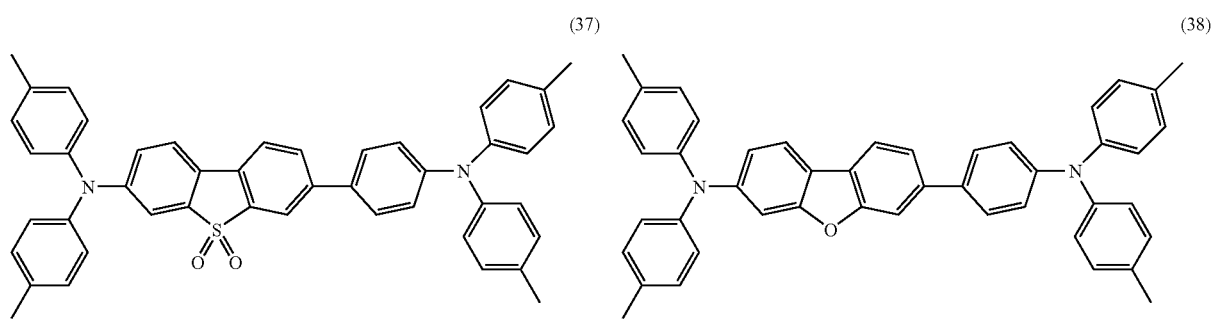
(37) (38)

-continued
(39)
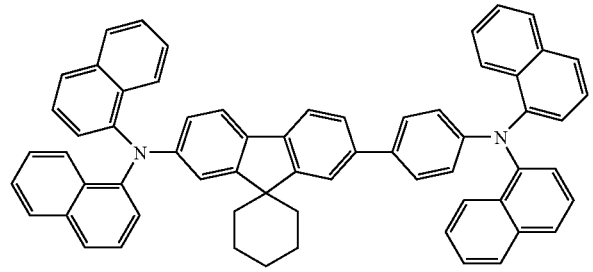
(40)
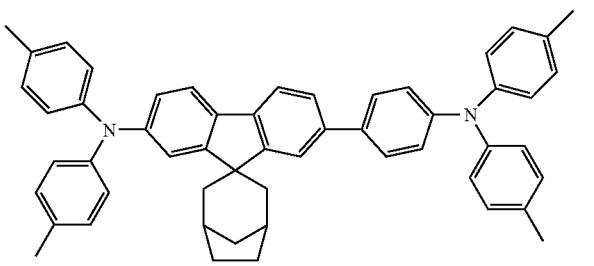
(41)
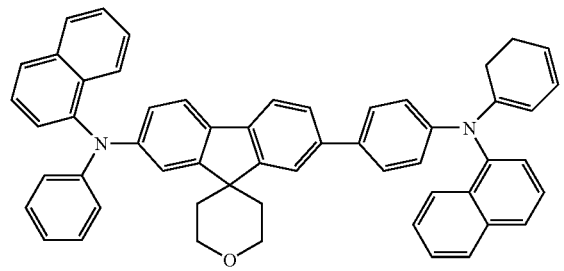
(42)
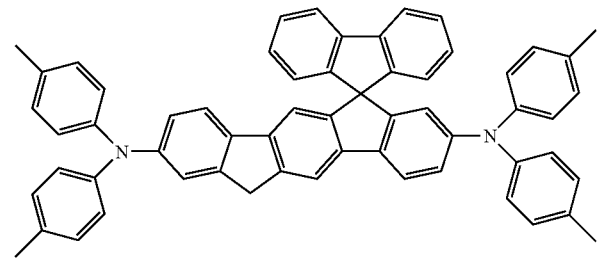
(43)
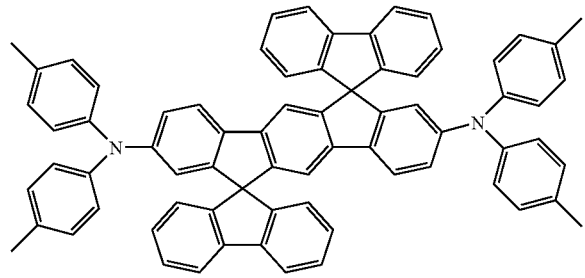
(44)
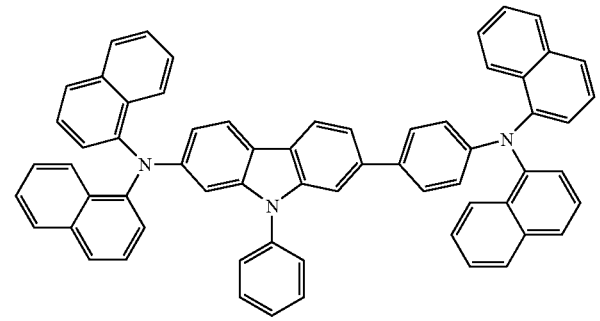
(45)
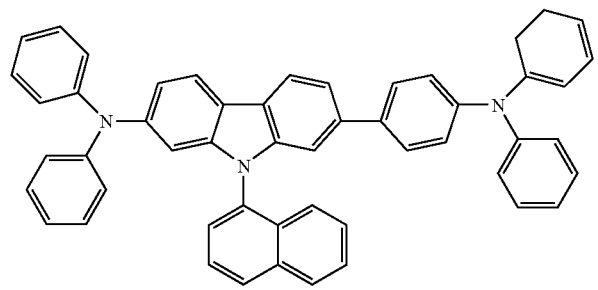
(46)
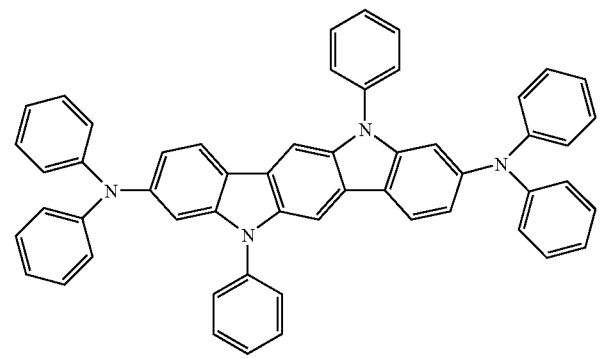

-continued
(47)
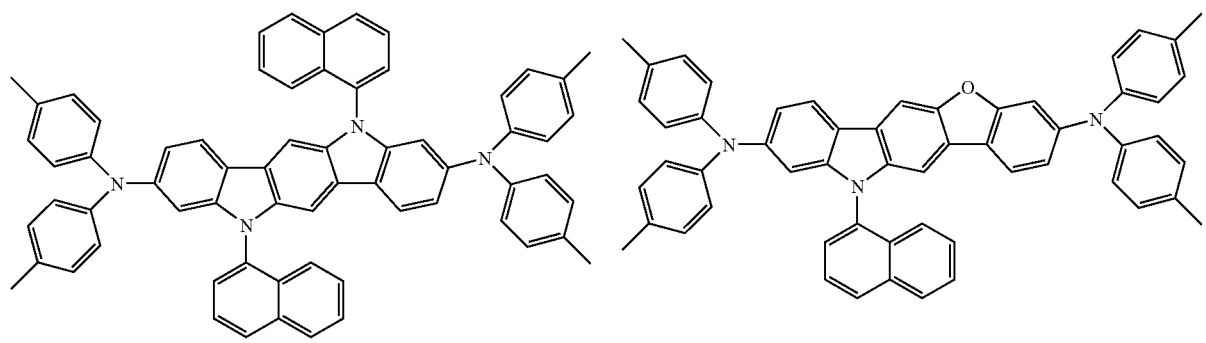
(48)
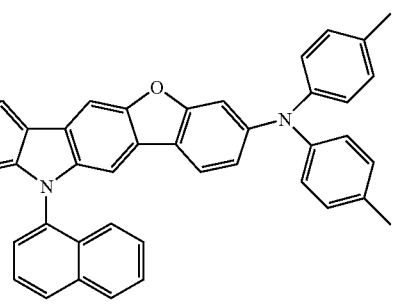
(49) (50)
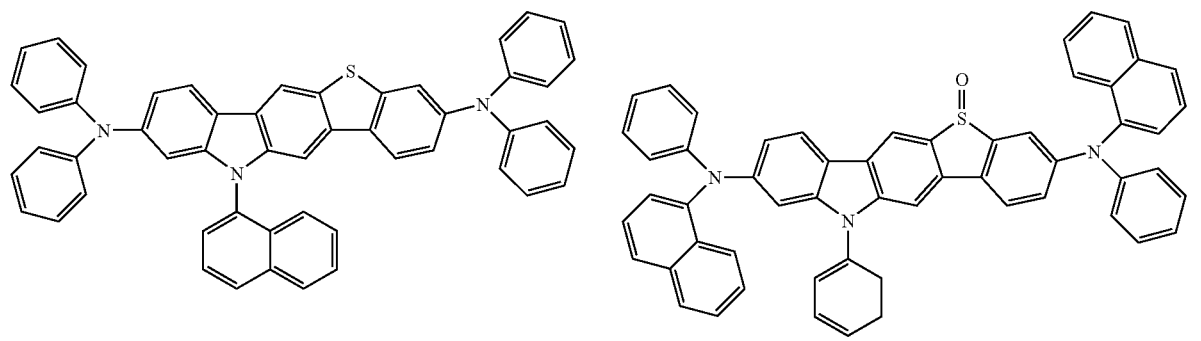
(51) (52)
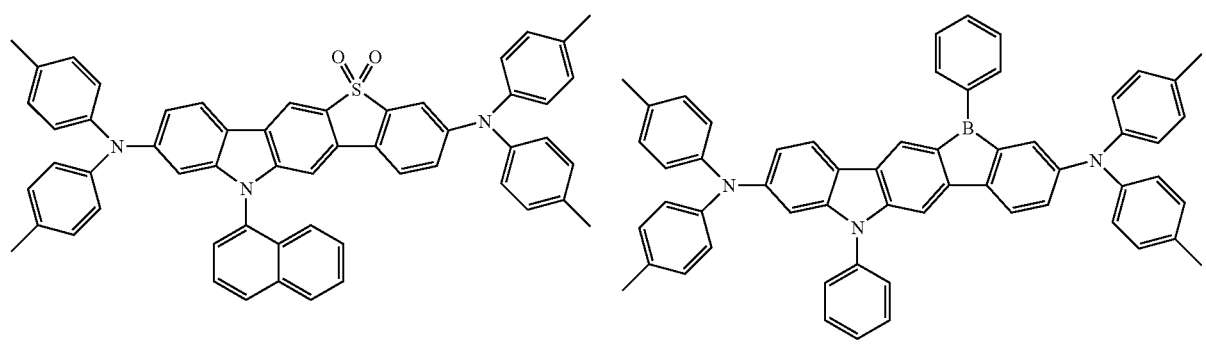
(53) (54)
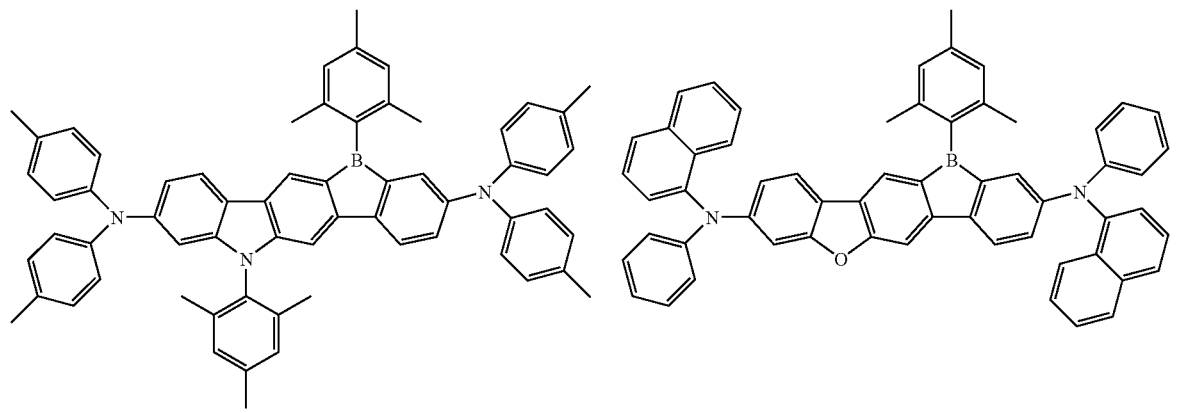

-continued
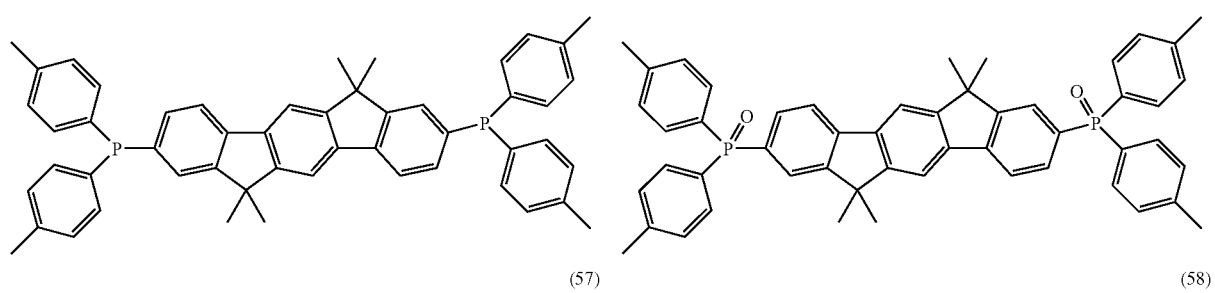
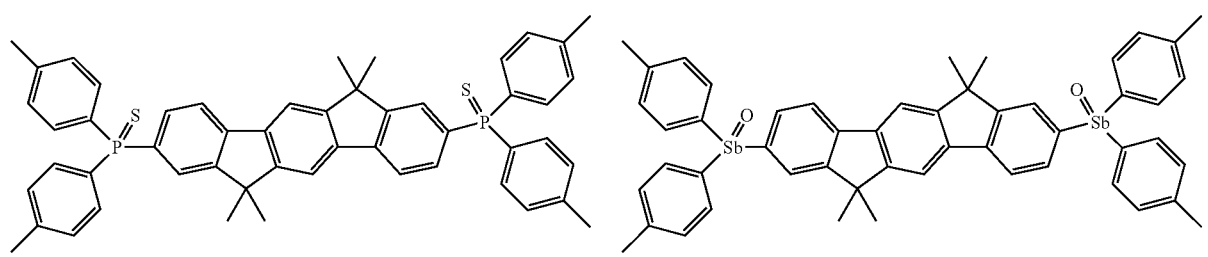
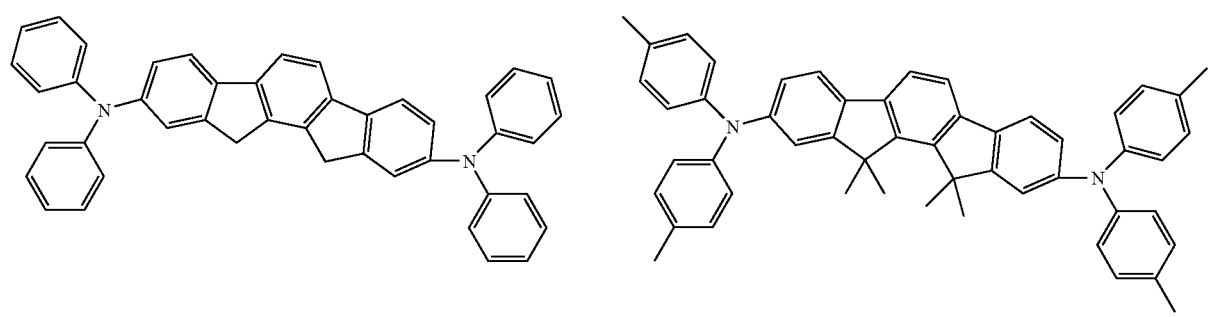
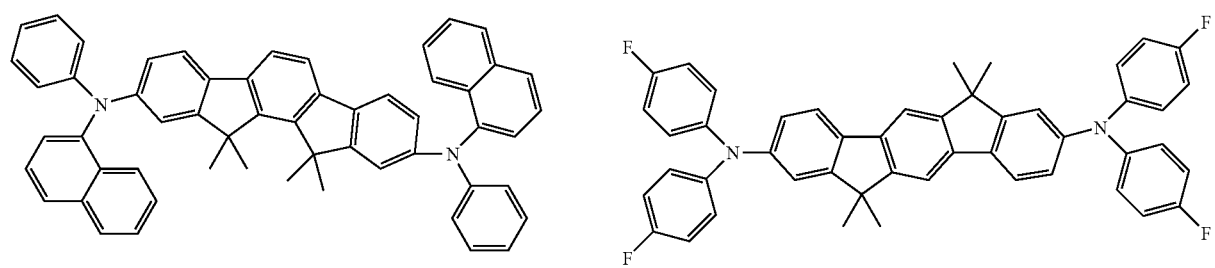
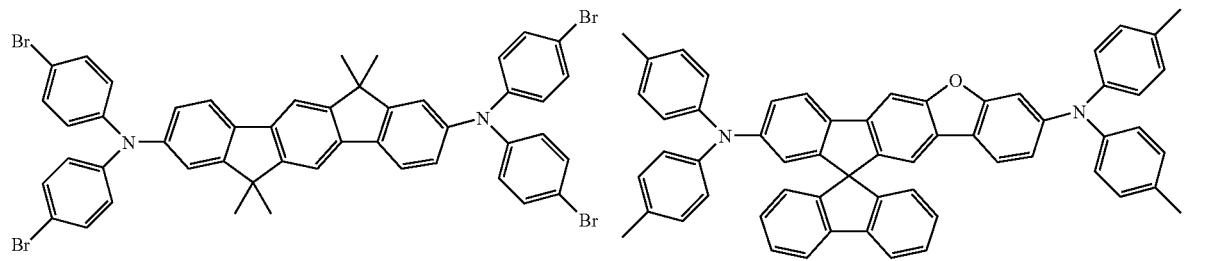

(65)
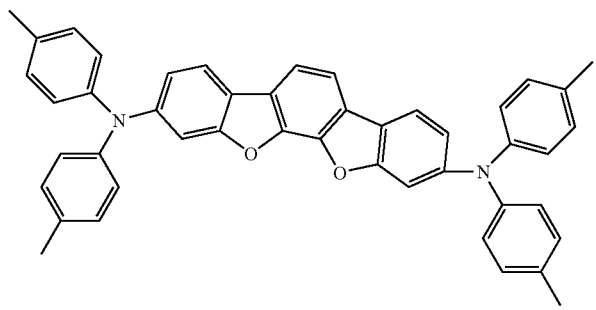
(66)
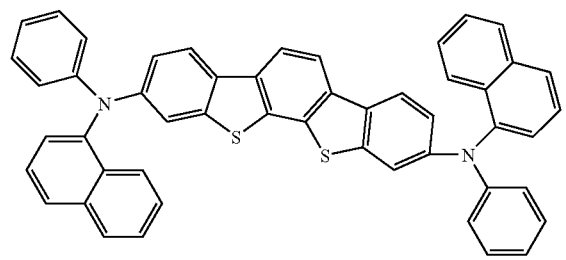
(67)
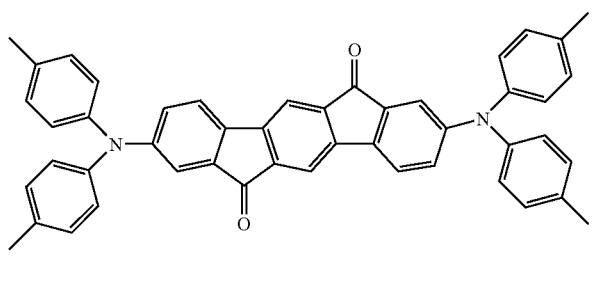
(68)
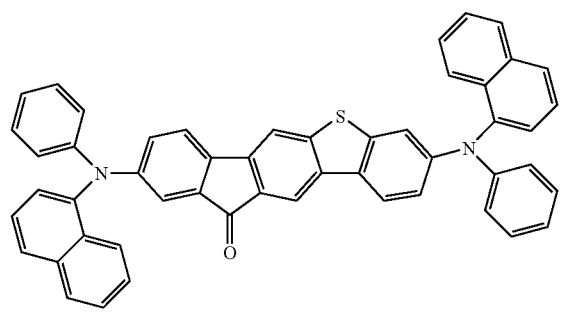
(69)
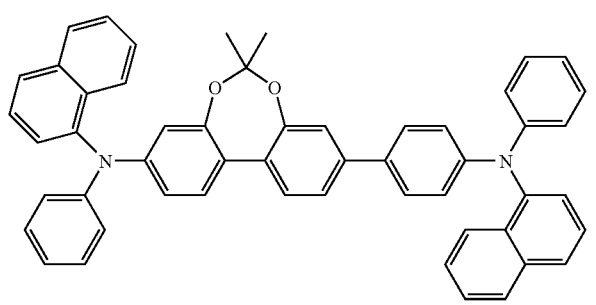
(70)
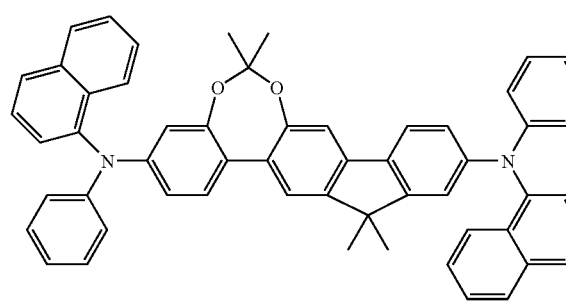
(71)
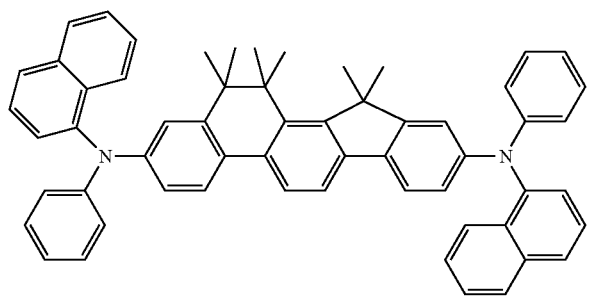
(72)
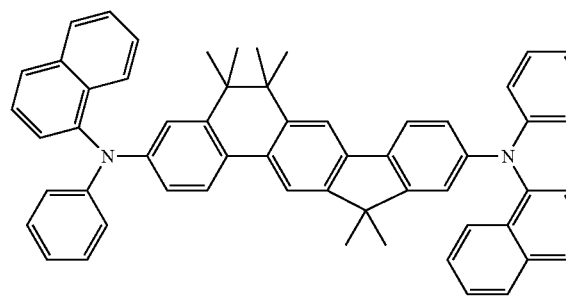
(73)
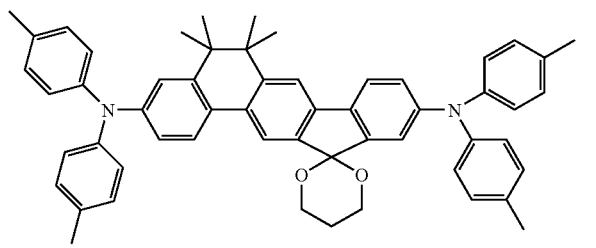
(74)
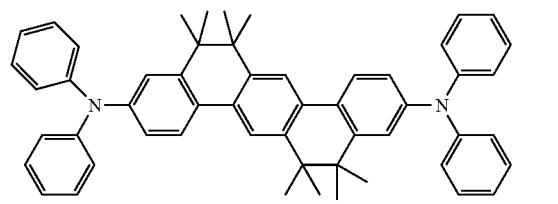

-continued
(75) 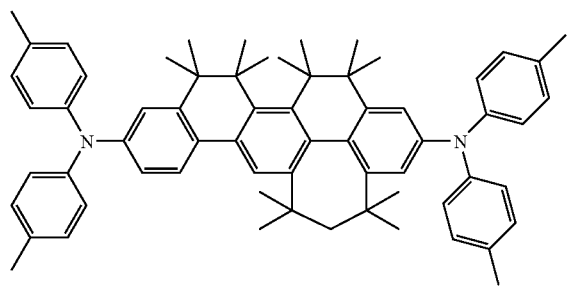
(76) 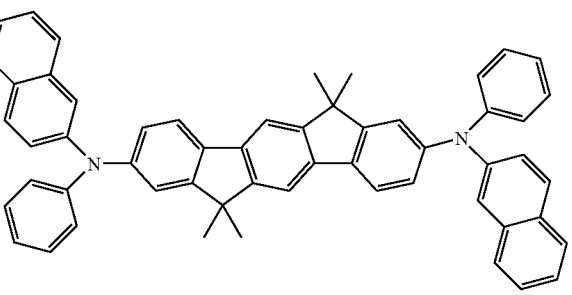
(77) 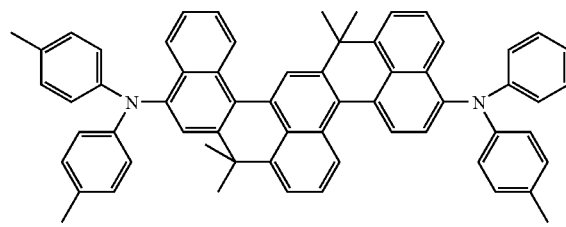
(78) 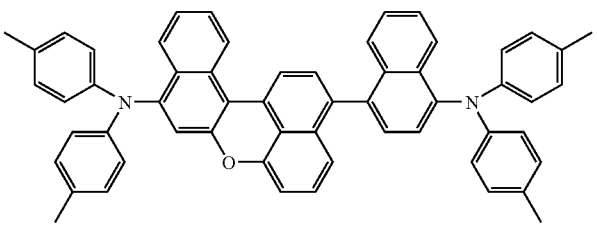
(79) 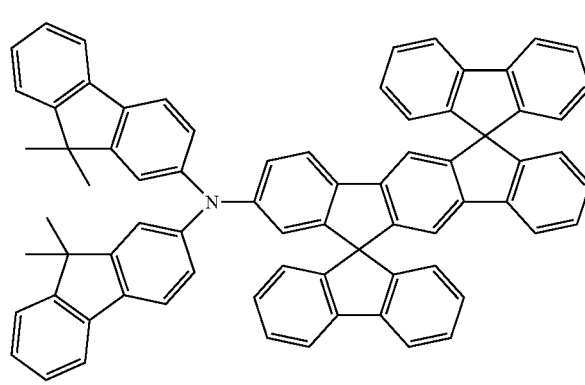
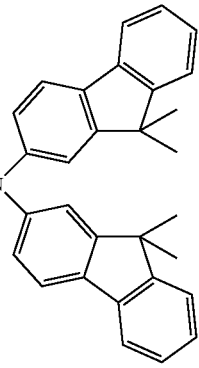
(80) 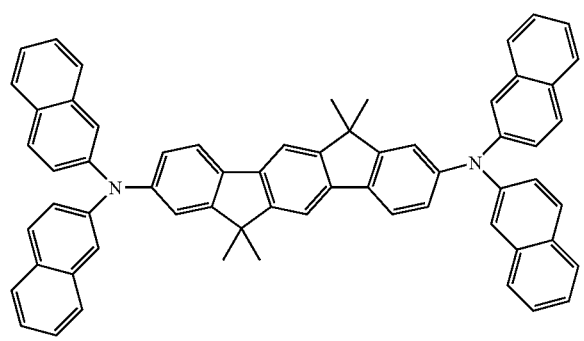
(81) 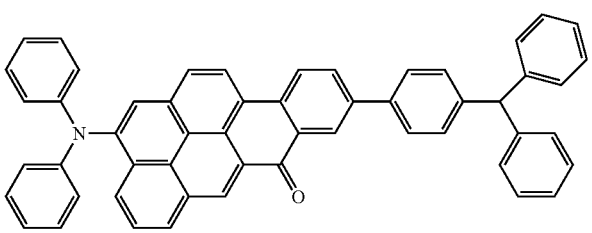
(82) 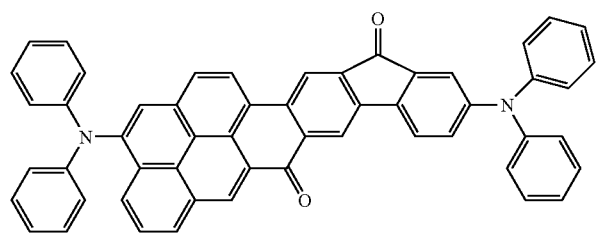
(83) 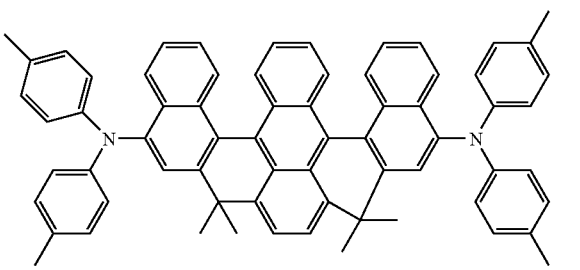

-continued
(84)
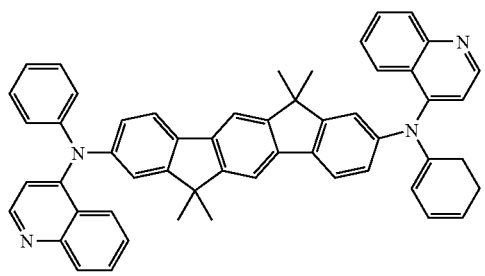
(85)
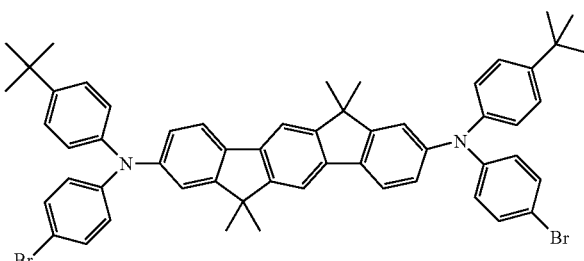
(86)
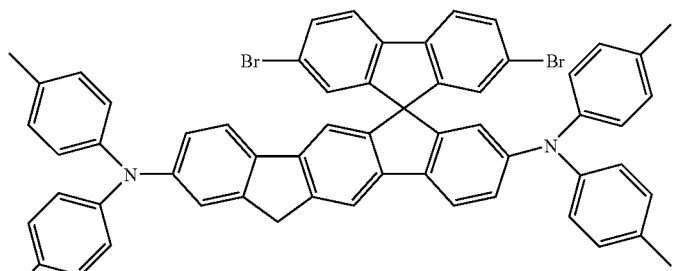
(87)
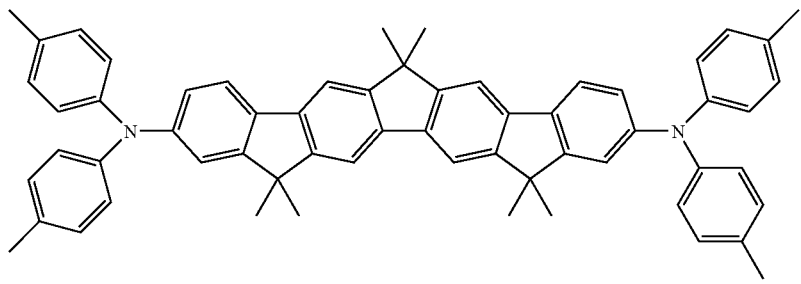
(88)
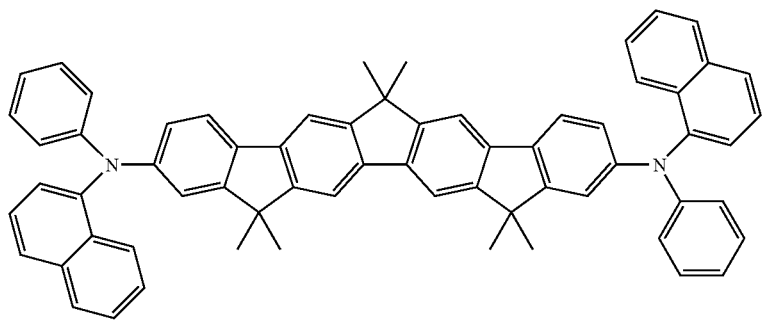
(89)
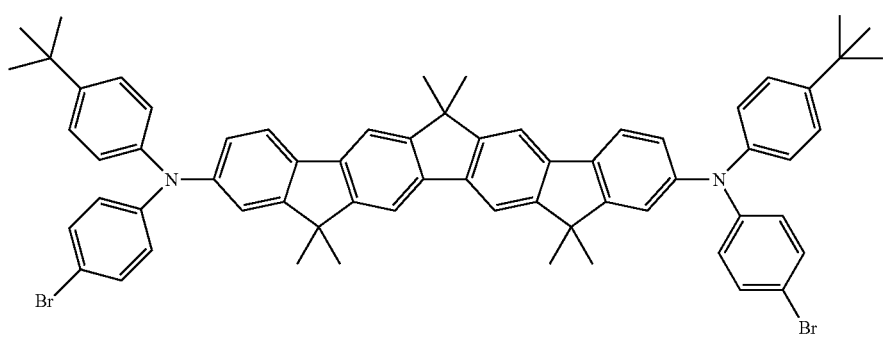

-continued
(90)
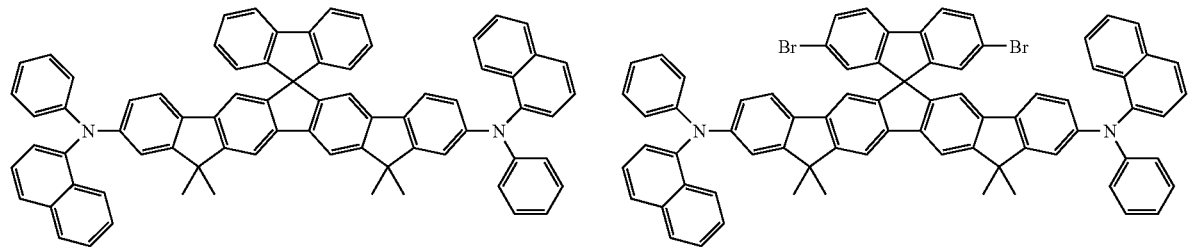
(91)
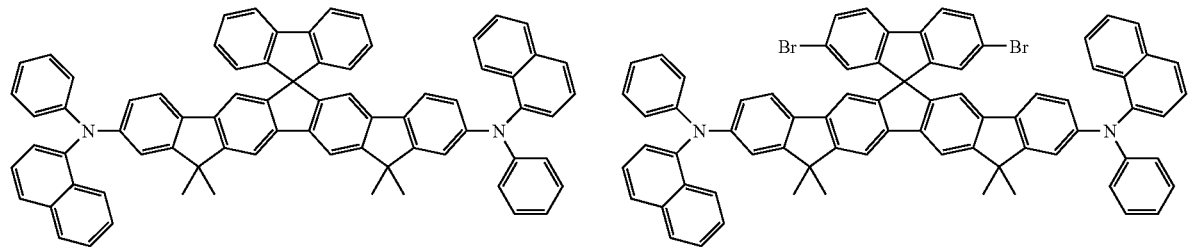
(92)
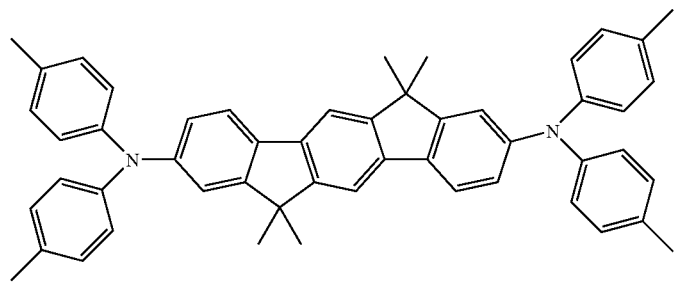
(93)
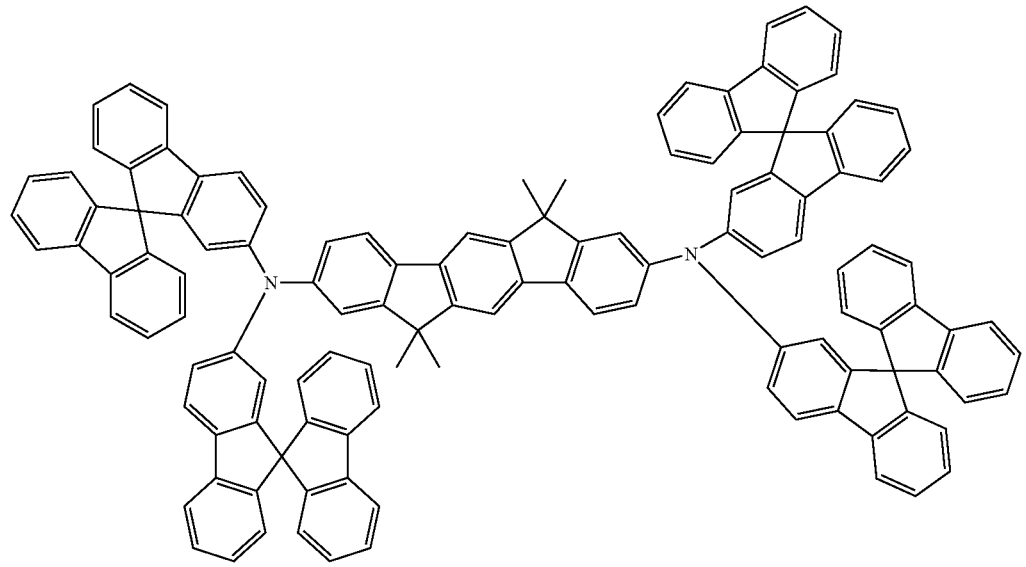
(94)
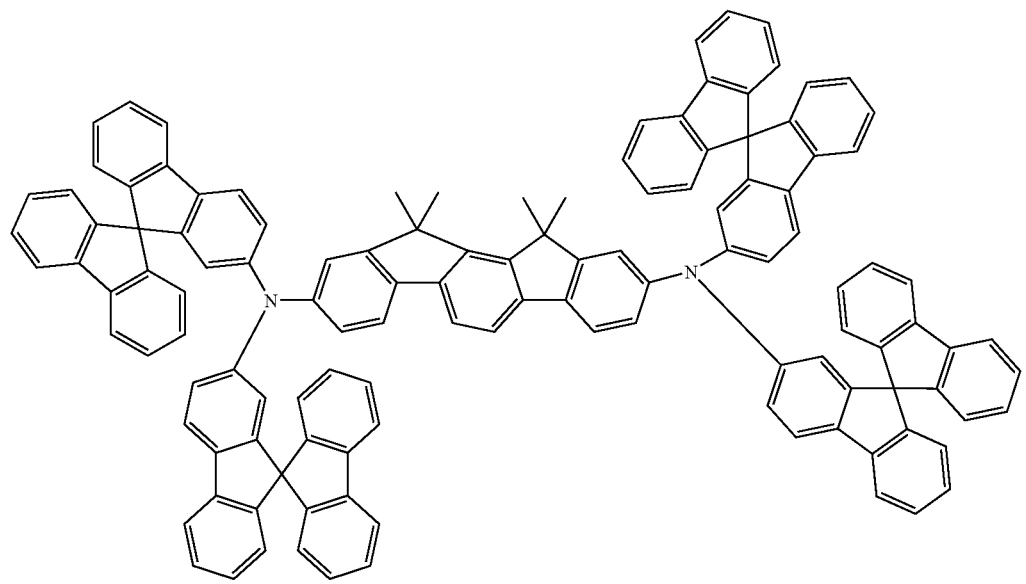

(95)
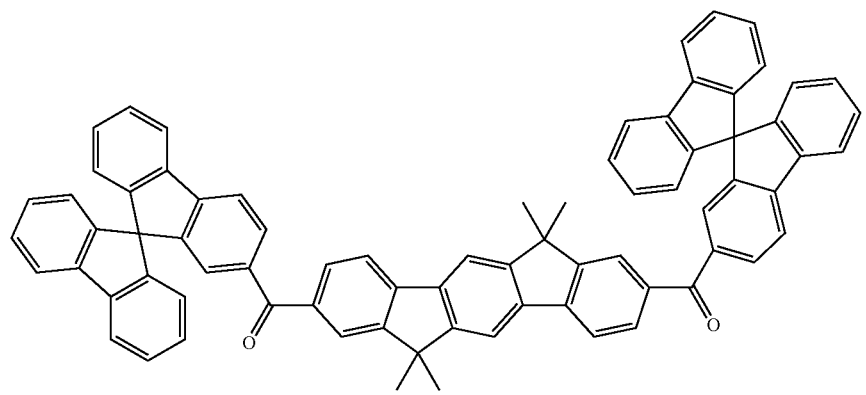
(96)
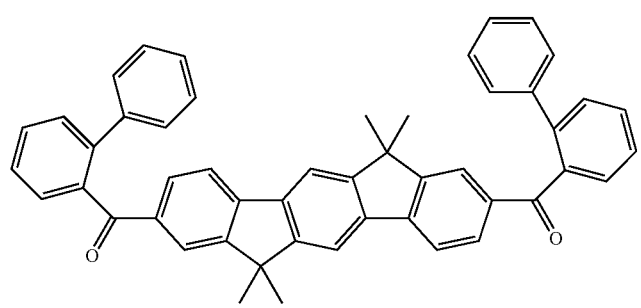
(97)
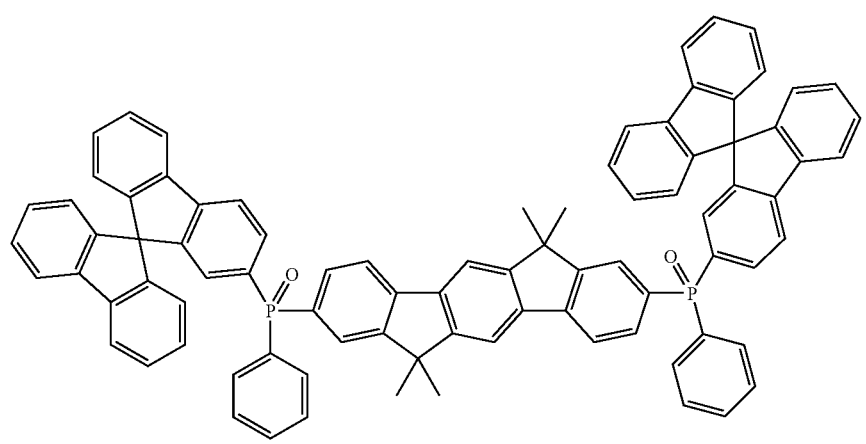
(98) (99)
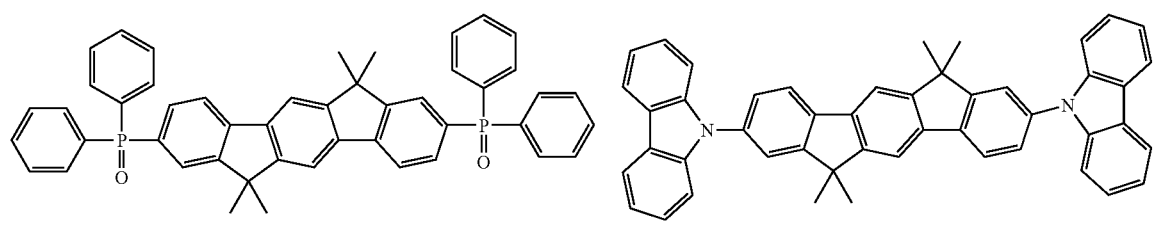

(100)
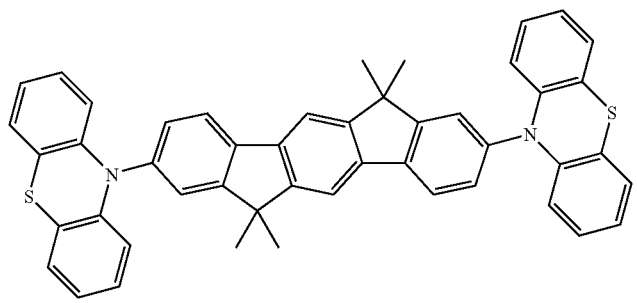
(101)
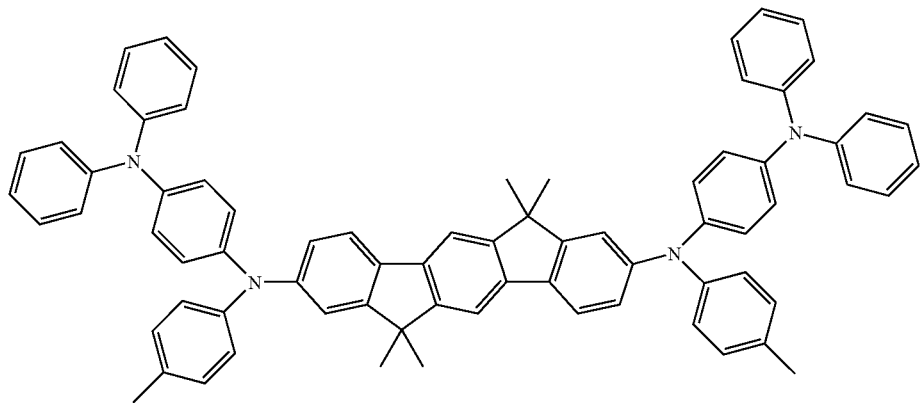
(102)
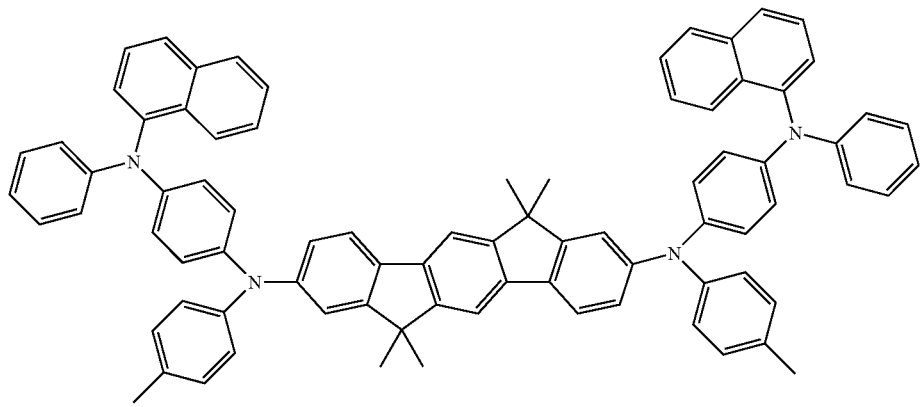
(103)
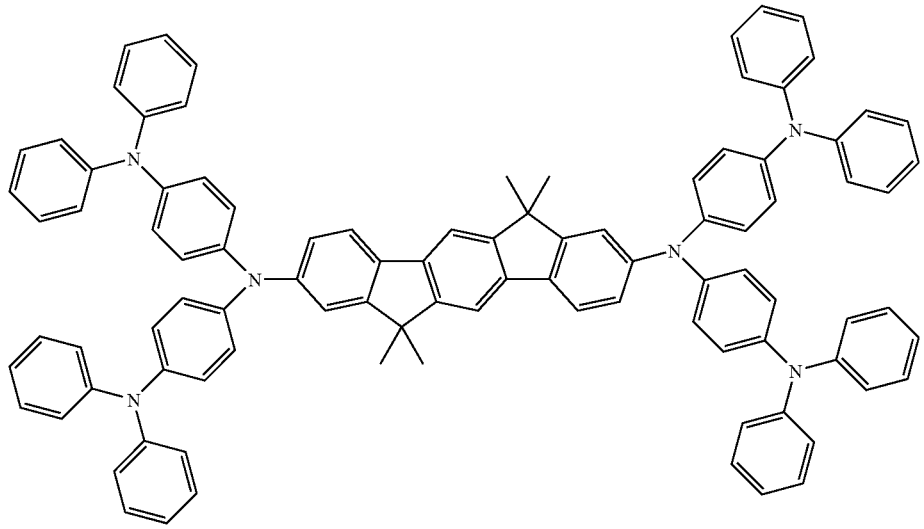

(104)

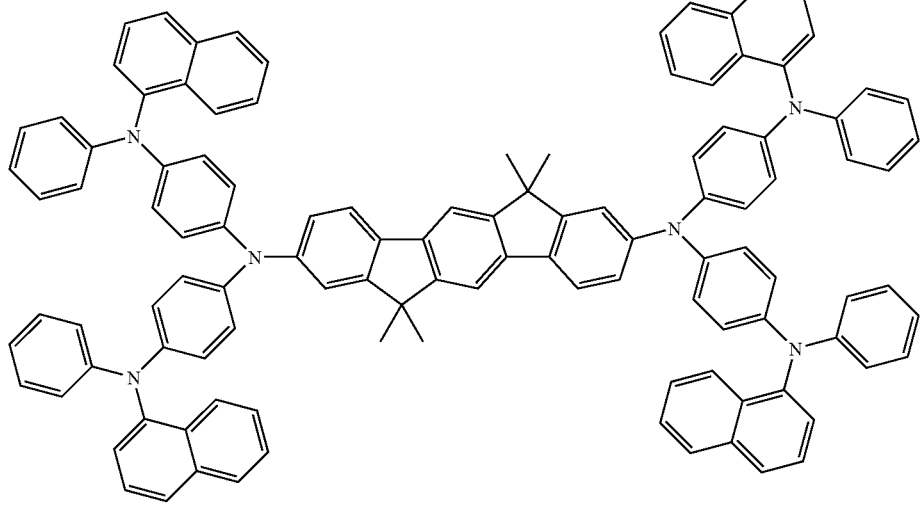

The compounds according to the invention described above, for example compounds in accordance with structures (63), (85), (86), (89) and (91), can be used, for example, as comonomers for the production of corresponding conjugated, partially conjugated or non-conjugated polymers, oligomers or also as the core of dendrimers. The polymerisation here is preferably carried out via the halogen functionality.

The invention thus furthermore relates to conjugated, partially conjugated and non-conjugated polymers, oligomers and dendrimers comprising one or more compounds of the formula (1), where one or more radicals $R^1$ represent bonds from the compound of the formula (1) to the polymer or dendrimer. The unit of the formula (1) is preferably bonded into the polymer via the groups $Ar^4$, $Ar^5$, $Ar^6$ and/or $Ar^7$.

These polymers may comprise further recurring units. These further recurring units are preferably selected from the group consisting of fluorenes (for example in accordance with EP 842208 or WO 00/22026), spirobifluorenes (for example in accordance with EP 707020, EP 894107 or EP 04028865.6), triarylamines, para-phenylenes (for example in accordance with WO 92/18552), carbazoles (for example in accordance with WO 041070772 and WO 04/113468), thiophenes (for example in accordance with EP 1028136), dihydrophenanthrenes (for example in accordance with WO 05/014689), indenofluorenes (for example in accordance with WO 04/041901 and WO 04/113412), aromatic ketones (for example in accordance with WO 05/040302), phenanthrenes (for example in accordance with WO 051104264) and/or metal complexes, in particular ortho-metallated iridium complexes. It should be expressly pointed out here that the polymers may also have a plurality of different recurring units selected from one or more of the above-mentioned groups.

The compounds according to the invention can be prepared by synthetic steps known to the person skilled in the art, such as, for example, bromination, Suzuki coupling, Hartwig-Buchwald coupling, etc.

Thus, the indenofluorene precursors can be prepared, for example, as shown in synthesis scheme 1: Suzuki coupling of a benzeneboronic acid and 1,4-dibromo-2,5-bis(methyl carboxylate)benzene followed by ring closure under the action of a strong acid and reduction gives access to the unsubstituted trans-indenofluorene, which can be alkylated using alkylating agents. This can either be halogenated, for example brominated, or converted into the corresponding amino compound by nitration and reduction. Bisdiarylaminoindenofluorenes can be synthesised by Hartwig-Buchwald coupling of the dibromo compound, as shown in synthesis scheme 2.

Indenofluorene-containing phosphines and phosphine oxides can be synthesised from dibromoindenofluorene by lithiation and reaction with diaryl-chlorophosphines, as shown in synthesis scheme 3. Oxidation then gives the corresponding phosphine oxide. Other electrophiles can also be employed here, such as, for example, $AsCl_3$, $arylPCl_2$, $SOCl_2$, $Ar_2S_2$, etc. Further compounds according to the invention can easily be synthesised in accordance with these and similar synthesis schemes by processes known to the person skilled in the art for organic synthesis. Furthermore, the compounds obtained can be brominated by standard processes and can thus be employed as monomers for polymers, oligomers or dendrimers.

Synthesis scheme 1: Precursors of indenofluorene derivatives

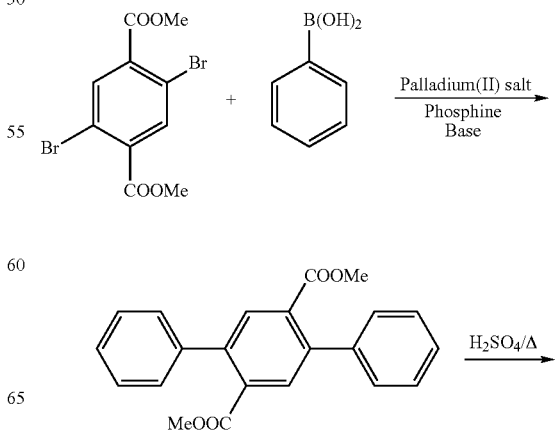

-continued

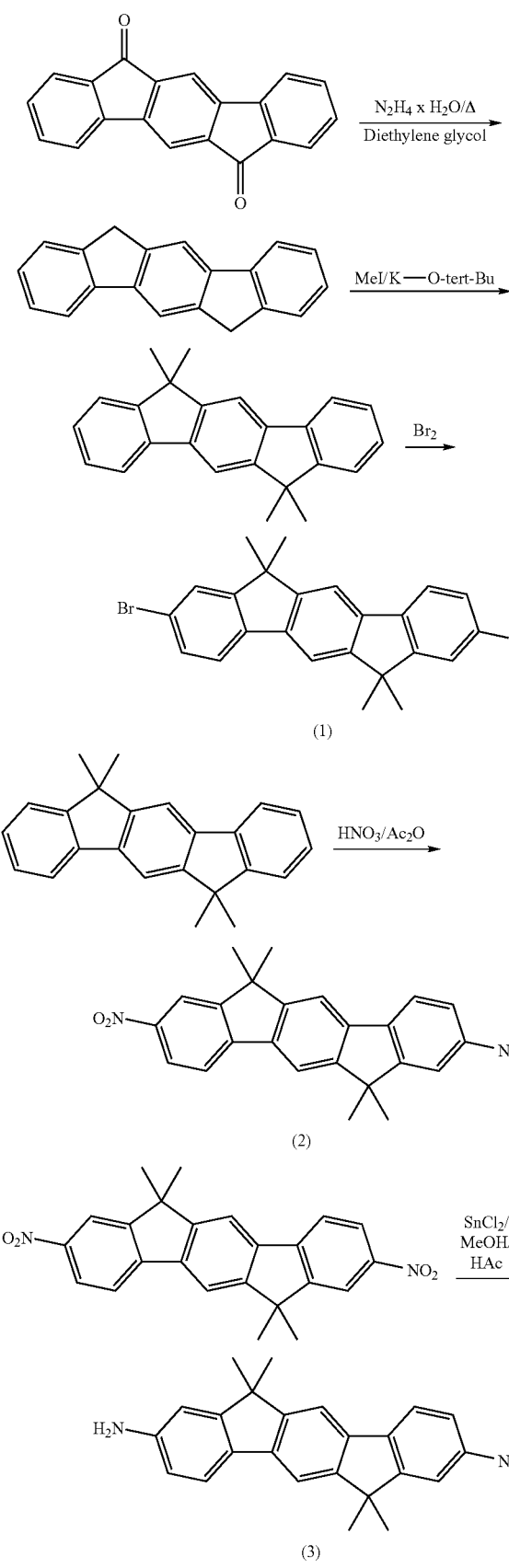

Synthesis scheme 2: Indenofluorene-amine compounds

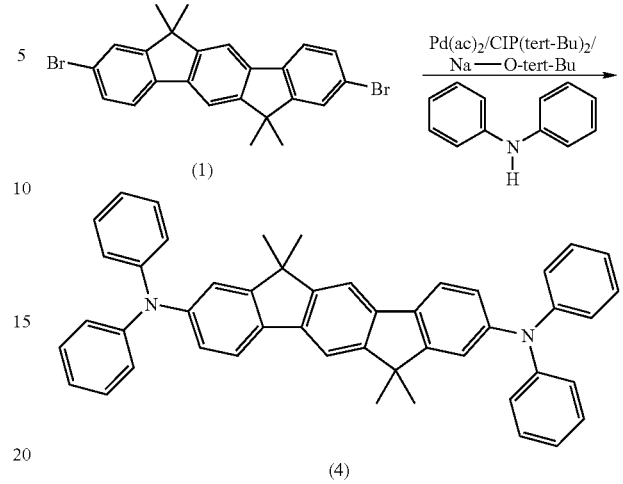

Synthesis scheme 3: Indenofluorene-phosphine compounds

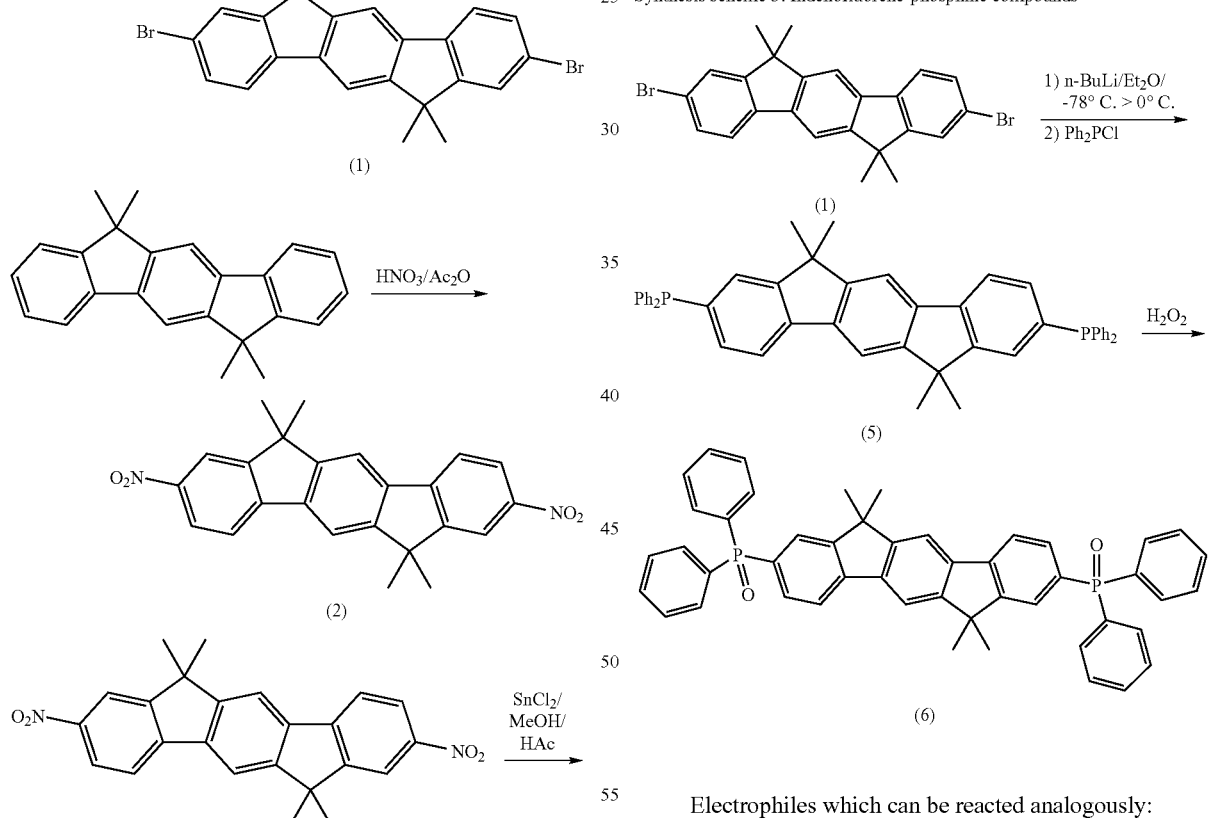

Electrophiles which can be reacted analogously:
$AsCl_3$, $SbCl_3$, $BiCl_3$, $arylPCl_2$, $aryl_2PCl$, $SCl_2$, $SOCl_2$, $SO_2Cl_2$, $Ar_2S_2$, $Ar_2Se_2$, $Ar_2Te_2$, etc.

The compounds of the formula (1) can be employed in organic electroluminescent devices. The precise use of the compounds here depends on the substituents and in particular on the choice of groups Y and Z, but also on the choice of groups $X^1$ to $X^4$.

In a preferred embodiment of the invention, the compound of the formula (1) is employed in the emitting layer, preferably in a mixture with at least one further compound. It is preferred for the compound of the formula (1) in the mixture to be the emitting compound (the dopant). This applies in particular if the symbols Y and Z stand for nitrogen. Preferred host materials are organic compounds whose emission is of shorter wavelength than that of the compound of the formula (1) or which do not emit at all.

The invention therefore furthermore relates to mixtures of one or more compounds of the formula (1) with one or more host materials.

The proportion of the compound of the formula (1) in the mixture of the emitting layer is between 0.1 and 99.0% by weight, preferably between 0.5 and 50.0% by weight, particularly preferably between 1.0 and 20.0% by weight, in particular between 1.0 and 10.0% by weight. Correspondingly, the proportion of the host material in the layer is between 1.0 and 99.9% by weight, preferably between 50.0 and 99.5% by weight, particularly preferably between 80.0 and 99.0% by weight, in particular between 90.0 and 99.0% by weight.

Suitable host materials are various classes of substance. Preferred host materials are selected from the classes of oligoarylenes (for example 2,2',7,7'-tetraphenylspirobifluorene in accordance with EP 676461 or dinaphthylanthracene), in particular oligoarylenes containing fused aromatic groups, oligoarylenevinylenes (for example DPVBi or spiro-DPVBi in accordance with EP 676461), polypodal metal complexes (for example in accordance with WO 04/081017), hole-conducting compounds (for example in accordance with WO 04/058911), electron-conducting compounds, in particular ketones, phosphine oxides, sulfoxides, etc. (for example in accordance with WO 05/084081 or WO 05/084082), atropisomers (for example in accordance with the unpublished application EP 04026402.0) or boronic acid derivatives (for example in accordance with the unpublished application EP 05009643.7). Particularly preferred host materials are selected from the classes of oligoarylenes containing naphthalene, anthracene and/or pyrene or atropisomers of these compounds, oligoarylenevinylenes, ketones, phosphine oxides and sulfoxides. Very particularly preferred host materials are selected from the classes of oligoarylenes containing anthracene and/or pyrene or atropisomers of these compounds, phosphine oxides and sulfoxides.

It is furthermore particularly preferred for the compounds of the formula (1) to be employed as hole-transport material and/or as hole-injection material. This applies, in particular, if the symbols Y and Z and/or the symbols $X^1$ to $X^4$ stand for nitrogen. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. If the compounds of the formula (1) are used as hole-transport or hole-injection material, it may be preferred for them to be doped with electron-acceptor compounds, for example with $F_4$-TCNQ, or with compounds as described in EP 1476881 or EP 1596445.

If the compound of the formula (1) is employed as hole-transport material in a hole-transport layer, it may also be preferred to use a proportion of 100%, i.e. to use this compound as the pure material.

It is furthermore preferred to employ the compounds of the formula (1) as electron-transport material and/or as hole-blocking material for fluorescent and phosphorescent OLEDs and/or as triplet matrix material for phosphorescent OLEDs. This applies, in particular, to compounds in which the groups Y and Z stand for C=O, P=O or S=O.

Compounds of the formula (1) can also be employed in polymers, either as emitting unit and/or as hole-transporting unit and/or as electron-transporting unit.

Preference is furthermore given to organic electroluminescent devices, characterised in that a plurality of emitting compounds are used in the same layer or in different layers, where at least one of these compounds has a structure of the formula (1). These compounds particularly preferably have in total a plurality of emission maxima between 380 nm and 750 nm, overall resulting in white emission, i.e. in addition to the compound of the formula (1), at least one further emitting compound, which may be fluorescent or phosphorescent and emits yellow, orange or red light, is also used. Particular preference is given to three-layer systems, where at least one of these layers comprises a compound of the formula (1) and where the layers exhibit blue, green and orange or red emission (for the basic structure, see, for example, WO 05/011013). Broad-band emitters can also be used for white-emitting OLEDs.

In addition to cathode, anode and the emitting layer, the organic electroluminescent device may also comprise further layers. These may be, for example: hole-injection layer, hole-transport layer, hole-blocking layer, electron-transport layer, electron-injection layer and/or a charge-generation layer (T. Matsumoto et al., *Multiphoton Organic EL Device Having Charge Generation Layer*, IDMC 2003, Taiwan; Session 21 OLED (5)). However, it should be pointed out at this point that each of these layers does not necessarily have to be present. Thus, in particular on use of compounds of the formula (1) with electron-conducting host materials, very good results are furthermore obtained if the organic electroluminescent device does not comprise a separate electron-transport layer and the emitting layer is directly adjacent to the electron-injection layer or to the cathode. Alternatively, the host material may also simultaneously serve as electron-transport material in an electron-transport layer. It may likewise be preferred for the organic electroluminescent device not to comprise a separate hole-transport layer and for the emitting layer to be directly adjacent to the hole-injection layer or to the anode. It may furthermore be preferred for the compound of the formula (1) to be used simultaneously as dopant in the emitting layer and as hole-conducting compound (as pure substance or as a mixture) in a hole-transport layer and/or in a hole-injection layer.

Preference is furthermore given to an organic electroluminescent device, characterised in that one or more layers are coated by a sublimation process. The materials here are vapour-deposited in vacuum sublimation units at a pressure of below $10^{-5}$ mbar, preferably below $10^{-6}$ mbar, particularly preferably below $10^{-7}$ mbar.

Preference is likewise given to an organic electroluminescent device, characterised in that one or more layers are coated by the OVPD (organic vapour phase deposition) process or with the aid of carrier-gas sublimation. The materials here are applied at a pressure between $10^{-5}$ mbar and 1 bar.

Preference is furthermore given to an organic electroluminescent device, characterised in that one or more layers are produced from solution, such as, for example, by spin coating, or by any desired printing process, such as, for example, screen printing, flexographic printing or offset printing, but particularly preferably LITI (light induced thermal imaging, thermal transfer printing) or ink-jet printing. Soluble compounds of the formula (1) are necessary for this purpose. High solubility can be achieved by suitable substitution of the compounds. These processes for the production of layers are particularly suitable for polymers.

The compounds according to the invention have the following surprising advantages over the prior art on use in organic electroluminescent devices:
1. The efficiency of corresponding devices is higher compared with systems in accordance with the prior art.
2. The stability of corresponding devices is higher compared with systems in accordance with the prior art, which is particularly evident in a significantly longer lifetime.

3. On use of the compounds according to the invention as hole-transport material in a hole-transport and/or hole-injection layer, it is found that the voltage is independent of the layer thickness of the corresponding hole-transport or hole-injection layer. By contrast, materials in accordance with the prior art with relatively large thicknesses of the hole-transport or hole-injection layers give a significant increase in voltage, which in turn results in lower power efficiency of the OLED.
4. The compounds can be sublimed well and without considerable decomposition, are consequently easier to process and are therefore more suitable for use in OLEDs than materials in accordance with the prior art. Without wishing to be tied to a particular theory, we assume that the higher thermal stability is attributable to the absence of olefinic double bonds.

In the present application text and also in the examples following below, the aim is the use of the compounds according to the invention in relation to OLEDs and the corresponding displays. In spite of this restriction of the description, it is readily possible for the person skilled in the art, without an inventive step, also to use the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or also organic laser diodes (O-lasers), to mention but a few applications.

The present invention likewise relates to the use of the compounds according to the invention in the corresponding devices and to these devices themselves.

The invention is explained in greater detail by the following examples, without wishing to be restricted thereby.

EXAMPLES

The following syntheses are carried out under a protective-gas atmosphere, unless indicated otherwise. The starting materials can be purchased from ALDRICH or ABCR (palladium(II) acetate, di-tert-butylchlorophosphine, amines, inorganics, solvents). 6,12-Dihydro[1,2b]indenofluorene is prepared by the method of Hadizad et al., Org. Lett. 2005, 7(5), 795-797, [1,2b]indenofluorene-6,12-dione is prepared by the method of Deuschel et al., Helv. Chim. Acta 1951, 34, 2403, 2-bromo-4,4'-di-tert-butylbiphenyl is prepared by the method of Tashiro et al., J. Org. Chem. 1979, 44(17), 3037, 1,4-dibromo-2,5-diiodobenzene is prepared by the method of Chanteau et al., J. Org. Chem. 2003, 68(23), 8750, 3,9-dibromo-5,11-dimethylindolo[3,2-b]carbazole is prepared analogously to 3,9-dibromo-5,11-bisdodecylindolo[3,2-b]carbazole by the method of Li et al., Adv. Mat. 2005, 17(7), 849.

Example 1

2,8-Bis(diphenylamino)-6,6,12,12-tetramethyl-6,12-dihydroindeno[1,2b]fluorene a) 6,6,12,12-Tetramethyl-6,12-dihydroindeno[1,2b]fluorene

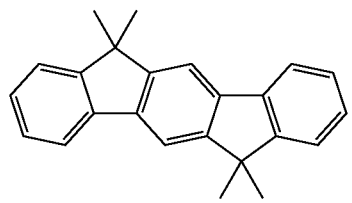 [SMILES: CC1(C)c2ccccc2-c2cc3c(cc21)-c1ccccc1C3(C)C]

The preparation is carried out analogously to the preparation of 9,9-dimethylfluorene from 6,12-dihydroindeno[1,2b]fluorene, dimethyl sulfate and sodium hydroxide solution in accordance with JP 08113542. Yield 86.0% of theory; purity 98% according to $^1$H-NMR.

b) 2,8-Dibromo-6,6,12,12-tetramethyl-6,12-dihydroindeno[1,2b]-fluorene

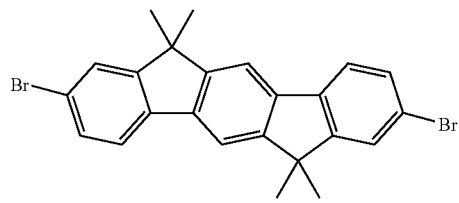 [SMILES: CC1(C)c2cc(Br)ccc2-c2cc3c(cc21)-c1ccc(Br)cc1C3(C)C]

A solution of 155.9 g (1260 mmol) of sodium carbonate in 1000 ml of water is added to a solution of 122.0 g (393 mmol) of 6,6,12,12-tetramethyl-6,12-dihydroindeno[1,2b]fluorene in 1800 ml of dichloromethane. 56.4 ml (1100 mmol) of bromine diluted with 200 ml of dichloromethane are added dropwise at +5° C. with exclusion of light and with vigorous stirring, the mixture is stirred for a further 6 h, and the precipitate is filtered off with suction and washed three times with 300 ml of water:ethanol (1:1, v:v) and then three times with 300 ml of ethanol. Yield: 178.1 g (380 mmol), 96.8% of theory; purity: 99% according to $^1$H-NMR.

c) 2,8-Bis(diphenylamino)-6,6,12,12-tetramethyl-6,12-dihydroindeno-[1,2b]fluorene

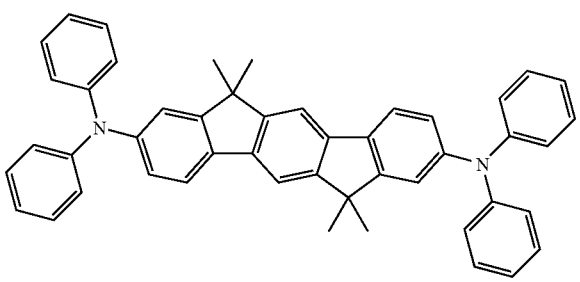 [SMILES: CC1(C)c2cc(N(c3ccccc3)c3ccccc3)ccc2-c2cc3c(cc21)-c1ccc(N(c2ccccc2)c2ccccc2)cc1C3(C)C]

23.1 g (240 mmol) of sodium tert-butoxide, 235 mg (1.3 mmol) of di-tert-butylchlorophosphine and 225 mg (1 mmol) of palladium(II) acetate are added to a suspension of 46.8 g (100 mmol) of 2,8-dibromo-6,6,12,12-tetramethyl-6,12-dihydroindeno[1,2b]fluorene and 37.2 g (220 mmol) of diphenylamine in 1000 ml of toluene, and the mixture is subsequently refluxed for 6 h. After cooling, 300 ml of water are added, and the solid is filtered off, washed three times with 300 ml of water each time and three times with 300 ml of ethanol each time, subsequently recrystallised five times from NMP and then sublimed under reduced pressure (p=1×10$^{-5}$ mbar, T=360° C.). Yield: 52.0 g (81 mmol), 80.6% of theory; purity: 99.9% according to HPLC.

Example 2

2,8-Bis(bis(4-methylphenyl)amino)-6,6,12,12-tetramethyl-6,12-dihydroindeno[1,2b]fluorene

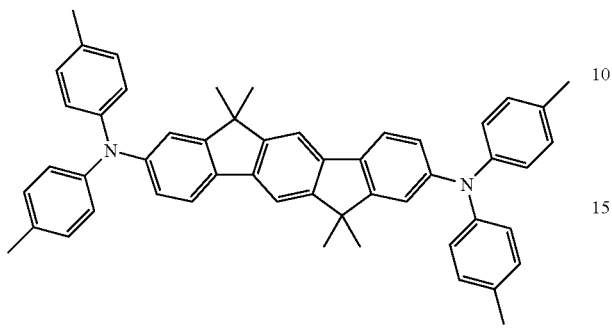

Procedure analogous to Example 1. Instead of diphenylamine, 43.4 g (220 mmol) of bis(4-methylphenyl)amine are used. Recrystallisation six times from o-dichlorobenzene, sublimation p=1×10⁻⁵ mbar, T=365° C. Yield: 45.1 g (64 mmol), 64.3% of theory; purity: 99.8% according to HPLC.

Example 3

2,8-Bis(bis(2-methylphenyl)amino)-6,6,12,12-tetramethyl-6,12-dihydroindeno[1,2b]fluorene

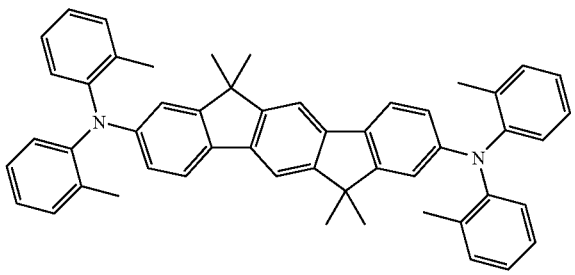 [SMILES: Cc1ccccc1N(c1ccc2c(c1)C(C)(C)c1cc3c(cc1-2)C(C)(C)c1cc(N(c2ccccc2C)c2ccccc2C)ccc1-3)c1ccccc1C]

Procedure analogous to Example 1. Instead of diphenylamine, 43.4 g (220 mmol) of bis(2-methylphenyl)amine are used. Recrystallisation five times from o-dichlorobenzene, sublimation p=1×10⁻⁵ mbar, T=360° C. Yield: 57.4 g (82 mmol), 81.9% of theory; purity: 99.9% according to HPLC.

Example 4

2,8-Bis(bis(4-tert-butylphenyl)amino)-6,6,12,12-tetramethyl-6,12-dihydroindeno[1,2b]fluorene

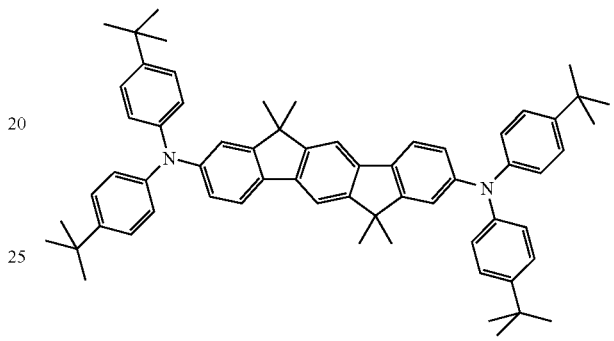

Procedure analogous to Example 1. Instead of diphenylamine, 61.9 g (220 mmol) of bis(4-tert-butylphenyl)amine are used. Recrystallisation five times from NMP, sublimation p=1×10⁻⁵ mbar, T=350° C. Yield: 73.0 g (84 mmol), 84.0% of theory; purity: 99.9% according to HPLC.

Example 5

Synthesis of Further indenofluorenamines

The following products are prepared analogously to Example 1 in a purity of 99.9% according to HPLC:

| Ex. | Amine | Product |
| --- | --- | --- |
| 6 | | |

-continued

| Ex. | Amine | Product |
|---|---|---|
| 7 | | |
| 8 | | |
| 9 | | |

-continued
| Ex. | Amine | Product |
|---|---|---|
| 10 | 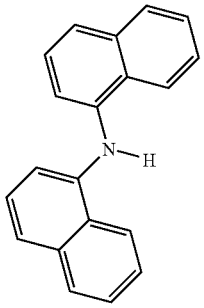 [SMILES: c1ccc2c(Nc3cccc4ccccc34)cccc2c1] | 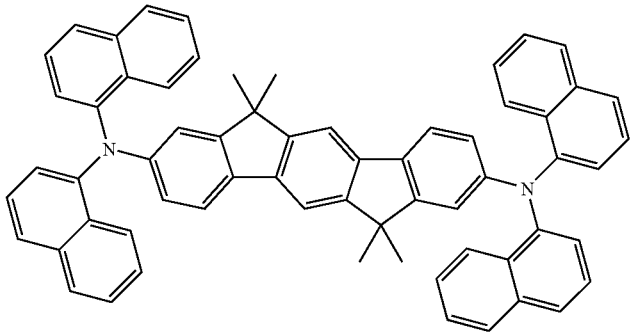 [SMILES: CC1(C)c2cc(N(c3cccc4ccccc34)c3cccc4ccccc34)ccc2-c2cc3c(cc21)-c1ccc(N(c2cccc4ccccc24)c2cccc4ccccc24)cc1C3(C)C] |
| 11 | 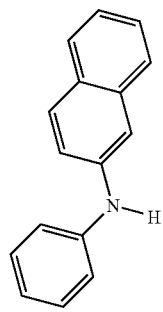 [SMILES: c1ccc(Nc2ccc3ccccc3c2)cc1] | 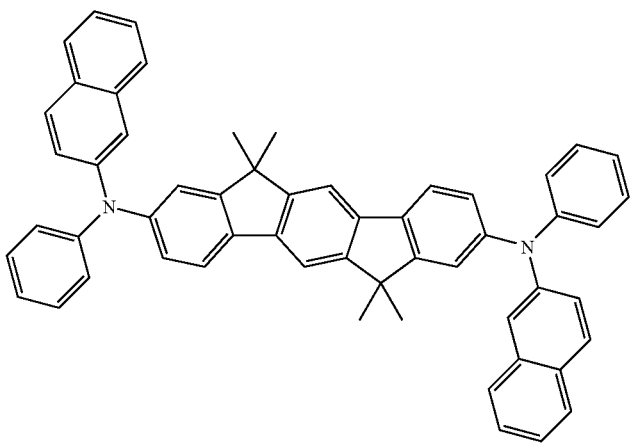 [SMILES: CC1(C)c2cc(N(c3ccccc3)c3ccc4ccccc4c3)ccc2-c2cc3c(cc21)-c1ccc(N(c2ccccc2)c2ccc4ccccc4c2)cc1C3(C)C] |
| 12 | 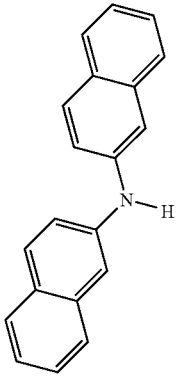 [SMILES: c1ccc2cc(Nc3ccc4ccccc4c3)ccc2c1] | 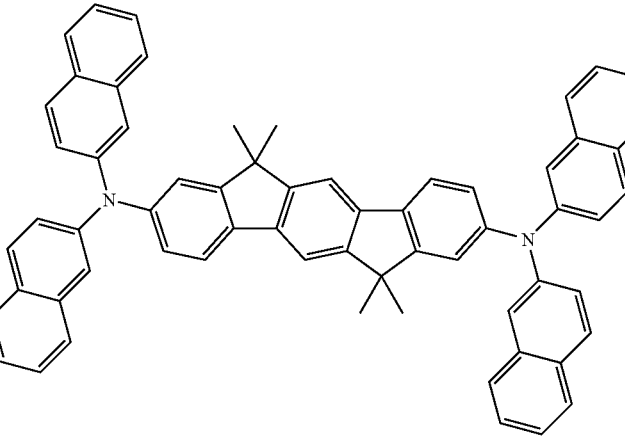 |

-continued

| Ex. | Amine | Product |
|---|---|---|
| 13 | | |
| 14 | | |
| 15 | | |
| 16 | | |

Example 17

2,8-Bis(bis(4-tert-butylphenyl)amino)dispiro[2,7-di-tert-butylfluoren-9,6'-indenofluorene[1,2b]fluorene-12',9"-fluorene]

a) Dispiro[2,7-di-tert-butylfluoren-9,6'-indenofluorene[1,2b]fluorene-12',9"-fluorene]

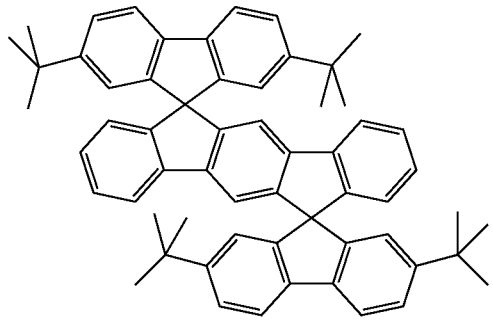 [SMILES: CC(C)(C)c1ccc2c(c1)C1(c3ccccc3-c3cc4c(cc31)-c1ccccc1C41c3cc(C(C)(C)C)ccc3-c3ccc(C(C)(C)C)cc31)c1cc(C(C)(C)C)ccc1-2]

The corresponding Grignard reagent is prepared from 6.2 g (255 mmol) of magnesium and 86.3 g (250 mmol) of 2-bromo-4,4"-di-tert-butylbiphenyl in 500 ml of THF. A further 500 ml of THF and 28.8 g (100 mmol) of [1,2b]-indenofluorene-6,12-dione are added to this Grignard reagent. The reaction mixture is refluxed for 10 h and cooled, 50 ml of ethanol are added, and the mixture is evaporated to dryness under reduced pressure. The residue is refluxed for 3 h in a mixture of 1000 ml of acetic acid and 25 ml of conc. hydrochloric acid. After cooling, the colourless crystals are filtered off with suction, washed with 100 ml of acetic acid, then three times with 100 ml of ethanol each time and dried under reduced pressure. The product is subsequently recrystallised twice from NMP. Yield: 56.9 g (73 mmol), 73.0% of theory; purity. 99% according to $^1$H-NMR.

b) 2,8-Dibromodispiro[2,7-di-tert-butylfluoren-9,6'-indenofluorene-[1,2b]fluorene-12',9"-fluorene]

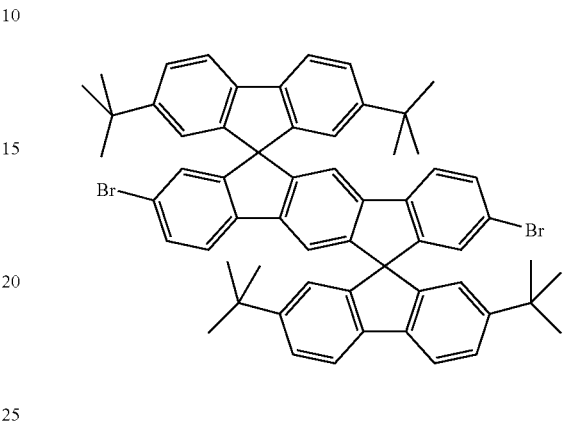

A solution of 16.8 g (200 mmol) of sodium hydrogencarbonate in 500 ml of water is added to a solution of 39.0 g (50 mmol) of dispiro[2,7-di-tert-butylfluoren-9,6'-indenofluorene[1,2b]fluorene-12',9"-fluorene] in 2000 ml of dichloromethane. 5.4 ml (105 mmol) of bromine are added dropwise to the two-phase mixture with vigorous stirring, and the mixture is stirred for a further 16 h. After addition of 1000 ml of ethanol, the solid is filtered off with suction, washed five times with 300 ml of water each time and three times with 200 ml of ethanol each time, dried under reduced pressure and recrystallised from o-dichlorobenzene. Yield: 38.7 g (41 mmol), 82.6% of theory; purity 99% according to $^1$H-NMR.

c) 2,8-Bis(bis(4-tert-butylphenyl)amino)dispiro[2,7-di-tert-butylfluoren-9,6'-indenofluorene[1,2b]fluorene-12',9"-fluorene]

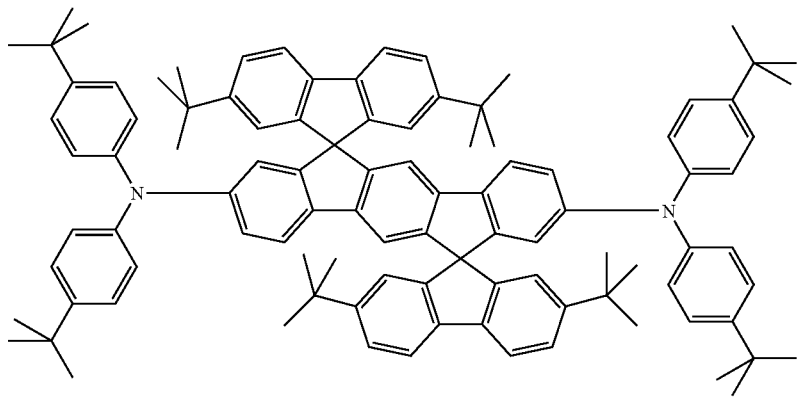 [SMILES: CC(C)(C)c1ccc(N(c2ccc(C(C)(C)C)cc2)c2ccc3c(c2)C2(c4cc(C(C)(C)C)ccc4-c4ccc(C(C)(C)C)cc42)c2cc4c(cc2-3)C2(c3cc(N(c5ccc(C(C)(C)C)cc5)c5ccc(C(C)(C)C)cc5)ccc3-4)c3cc(C(C)(C)C)ccc3-c3ccc(C(C)(C)C)cc32)cc1]

Procedure analogous to Example 1. Instead of 2,8-dibromo-6,6,12,12-tetramethyl-6,12-dihydroindeno[1,2b]fluorene, 28.1 g (30 mmol) of 2,8-dibromodispiro[2,7-di-tert-butylfluoren-9,6'-indenofluorene[1,2b]fluorene-12',9"-fluorene] are used, and instead of diphenylamine, 18.6 g (66 mmol) of di-(4-tert-butylphenyl)amine are used. Recrystallisation five times from o-dichlorobenzene, sublimation p=1×10$^{-5}$ mbar, T=390° C. Yield: 23.2 g (17 mmol), 57.8% of theory; purity: 99.9% according to HPLC.

Example 18

2,8-Bis(bis(4-methylphenyl)amino)dispiro[fluoren-9,6'-indenofluorene[1,2b]fluorene-12',9'''-fluorene]

a) 2,8-Dibromo[1,2b]indenofluorene-6,12-dione

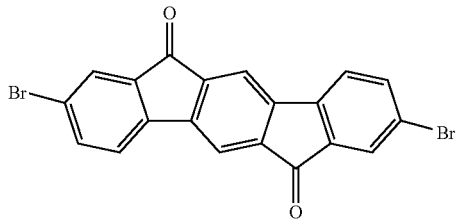 [SMILES: O=c1c2cc(Br)ccc2c2cc3c(=O)c4cc(Br)ccc4c3cc12]

30.7 ml (600 mmol) of bromine are added dropwise at 80° C. to a suspension of 56.5 g (200 mmol) of [1,2b]indenofluorene-6,12-dione and 3.0 g of iron(III) chloride (anhydrous) in 2000 ml of 1,2-dichloroethane, and the mixture is stirred at 80° C. for 30 h. After cooling, the precipitated solid is filtered off with suction, washed by stirring twice under reflux with 1000 ml of ethanol each time and dried under reduced pressure. Yield: 81.6 g (85 mmol), 92.7% of theory; purity 95% according to $^1$H-NMR.

b) 2,8-Dibromodispiro[fluoren-9,6'-indenofluorene[1,2b]fluorene-12',9"-fluorene]

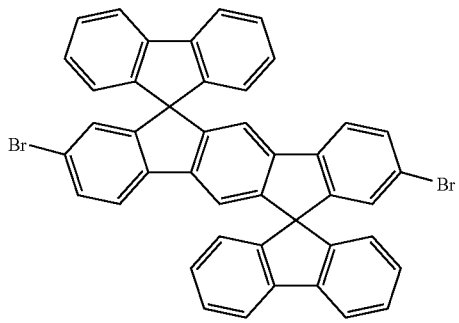 [SMILES: Brc1ccc2c(c1)C1(c3ccccc3-c3ccccc31)c1cc3c(cc1-2)C1(c2ccccc2-c2ccccc21)c1cc(Br)ccc1-3]

Preparation analogous to Example 17a. Instead of 2-bromo-4,4'-di-tert-butylbiphenyl and [1,2b]indenofluorene-6,12-dione, 58.3 g (250 mmol) of 2-bromobiphenyl and 44.0 g (100 mmol) of 2,8-dibromo[1,2b]indenofluorene-6,12-dione are employed. Recrystallisation from o-dichlorobenzene. Yield: 24.5 g (34 mmol), 34.4% of theory; purity: 98% according to $^1$H-NMR.

c) 2,8-Bis(diphenylamino)dispiro[fluoren-9,6'-indenofluorene[1,2b]-fluorene-12',9"-fluorene]

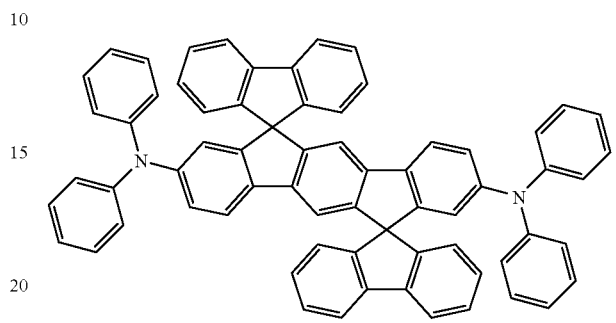

Preparation analogous to Example 1c. Instead of 2,8-dibromo-6,6,12,12-tetramethyl-6,12-dihydroindeno[1,2b]fluorene, 71.3 g (100 mmol) of 2,8-dibromodispiro[fluoren-9,6'-indenofluorene[1,2b]fluorene-12',9"-fluorene] are employed. Recrystallisation from o-dichlorobenzene, sublimation at p=1×10$^{-5}$ mbar, T=390° C. Yield: 71.9 g (81 mmol), 80.9% of theory; purity: 99.7% according to HPLC.

Example 19

2,8-Bis(phenylcarbonyl)(6,6,12,12-tetramethyl-6,12-di-hydroindeno[1,2b]fluorene)

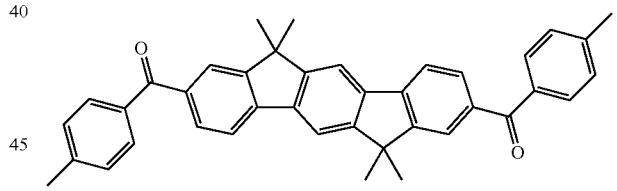

84.0 ml (210 mmol) of n-butyllithium (2.5M in hexane) are added dropwise to a suspension, cooled to −78° C., of 46.8 g (100 mmol) of 2,8-dibromo-6,6,12,12-tetramethyl-6,12-dihydroindeno[1,2b]fluorene in 700 ml of THF. The mixture is allowed to warm slowly to 0° C. over the course of 2 h and stirred at 0° C. for a further 1 h, a mixture of 27.5 ml (230 mmol) of 4-methylbenzonitrile in 100 ml of THF is then added, and the mixture is stirred at room temperature for a further 16 h. 20 ml of ethanol, then 100 ml of 1N hydrochloric acid are added dropwise to the mixture, which is then refluxed for 5 h. After cooling, the solvent is removed under reduced pressure, and the residue is taken up in 500 ml of NMP, 20 ml of water and 5 ml of acetic acid and refluxed for 5 h. After cooling, the crystals are filtered off with suction and recrystallised three times from NMP. Sublimation at p=1×10$^{-5}$ mbar, T=320° C. Yield: 44.2 g (81 mmol), 80.8% of theory; purity: 99.9% according to HPLC.

Example 20

Synthesis of Further indenofluorene carbonyls

The following products are prepared analogously to Example 19 in a purity of 99.9% according to HPLC:

| Ex. | Nitrile | Product |
|---|---|---|
| 21 | 3-methylbenzonitrile | bis(3-methylbenzoyl) indenofluorene derivative |
| 22 | 4-fluorobenzonitrile | bis(4-fluorobenzoyl) indenofluorene derivative |
| 23 | 4-(trifluoromethyl)benzonitrile | bis(4-trifluoromethylbenzoyl) indenofluorene derivative |
| 24 | 1-naphthonitrile | bis(1-naphthoyl) indenofluorene derivative |
| 25 | 2-naphthonitrile | bis(2-naphthoyl) indenofluorene derivative |

-continued
| Ex. | Nitrile | Product |
|---|---|---|
| 26 | 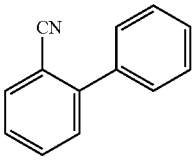 [SMILES: N#Cc1ccccc1-c1ccccc1] | 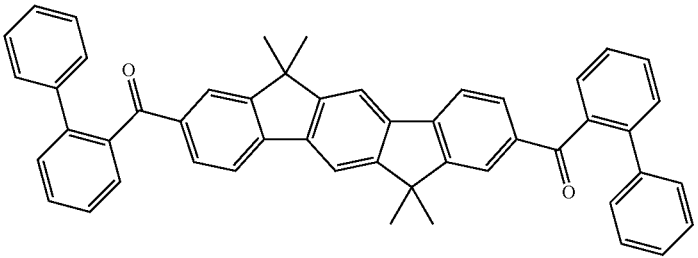 [SMILES: CC1(C)c2cc(C(=O)c3ccccc3-c3ccccc3)ccc2-c2cc3c(cc21)-c1ccc(C(=O)c2ccccc2-c2ccccc2)cc1C3(C)C] |
| 27 | 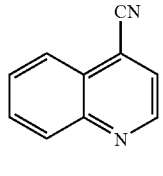 | 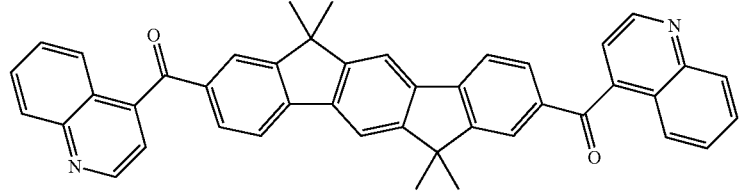 [SMILES: CC1(C)c2cc(C(=O)c3ccnc4ccccc34)ccc2-c2cc3c(cc21)-c1ccc(C(=O)c2ccnc4ccccc24)cc1C3(C)C] |
| 28 | 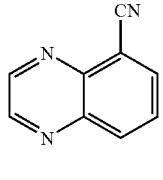 | 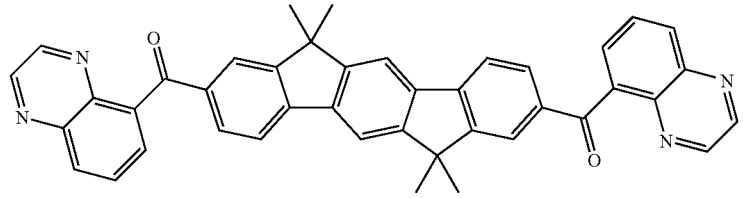 [SMILES: CC1(C)c2cc(C(=O)c3cccc4nccnc34)ccc2-c2cc3c(cc21)-c1ccc(C(=O)c2cccc4nccnc24)cc1C3(C)C] |
| 29 | 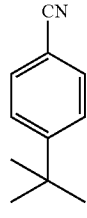 | 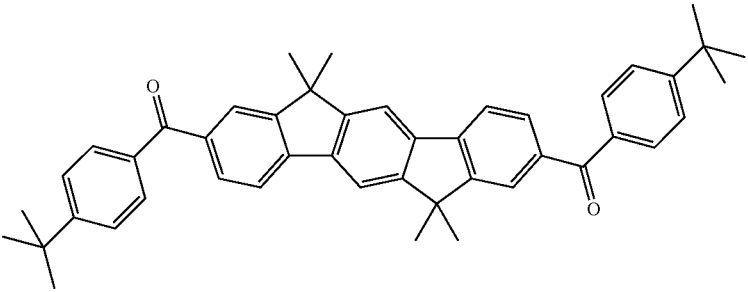 [SMILES: CC(C)(C)c1ccc(C(=O)c2ccc3c(c2)C(C)(C)c2cc4c(cc2-3)C(C)(C)c2cc(C(=O)c3ccc(C(C)(C)C)cc3)ccc2-4)cc1] |
| 30 |  | 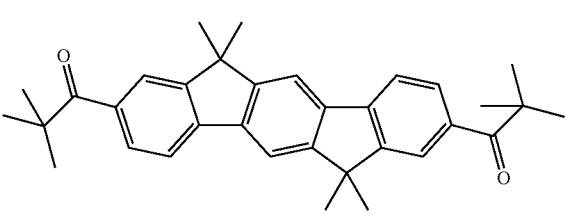 [SMILES: CC(C)(C)C(=O)c1ccc2c(c1)C(C)(C)c1cc3c(cc1-2)C(C)(C)c1cc(C(=O)C(C)(C)C)ccc1-3] |

Example 31

2,8-Bis(diphenylphosphinyl)(6,6,12,12-tetramethyl-6,12-dihydroindeno[1,2b]fluorene)

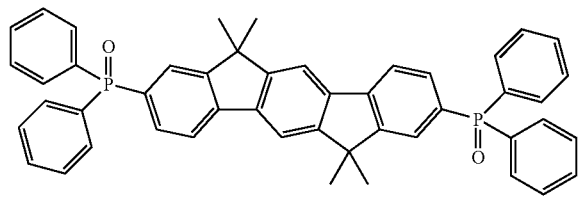 [SMILES: CC1(C)c2cc(P(=O)(c3ccccc3)c3ccccc3)ccc2-c2cc3c(cc21)-c1ccc(P(=O)(c2ccccc2)c2ccccc2)cc1C3(C)C]

84.0 ml (210 mmol) of n-butyllithium (2.5M in n-hexane) are added to a suspension, cooled to −78° C., of 46.8 g (100 mmol) of 2,8-dibromo-6,6,12,12-tetramethyl-6,12-dihydroindeno[1,2b]fluorene in 700 ml of THF. The mixture is allowed to warm slowly to 0° C. over the course of 2 h and stirred at 0° C. for a further 1 h, a mixture of 41.3 ml (230 mmol) of chlorodiphenylphosphine in 100 ml of THF is then added, and the mixture is stirred at room temperature for a further 16 h. After addition of 10 ml of ethanol, the solvent is stripped off in a full vacuum, the residue is dissolved in 500 ml of ethyl acetate, the organic phase is washed three times with 300 ml of water, a mixture of 22.2 ml (250 mmol) of hydrogen peroxide and 100 ml of water is then added dropwise with vigorous stirring, and the mixture is stirred at room temperature for 16 h. The precipitated solid is filtered off with suction, washed with ethanol, dried and recrystallised from chlorobenzene.

Sublimation at $p=1\times10^{-5}$ mbar, T=340° C. Yield: 46.0 g (65 mmol), 64.7% of theory; purity: 99.9% according to HPLC.

Example 32

Synthesis of Further indenofluorenephosphine oxides

The following products are prepared analogously to Example 31 in a purity of 99.9% according to HPLC:

| Ex. | Chlorophosphine | Product |
|---|---|---|
| 33 | | |
| 34 | | |
| 35 | | |

| Ex. | Chlorophosphine | Product |
|---|---|---|
| 36 | 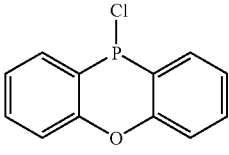 [SMILES: ClP1c2ccccc2Oc2ccccc21] | 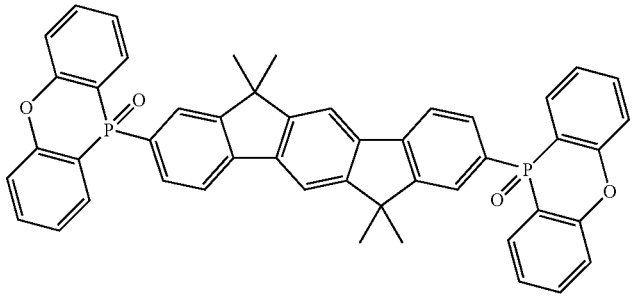 [SMILES: CC1(C)c2cc(P3(=O)c4ccccc4Oc4ccccc43)ccc2-c2cc3c(cc21)-c1ccc(P2(=O)c4ccccc4Oc4ccccc42)cc1C3(C)C] |

Example 37

3,9-Bis(diphenylamino)-5,11-dimethylindolo[3,2-b]carbazole

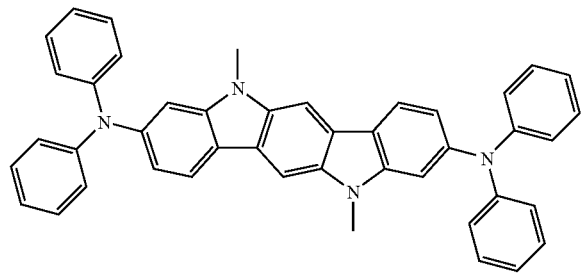 [SMILES: Cn1c2cc(N(c3ccccc3)c3ccccc3)ccc2c2cc3c(cc21)c1ccc(N(c2ccccc2)c2ccccc2)cc1n3C]

Preparation analogous to Example 1c. Instead of 2,8-dibromo-6,6,12,12-tetramethyl-6,12-dihydroindeno[1,2b]fluorene, 44.2 g (100 mmol) of 3,9-dibromo-5,11-dimethylindolo[2,3-b]carbazole are used. Recrystallisation from NMP. Sublimation $p=1\times10^{-5}$ mbar, T=350° C. Yield: 43.9 g (71 mmol), 70.9% of theory; purity: 99.8% according to HPLC.

Example 38

Synthesis of Further indolocarbazole Derivatives

The following products are prepared analogously to Example 37 in a purity of 99.9% according to HPLC:

| Ex. | Amine | Product |
|---|---|---|
| 39 | 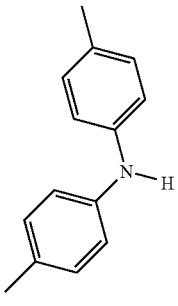 | 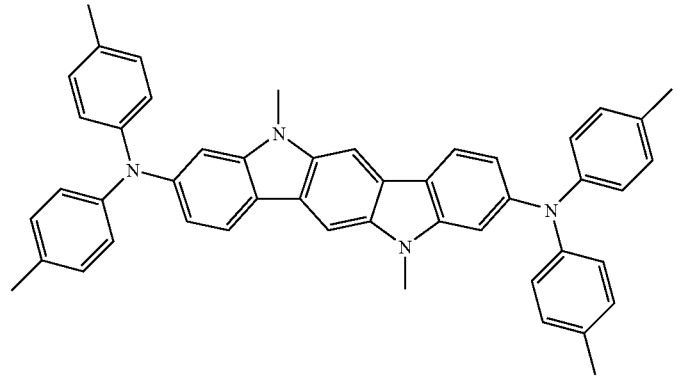 |
| 40 | 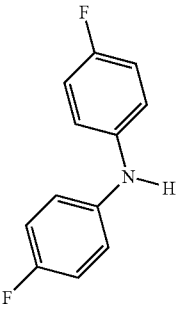 [SMILES: Fc1ccc(Nc2ccc(F)cc2)cc1] | 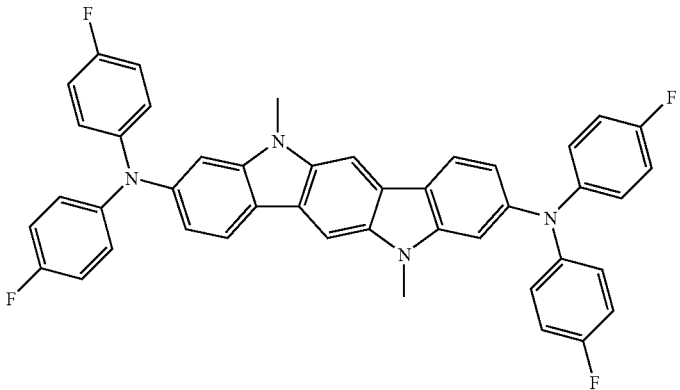 [SMILES: Cn1c2cc(N(c3ccc(F)cc3)c3ccc(F)cc3)ccc2c2cc3c(cc21)c1ccc(N(c2ccc(F)cc2)c2ccc(F)cc2)cc1n3C] |

-continued
| Ex. | Amine | Product |
|---|---|---|
| 41 | 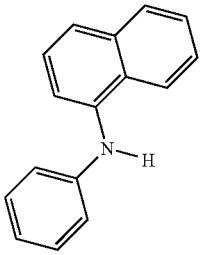 [SMILES: c1ccc(Nc2cccc3ccccc23)cc1] | 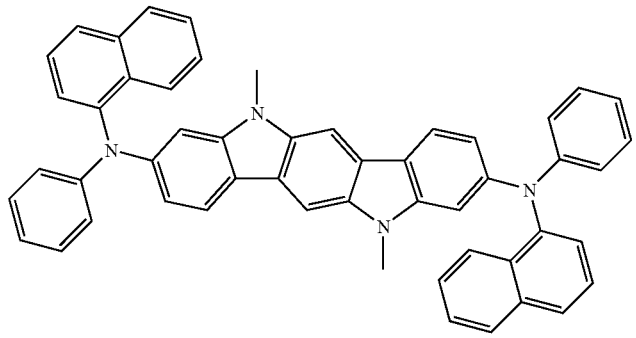 [SMILES: Cn1c2cc(N(c3ccccc3)c3cccc4ccccc34)ccc2c2cc3c(cc21)c1ccc(N(c2ccccc2)c2cccc4ccccc24)cc1n3C] |
| 42 | 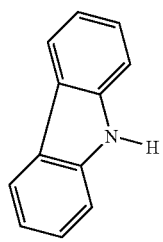 [SMILES: c1ccc2c(c1)[nH]c1ccccc12] | 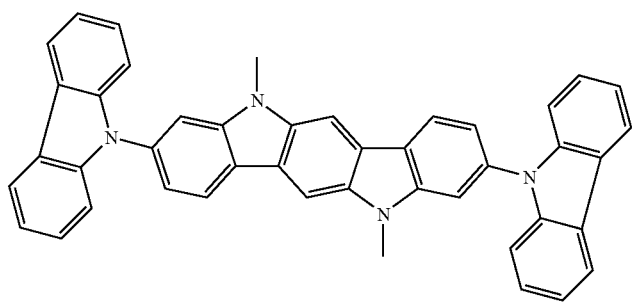 [SMILES: Cn1c2cc(-n3c4ccccc4c4ccccc43)ccc2c2cc3c(cc21)c1ccc(-n2c4ccccc4c4ccccc42)cc1n3C] |
| 43 | 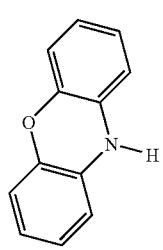 [SMILES: c1ccc2c(c1)Nc1ccccc1O2] | 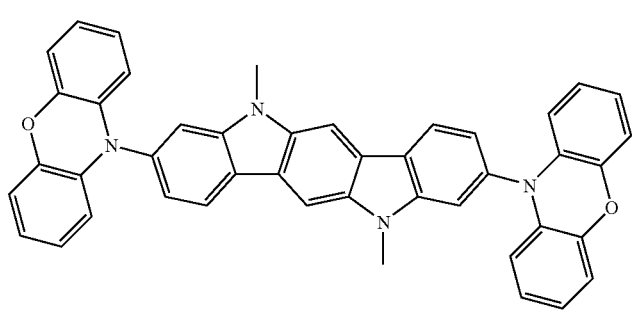 [SMILES: Cn1c2cc(N3c4ccccc4Oc4ccccc43)ccc2c2cc3c(cc21)c1ccc(N2c4ccccc4Oc4ccccc42)cc1n3C] |
| 44 | 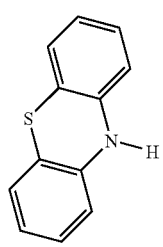 [SMILES: c1ccc2c(c1)Nc1ccccc1S2] | 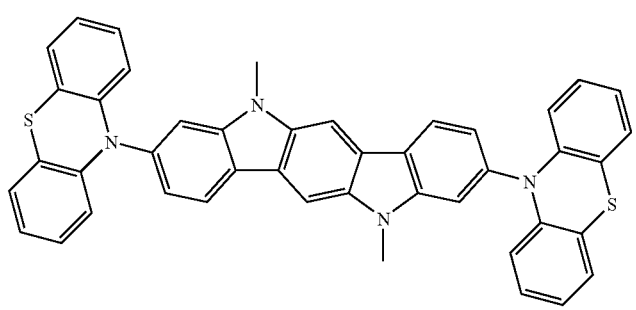 [SMILES: Cn1c2cc(N3c4ccccc4Sc4ccccc43)ccc2c2cc3c(cc21)c1ccc(N2c4ccccc4Sc4ccccc42)cc1n3C] |

Example 45

3,9-Bis(diphenylamino)5,11-diphenylphosphindolo-[3,2-b]dibenzophosphol a) 2',5'-Dibromo-4,4,4',4'-tetra-p-tolyl-[1,1',4,4]-terphenyl-4,4'-diamine

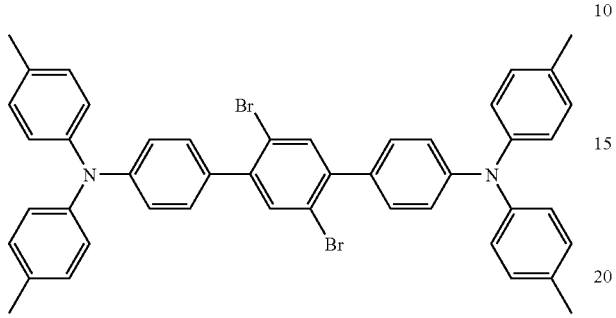

A suspension of 24.4 g (50 mmol) of 1,4-dibromo-2,5-diiodobenzene, 51.9 g (130 mmol) of 4-[4,4,5,-tetramethyl-1,3,2-dioxaborolan-2-yl]-di-p-tolylamine, 26.5 g (250 mmol) of sodium carbonate and 116 mg (0.1 mmol) of tetrakis(triphenylphosphino)palladium(0) in a mixture of 300 ml of toluene, 100 ml of dioxane and 300 ml of water is refluxed for 18 h. After cooling, 500 ml of ethanol are added to the reaction mixture, and the solid is filtered off with suction, washed three times with 200 ml of water each time and three times with 200 ml of ethanol each time, dried under reduced pressure and recrystallised from dioxane. Yield: 18.6 g (24 mmol), 47.7% of theory; purity: 97% according to NMR.

b) 3,9-Bis(diphenylamino)-5,11-diphenylphosphindolo[3,2-b]dibenzophosphol 5,11-oxide

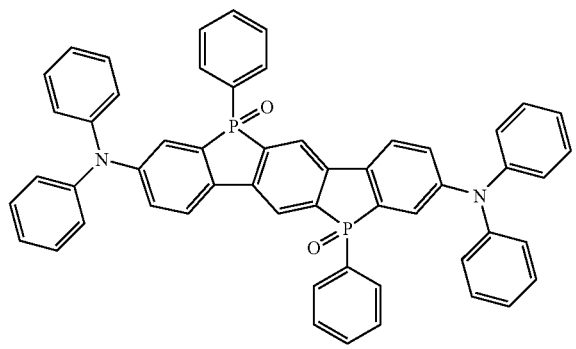 [SMILES: O=P1(c2ccccc2)c2cc(N(c3ccccc3)c3ccccc3)ccc2-c2cc3c(cc21)-c1ccc(N(c2ccccc2)c2ccccc2)cc1P3(=O)c1ccccc1]

16.8 ml (42 mmol) of n-butyllithium (2.5M in n-hexane) are added dropwise to a solution, cooled to −78° C., of 15.6 g (20 mmol) of 2',5'-dibromo-4,4,4',4'-tetra-p-tolyl-[1,1',4,4]-terphenyl-4,4'-diamine in 500 ml of THF, the mixture is stirred at −78° C. for a further 3 h, and a mixture of 6.2 ml (44 mmol) of phenylphosphonous dichloride and 50 ml of THF is added over the course of 1 min. After slow warming to room temperature, the solvent is removed fully under reduced pressure, the residue is taken up in 200 ml of 1,2-dichloroethane, 26.7 g (200 mmol) of anhydrous aluminium chloride are added, and the mixture is refluxed for 15 h. After cooling, 200 ml of 5N hydrochloric acid are added, the organic phase is separated off, washed once with 100 ml of 5N hydrochloric acid and five times with 300 ml of water each time and dried over magnesium sulfate, the solvent is removed under reduced pressure, and the product is recrystallised from NMP. Sublimation p=1×10$^{-5}$ mbar, T=360° C. Yield: 6.2 g (7.7 mmol), 38.3% of theory; purity: 99.8% according to HPLC, including all stereoisomers.

Example 46

Production of OLEDs Comprising indenofluorenediamines as Hole-Injection Material or Hole-Transport Material in Fluorescent OLEDs OLEDs are produced by a general process as described in WO 04/058911, which is adapted in individual cases to the respective circumstances (for example layer-thickness variation in order to achieve optimum efficiency or colour).

The results for various OLEDs are presented in Examples 47-62 below. The basic structure and the materials used (apart from the hole-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1) or or or or or: | B2 (compound according to Example 2) B1 (compound according to Example 1) B9 (compound according to Example 9) B15 (compound according to Example 15) B37 (compound according to Example 37) as comparative example 4,4',4''-tris(N-1-naphthyl-N-phenylamino)triphenylamine (abbreviated to NaphDATA, purchased from SynTec) |
| Hole-transport layer (HTM2) | 20 nm NPB (N-naphthyl-N-phenyl-4,4'-di-aminobiphenyl) |
| Emission layer (EML) | 30 nm doped layer of 9,10-bis(1-naphthyl-anthracene) as host material (abbreviated to H1), doped with 5% of tris[4-(2,2-di-phenylvinyl)phenyl]amine as dopant (abbreviated to D1, vapour-deposited, synthesised in accordance with WO 06/000388) |
| Electron conductor (ETC) | 20 nm AlQ$_3$ (purchased from SynTec, tris(quinolinato)aluminium(III)) |
| Cathode | 1 nm LiF, 150 nm Al on top. |

The OLEDs can also be produced without PEDOT as hole-injection layer. In these cases, the indenofluorenediamine derivative according to the invention is then the hole-injection compound. These OLEDs exhibit comparably good properties.

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 1 shows the results for some OLEDs (Examples 47 to 62) in which the layer thickness of the hole-transport layer (HTM1) is varied. The comparative material used in the comparative examples is NaphDATA.

The host material H1 is 9,10-bis(1-naphthyl)anthracene, and the dopant employed is D1. Both are shown below:

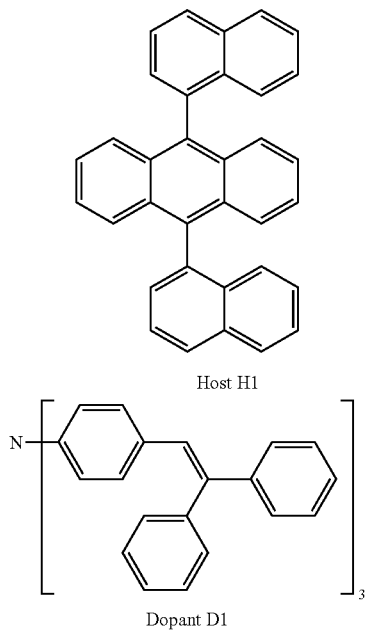

Host H1

Dopant D1

As can be seen from Examples 51 to 62 according to the invention in Table 1, OLEDs comprising the hole-transport material according to the invention (HTM1) exhibit a significantly lower operating voltage than with NaphDATA in accordance with the prior art as hole-transport material. The operating voltage is furthermore independent of the layer thickness of the hole-transport layer. This property is of major advantage for the construction of full-colour displays since the thickness of the pixels of the primary colours blue, green and red can be made the same by variation of the layer thickness of the hole-transport layer. The hole-transport material according to the invention can thus serve as thickness compensation layer here without adversely affecting the electro-optical properties of the device. As can be seen from the comparative examples, this is not the case for the hole-transport material (NaphDATA) in accordance with the prior art: here, a significantly higher operating voltage is required at a greater layer thickness of the hole-transport layer.

TABLE 1

| Example | HTL 1 or HIL | HTL 2 | Max. efficiency (cd/A) | Voltage (V) at 1000 cd/m² | CIE |
|---|---|---|---|---|---|
| Example 47 (comparison) | NaphDATA (20 nm) | NPB (20 nm) | 7.5 | 6.1 | x = 0.16 y = 0.25 |
| Example 48 (comparison) | NaphDATA (50 nm) | NPB (20 nm) | 7.2 | 6.0 | x = 0.16 y = 0.25 |
| Example 49 (comparison) | NaphDATA (100 nm) | NPB (20 nm) | 6.4 | 7.9 | x = 0.16 y = 0.24 |
| Example 50 (comparison) | NaphDATA (150 nm) | NPB (20 nm) | 5.7 | 8.4 | x = 0.16 y = 0.26 |
| Example 51 | B2 (20 nm) | NPB (20 nm) | 8.5 | 5.2 | x = 0.16 y = 0.25 |
| Example 52 | B2 (50 nm) | NPB (20 nm) | 8.6 | 5.3 | x = 0.16 y = 0.25 |
| Example 53 | B2 (100 nm) | NPB (20 nm) | 8.6 | 5.5 | x = 0.16 y = 0.24 |

TABLE 1-continued

| Example | HTL 1 or HIL | HTL 2 | Max. efficiency (cd/A) | Voltage (V) at 1000 cd/m² | CIE |
|---|---|---|---|---|---|
| Example 54 | B2 (150 nm) | NPB (20 nm) | 8.7 | 5.6 | x = 0.16 y = 0.26 |
| Example 55 | B1c (20 nm) | NPB (20 nm) | 8.2 | 5.4 | x = 0.16 y = 0.25 |
| Example 56 | B1c (100 nm) | NPB (20 nm) | 8.3 | 5.5 | x = 0.16 y = 0.24 |
| Example 57 | B9 (20 nm) | NPB (20 nm) | 8.2 | 6.1 | x = 0.16 y = 0.25 |
| Example 58 | B9 (100 nm) | NPB (20 nm) | 8.1 | 6.3 | x = 0.16 y = 0.24 |
| Example 59 | B15 (20 nm) | NPB (20 nm) | 8.8 | 5.6 | x = 0.16 y = 0.25 |
| Example 60 | B15 (100 nm) | NPB (20 nm) | 8.9 | 5.8 | x = 0.16 y = 0.24 |
| Example 61 | B37 (20 nm) | NPB (20 nm) | 7.9 | 6.3 | x = 0.16 y = 0.25 |
| Example 62 | B37 (100 nm) | NPB (20 nm) | 8.0 | 6.5 | x = 0.16 y = 0.24 |

Example 63

Production of OLEDs Comprising indenofluorenediamines as Hole-Injection Material or Hole-Transport Material in Phosphorescent OLEDs OLEDs are produced by a general process as described in WO 04/093207, which is adapted in individual cases to the respective circumstances (for example layer-thickness variation in order to achieve optimum efficiency or colour).

The results for various OLEDs are presented in Examples 64-68 below. The basic structure and the materials used (apart from the hole-transport layer) are identical in the examples for better comparability. OLEDs having the following structure are produced analogously to the above-mentioned general process:

| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1) or: | B2 (compound according to Example 2) as comparative example 4,4',4"-tris(N-1-naphthyl-N-phenylamino)triphenylamine (abbreviated to NaphDATA, purchased from SynTec) (comparative standard) |
| Hole-transport layer (HTM2) | 20 nm (vapour-deposited; S-TAD prepared in accordance with WO 99/12888; 2,2',7,7'-tetrakis(diphenylamino)spiro-bifluorene) |
| or: | 20 nm NPB (N-naphthyl-N-phenyl-4,4'-diaminobiphenyl) |
| Emission layer (EML) | 40 nm ketone 1 (bis(9,9'-spirobifluoren-2-yl) ketone (vapour-deposited, synthesised in accordance with WO 04/093207), doped with 15% of triplet emitter E1 (synthesised in accordance with WO 04/085449) |
| AlQ₃ | 20 nm (vapour-deposited; AlQ₃ purchased from SynTec; tris(quinolinolato)aluminium-(III)) |
| Cathode | 1 nm LiF, 150 nm Al on top. |

The OLEDs can also be produced without PEDOT as hole-injection layer. In these cases, the indenofluorenediamine derivative according to the invention is then the hole-injection compound. These OLEDs exhibit comparably good properties.

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 2 shows the results for some OLEDs (Examples 64 to 68) in which the layer thickness of the hole-transport layer (HTM1) is varied. The comparative material used in the comparative examples is NaphDATA.

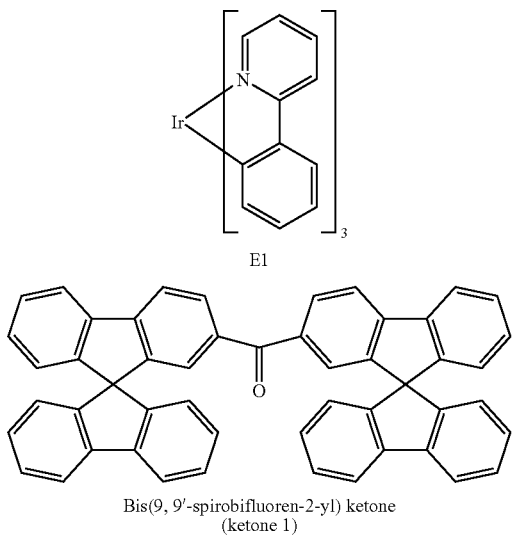

Bis(9, 9'-spirobifluoren-2-yl) ketone
(ketone 1)

As can be seen from Examples 65 to 68 according to the invention in Table 2, OLEDs comprising the hole-transport material according to the invention (HTM1) exhibit a significantly lower operating voltage and higher efficiency than with NaphDATA in accordance with the prior art as hole-transport material. The operating voltage is furthermore independent of the layer thickness of the hole-transport layer. The hole-transport material according to the invention can thus serve as thickness compensation layer here without adversely affecting the electro-optical properties of the device.

TABLE 2

| Example | HTL 1 or HIL | HTL 2 | Max. efficiency (cd/A) | Voltage (V) at 1000 cd/m$^2$ | CIE |
|---|---|---|---|---|---|
| Example 64 (comparison) | NaphDATA (20 nm) | S-TAD (20 nm) | 33 | 4.5 | x = 0.38 y = 0.58 |
| Example 65 | B2 (20 nm) | S-TAD (20 nm) | 42 | 3.8 | x = 0.38 y = 0.58 |
| Example 66 | B2 (150 nm) | S-TAD (20 nm) | 40 | 3.9 | x = 0.36 y = 0.60 |
| Example 67 | B2 (20 nm) | NPB (20 nm) | 37 | 4.2 | x = 0.38 y = 0.58 |
| Example 68 | B2 (150 nm) | NPB (20 nm) | 35 | 4.3 | x = 0.36 y = 0.60 |

Example 69

Production of OLEDs Comprising indenofluorene ketones or indenofluorenephosphine oxides as Electron-Transport Material in Phosphorescent OLEDs OLEDs are produced by a general process as described in WO 04/093207, which is adapted in individual cases to the respective circumstances (for example layer-thickness variation in order to achieve optimum efficiency or colour).

The results for various OLEDs are presented in Examples 70-73 below. The basic structure and the materials used (apart from the electron-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1) | 20 nm 4,4',4''-tris(N-1-naphthyl-N-phenyl-amino)triphenylamine (abbreviated to NaphDATA, purchased from SynTec) |
| Hole-transport layer (HTM2) | 20 nm S-TAD (vapour-deposited; S-TAD prepared in accordance with WO 99/12888; 2,2',7,7'-tetrakis(diphenyl-amino)spirobifluorene) |
| Emission layer (EML) | 40 nm ketone 1 (bis(9,9'-spirobifluoren-2-yl) ketone (vapour-deposited, synthesised in accordance with WO 04/093207), doped with 15% of triplet emitter E1 (synthesised in accordance with WO 04/085449) |
| Electron-transport layer | 20 nm B19 (compound according to Example 19) |
| or | 20 nm B26 (compound according to Example 26) |
| or | 20 nm B31 (compound according to Example 31) |
| or | 20 nm AlQ$_3$ (AlQ$_3$ purchased from SynTec; tris(quinolinolato)aluminium(III), comparison) |
| Cathode | 1 nm LiF, 150 nm Al on top. |

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 3 shows the results for some OLEDs (Examples 70 to 73) in which the electron-transport layer (ETL) is varied. The comparative material used in the comparative examples is Alq. The emitter E1 and the matrix material ketone 1 are shown in Example 63.

As can be seen from Examples 71 to 73 according to the invention in Table 3, OLEDs comprising the electron-transport material according to the invention exhibit a lower operating voltage and higher efficiency than with Alq in accordance with the prior art.

TABLE 3

| Example | ETL | Max. efficiency (cd/A) | Voltage (V) at 1000 cd/m$^2$ | CIE |
|---|---|---|---|---|
| Example 70 (comparison) | Alq (20 nm) | 33 | 4.5 | x = 0.38; y = 0.58 |
| Example 71 | B19 (20 nm) | 35 | 4.2 | x = 0.38; y = 0.58 |

TABLE 3-continued

| Example | ETL | Max. efficiency (cd/A) | Voltage (V) at 1000 cd/m² | CIE |
|---|---|---|---|---|
| Example 72 | B26 (20 nm) | 38 | 3.9 | x = 0.38; y = 0.58 |
| Example 73 | B31 (20 nm) | 37 | 4.1 | x = 0.38; y = 0.58 |

Example 74

Production of red-phosphorescent OLEDs Comprising indenofluorene ketones or indenofluorenephosphine oxides as Triplet Matrix Material OLEDs are produced by a general process as described in WO 04/093207, which is adapted in individual cases to the respective circumstances (for example layer-thickness variation in order to achieve optimum efficiency or colour).

The results for various OLEDs are presented in Examples 75-78 below. The basic structure and the materials used (apart from the electron-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1) | 20 nm 4,4',4"-tris(N-1-naphthyl-N-phenyl-amino)triphenylamine (abbreviated to NaphDATA, purchased from SynTec) |
| Hole-transport layer (HTM2) | 20 nm S-TAD (vapour-deposited; S-TAD prepared in accordance with WO 99/12888; 2,2',7,7'-tetrakis(diphenyl-amino)spirobifluorene) |
| Emission layer (EML) | 20 nm B19 (compound according to Example 26) |
| or | 20 nm B26 (compound according to Example 31) |
| or | 20 nm B31 (compound according to Example 31) |
| or | ketone 1 (bis(9,9'-spirobifluoren-2-yl) ketone (vapour-deposited, synthesised in accordance with WO 04/093207) (comparative standard), in each case doped with 10% of triplet emitter E2 (synthesised in accordance with WO 05/033244) |
| Electron-transport layer | 20 nm AlQ₃ (vapour-deposited: AlQ₃ purchased from SynTec; tris(quinolinolato)aluminium(III)) |
| Cathode | 1 nm LiF, 150 nm Al on top. |

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 4 shows the results for some OLEDs (Examples 75 to 78) in which the triplet matrix material of the emission layer (EML) is varied. The comparative material used in the comparative examples is ketone 1.

The emitter E1 and the triplet matrix material ketone 1 are shown below for clarity:

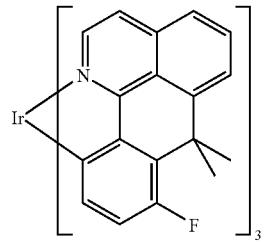

E2

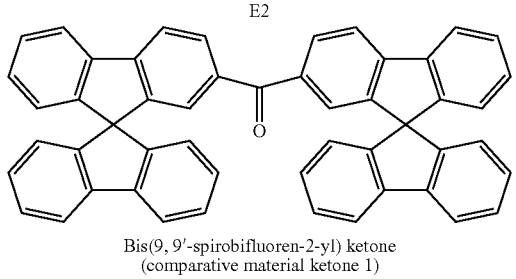

Bis(9, 9'-spirobifluoren-2-yl) ketone
(comparative material ketone 1)

As can be seen from Examples 76 to 78 according to the invention in Table 4, OLEDs comprising the electron-transport material according to the invention exhibit a lower operating voltage and higher efficiency than with ketone 1 in accordance with the prior art.

TABLE 4

| Example | EML host:emitter | Max. efficiency (cd/A) | Voltage (V) at 1000 cd/m² | CIE |
|---|---|---|---|---|
| Example 75 (comparison) | E2:ketone 1 (40 nm) | 13.3 | 5.5 | x = 0.65; y = 0.35 |
| Example 76 | E2:B19 (40 nm) | 15.4 | 5.2 | x = 0.65; y = 0.35 |
| Example 77 | E2:B26 (40 nm) | 14.8 | 5.4 | x = 0.65; y = 0.35 |
| Example 78 | E2:B31 (40 nm) | 14.5 | 5.1 | x = 0.65; y = 0.35 |

Example 79

Production of OLEDs comprising indenofluorenediamines as Emitter

OLEDs are produced by a general process as described in WO 10 04/058911, which is adapted in individual cases to the respective circumstances (for example layer-thickness variation in order to achieve optimum efficiency or colour).

The results for various OLEDs are presented in Examples 80-86 below. The basic structure and the materials used (apart from the emitting layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1) | 20 nm B2 (compound according to Example 2) |

| | |
|---|---|
| Hole-transport layer (HTM2) | 20 nm NPB (N-naphthyl-N-phenyl-4,4′-diaminobiphenyl) |
| Emission layer (EML) | 30 nm layer of H1, H2 or H3 as host material doped with x % (see table) of B2 (compound according to Example 2) or B17 (compound according to Example 17) as dopant |
| Electron conductor (ETC) | 20 nm (vapour-deposited; AlQ$_3$ purchased from SynTec, tris(quinolinolato)aluminium-(III)) |
| Cathode | 1 nm LiF, 150 nm Al on top. |

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 5 shows the results for some OLEDs (Examples 80 to 86) in which B2 (compound according to Example 2) or B17 (compound according to Example 17) is used as dark-blue emitter and its degree of doping is varied.

The host materials H1, H2 and H3 are shown below:

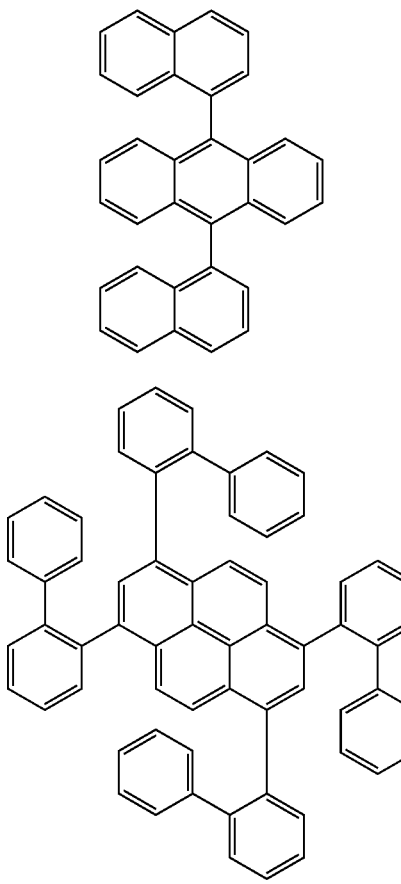

Host H1

Host H2

Host H3

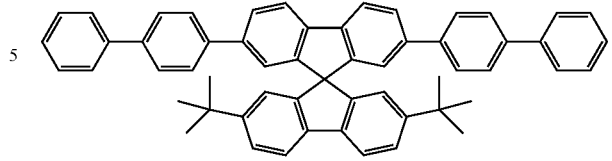

As can be seen from Examples 80 to 86 in Table 5, OLEDs comprising the dopants B2 (compound according to Example 2) and B17 (compound according to Example 17) according to the invention exhibit efficient dark-blue emission. By contrast, colour coordinates of only (0.15; 0.15) are achieved with commercial OLEDs. The internal quantum efficiency is close to 100%.

TABLE 5

| Example | EML | Max. efficiency (cd/A) | Voltage (V) at 1000 cd/m$^2$ | CIE |
|---|---|---|---|---|
| Example 80 | H2 2% of B2 | 2.5 | 6.6 | x = 0.16 y = 0.09 |
| Example 81 | H2 5% of B2 | 2.8 | 6.4 | x = 0.16 y = 0.10 |
| Example 82 | H2 10% of B2 | 2.7 | 6.3 | x = 0.16 y = 0.13 |
| Example 83 | H3 5% of B2 | 2.3 | 6.8 | x = 0.16 y = 0.04 |
| Example 84 | H3 10% of B2 | 2.2 | 6.5 | x = 0.16 y = 0.05 |
| Example 85 | H3 15% of B2 | 2.0 | 6.3 | x = 0.16 y = 0.05 |
| Example 86 | H1 10% of B17 | 2.4 | 6.2 | x = 0.16 y = 0.08 |

Example 87

Bis(N-(4-tert-butylphenyl)-N-(4-bromophenyl)amino)-6,6,12,12-tetraoctyl-6,12,dihydroindeno[1,2b]fluorene a) Bis(N-(4-tert-butylphenyl)-N-phenylamino)-6,6,12,12-tetraoctyl-6,12-dihydroindeno[1,2b]fluorene

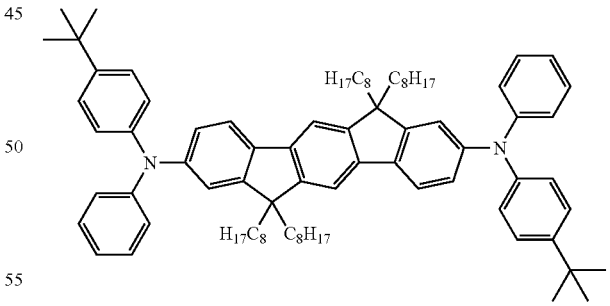

A solution of 17.2 g (20.0 mmol) of 6,6,12,12-tetraoctyl-6,12-dihydro -[1,2b]indenofluorene dibromide and 10.0 g (44.4 mmol) of 4-tert-butylphenylphenylamine in 130 ml of dry toluene is saturated with argon. 81.0 mg of tri-tert-butylphosphine, 45 mg of palladium acetate and 5.97 g of sodium tert-butoxide are then added. The reaction mixture is refluxed for 12.5 h. After cooling to RT, the mixture is extracted with 2M HCl (2×100 ml). The organic phase is separated off, filtered through Celite and evaporated in a rotary evaporator. The crude product is recrystallised from EtOH/toluene, giving 18.6 g (81%) of yellow crystals.

b) Bis(N-(4-tert-butylphenyl)-N-(4-bromophenyl)amino)-,6,12,12-tetraoctyl-6,12,dihydroindeno[1,2b]fluorene

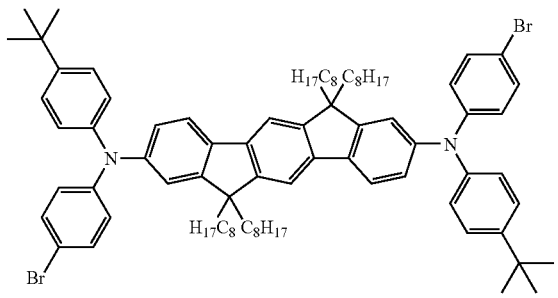

5.0 g (3.8 mmol) of bis(N-(4-tert-butylphenyl)-N-phenylamino)-6,6,12,12-tetraoctyl-6,12,dihydroindeno[1,2b]fluorene are dissolved in 22.4 ml of dry THF, and a solution of 1.5 g of NBS in 22.4 ml of THF is added dropwise at 0° C. The reaction mixture is allowed to come to RT, and the solvent is removed. The solid is washed by boiling with ethanol and filtered off with suction. After drying under reduced pressure, the crude product is recrystallised from acetonitrile/toluene, giving 2.16 g (43%) of pale-yellow crystals.

Bis(N-(4-tert-butylphenyl)-N-(4-bromophenyl)amino)-6,6,12,12-tetraoctyl-6,12,dihydroindeno[1,2b]fluorene can be employed as monomer for polymerisation, for example for Suzuki or Yamamoto polymerisation. This compound is particularly suitable for incorporation into conjugated or partially conjugated polymers and is particularly suitable as hole-conducting compound in these polymers.

Example 88

2,10-Bis(diphenylamino)-12,15-dihydro-6,6,12,12,15,15-hexamethyl-6H-diindeno[1,2-b:2',1'-h]fluorene a) 12,15-Dihydro-6,6,12,12,15,15-hexamethyl6H-diindeno-[1,2-b:2',1'-h]fluorene

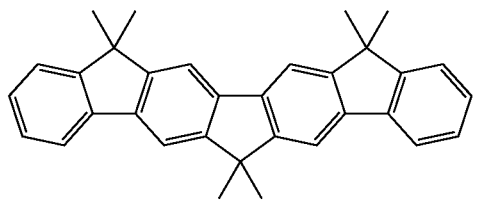 [SMILES: CC1(C)c2ccccc2-c2cc3c(cc21)-c1cc2c(cc1C3(C)C)-c1ccccc1C2(C)C]

The preparation is carried out analogously to the preparation of 9,9-dimethylfluorene from 12,15-dihydro-6H-diindeno[1,2-b:2',1'-h]fluorene (Stauner et al., *Helv. Chim. Acta* 1970, 53(6), 131 1), dimethyl sulfate and sodium hydroxide solution in accordance with JP 08113542. Yield 61.0% of theory; purity 97% according to $^1$H-NMR.

b) 2,10-Dibromo-12,15-dihydro-6,6,12,12,15,15-hexamethyl-6H-diindeno[1,2-b:2',1'-h]fluorene

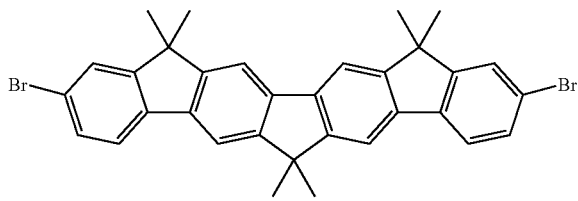 [SMILES: CC1(C)c2cc(Br)ccc2-c2cc3c(cc21)-c1cc2c(cc1C3(C)C)-c1ccc(Br)cc1C2(C)C]

Preparation analogous to Example 1b. Instead of 122.0 g (393 mmol) of 6,6,12,12-tetramethyl-6,12-dihydroindeno[1,2b]fluorene, 167.7 g (393 mmol) of 12,15-dihydro-6,6,12,12,15,15-hexamethyl-6H-diindeno-[1,2-b:2',1'-h]fluorene are employed. Yield: 198.5 g (339 mmol), 86.4% of theory; purity: 98% according to $^1$H-NMR.

c) 2,10-Bis(diphenylamino)-12,15-dihydro-6,6,12,12,15,15-hexamethyl-6H-diindeno[1,2-b:2',1'-h]fluorene

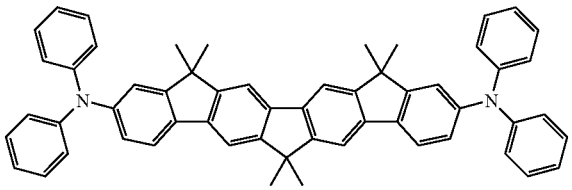 [SMILES: CC1(C)c2cc(N(c3ccccc3)c3ccccc3)ccc2-c2cc3c(cc21)-c1cc2c(cc1C3(C)C)-c1ccc(N(c3ccccc3)c3ccccc3)cc1C2(C)C]

Preparation analogous to Example 1c. Instead of 46.8 g (100 mmol) of 2,8-dibromo-6,6,12,12-tetramethyl-6,12-dihydroindeno[1,2b]fluorene, 58.4 g (100 mmol) of 2,10-dibromo-12,15-dihydro-6,6,12,12,15,15-hexamethyl-6H-diindeno[1,2-b:2',1'-h]fluorene are used. Sublimation p=1×10$^{-5}$ mbar, T=390° C. Yield: 55.0 g (72 mmol), 72.3% of theory; purity: 99.9% according to HPLC.

Example 89

2,8-Bis(bis(4-diphenylaminophenyl)amino)-6,6,12,12-tetramethyl-6,12-dihydroindeno[1,2b]fluorene a) 2,8-Bis(bis(4-bromphenyl)amino)-6,6,12,12-tetramethyl-6,12-dihydroindeno[1,2b]fluorene

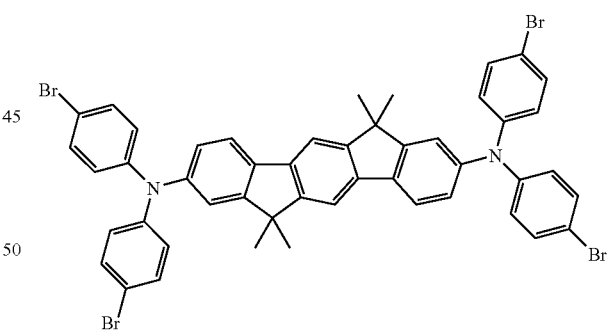

74.8 g (420 mmol) of N-bromosuccinimide are added in portions with vigorous stirring to a solution of 64.5 g (100 mmol) of 2,8-bis(diphenyl-amino)-6,6,12,12tetramethyl-6,12-dihydroindeno[1,2b]fluorene in 1500 ml of dichloromethane, and the mixture is stirred at room temperature for 16 h. The reaction mixture is concentrated to a volume of 200 ml under reduced pressure, 1000 ml of ethanol are added, the precipitate is filtered off with suction, stirred with 1000 ml of hot ethanol, filtered off with suction, washed three times with 300 ml of ethanol each time and dried under reduced pressure. Yield: 82.1 g (85 mmol), 85.5% of theory; purity: 97% according to $^1$H-NMR.

b) 2,8-Bis(bis(4-diphenylaminophenyl)amino)-6,6,12,12-tetramethyl-6,12-dihydroindeno[1,2b]fluorene

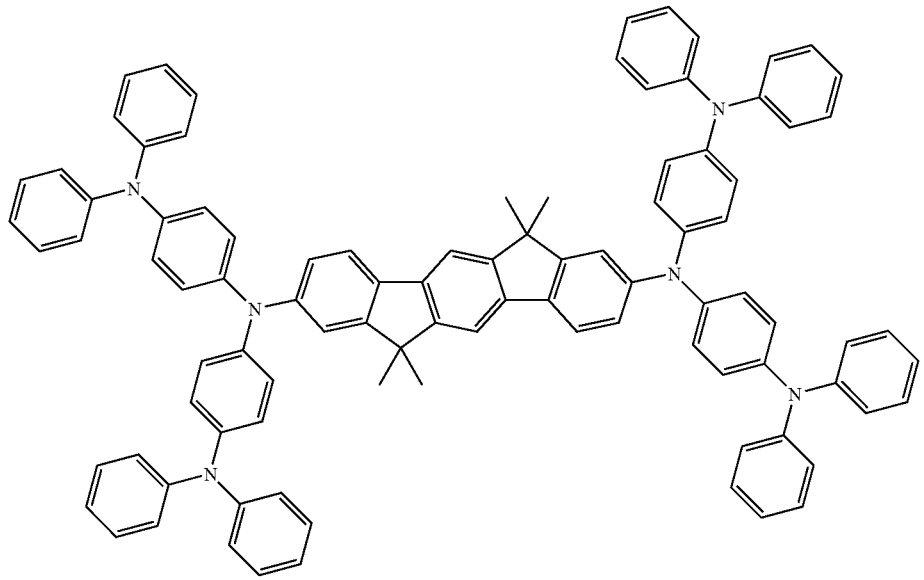 [SMILES: CC1(C)c2cc(N(c3ccc(N(c4ccccc4)c4ccccc4)cc3)c3ccc(N(c4ccccc4)c4ccccc4)cc3)ccc2-c2cc3c(cc21)-c1ccc(N(c2ccc(N(c4ccccc4)c4ccccc4)cc2)c2ccc(N(c4ccccc4)c4ccccc4)cc2)cc1C3(C)C]

Procedure analogous to Example 1c. Instead of 46.8 g (100 mmol) of 2,8-dibromo-6,6,12,12-tetramethyl-6,12-dihydroindeno[1,2b]fluorene, 48.0 g (50 mmol) of 2,8-bis(bis(4-bromophenyl)amino)-6,6,12,12-tetramethyl-6,12-dihydroindeno[1,2b]fluorene are employed. Recrystallisation from dioxane; sublimation p=1×10$^{-5}$ mbar, T=380° C. Yield: 48.8 g (37 mmol), 74.3% of theory; purity: 99.8% according to HPLC.

Example 90

2,8-Bis((4-methylphenyl)(4-diphenylaminophenyl)-amino)-6,6,12,12-tetramethyl-6,12-dihydroindeno[1,2b]fluorene a) 2,8-Bis((4-bromophenyl)(4-methylphenyl)amino)-6,6,12,12-tetramethyl-6,12-dihydroindeno[1,2b]fluorene

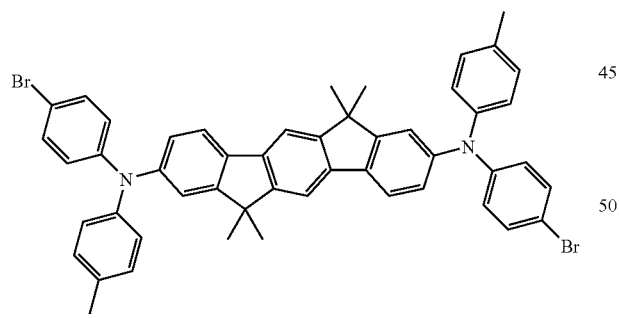

74.8 g (420 mmol) of N-bromosuccinimide are added in portions with vigorous stirring to a solution of 134.6 g (200 mmol) of 2,8-bis((phenyl)(4-methylphenyl)amino)-6,6,12,12-tetramethyl-6,12-dihydroindeno[1,2b]-fluorene (preparation analogous to Example 1c) in 1500 ml of dichloromethane, and the mixture is stirred at room temperature for 16 h. The reaction mixture is concentrated to a volume of 200 ml under reduced pressure, 1000 ml of ethanol are added, the precipitate is filtered off with suction, stirred with 1000 ml of hot ethanol, filtered off with suction, washed three times with 300 ml of ethanol each time and dried under reduced pressure. Yield: 139.0 g (167 mmol), 83.6% of theory; purity: 98% according to $^1$H-NMR.

b) 2,8-Bis((4-methylphenyl)(4-diphenylaminophenyl)amino)-6,6,12,12-tetramethyl-6,12-dihydroindeno[1,2b]fluorene

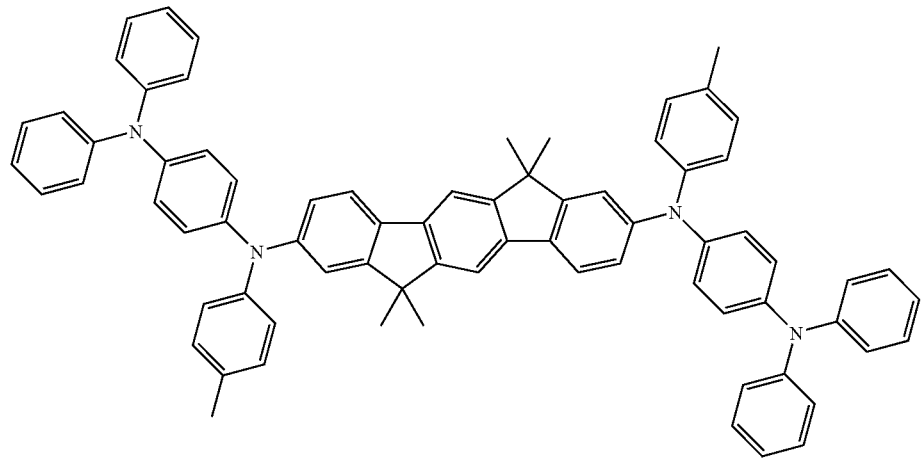 [SMILES: Cc1ccc(N(c2ccc(N(c3ccccc3)c3ccccc3)cc2)c2ccc3c(c2)C(C)(C)c2cc4c(cc2-3)C(C)(C)c2cc(N(c3ccc(C)cc3)c3ccc(N(c5ccccc5)c5ccccc5)cc3)ccc2-4)cc1]

Procedure analogous to Example 1c. Instead of 46.8 g (100 mmol) of 2,8-dibromo-6,6,12,12-tetramethyl-6,12-dihydroindeno[1,2b]fluorene, 83.1 g (100 mmol) of 2,8-bis((4-bromophenyl)(4-methylphenyl)amino)-6,6,12,12-tetramethyl-6,12-dihydroindeno[1,2b]fluorene are employed. Recrystallisation from NMP; sublimation $p=1\times10^{-5}$ mbar, $T=370°$ C. Yield: 83.6 g (83 mmol), 82.9% of theory; purity: 99.7% according to HPLC.

Example 91

Production of OLEDs Comprising indenofluorenetetramines or -hexamines as Hole-Injection Material or Hole-Transport Material in Fluorescent OLEDs OLEDs are produced by a general process as described in WO 04/1058911, which is adapted in individual cases to the respective circumstances (for example layer-thickness variation in order to achieve optimum efficiency or colour).

The results for various OLEDs are presented in Examples 92-94 below. The basic structure and the materials used (apart from the hole-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTM1)or or | B89 (compound according to Example 89) B90 (compound according to Example 90) as comparative example 4,4',4''-tris(N-1-naphthyl-N-phenylamino)triphenylamine (abbreviated to NaphDATA, purchased SynTec) |
| Hole-transport layer (HTM2) | 20 nm NPB (N-naphthyl-N-phenyl-4,4'-diaminobiphenyl) |
| Emission layer (EML) | 30 nm doped layer of 9,10-bis(1-naphthyl-anthracene) as host material (abbreviated to H1), doped with 5% of tris[4-(2,2-diphenylvinyl)phenyl]amine as dopant (abbreviated to D1, vapour-deposited, synthesised as described in WO 06/000388) |
| Electron conductor (ETC) | 20 nm AlQ$_3$ (purchased from SynTec, tris(quinolinato)aluminium(III)) |
| Cathode | 1 nm LiF, 150 nm Al on top. |

The OLEDs can likewise be produced without PEDOT as hole-injection layer. In these cases, the indenofluorenetetramine or -hexamine derivative according to the invention is then the hole-injection compound. These OLEDs exhibit comparably good properties.

These OLEDs are characterised by standard methods; for this purpose, the electroluminescence spectra, the efficiency (measured in cd/A) and the power efficiency (measured in lm/W) are determined as a function of the brightness, calculated from current/voltage/brightness characteristic lines (IUL characteristic lines).

Table 6 shows the results for some OLEDs (Examples 92 to 94), in which the layer thickness of the hole-transport layer (HTM1) is varied. The comparative material used in the comparative examples is NaphDATA.

The host material H1 employed is 9,10-bis(1-naphthyl)anthracene, the dopant employed is D1. Both are shown below:

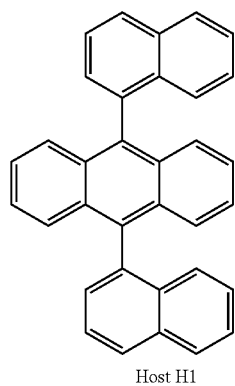

Host H1

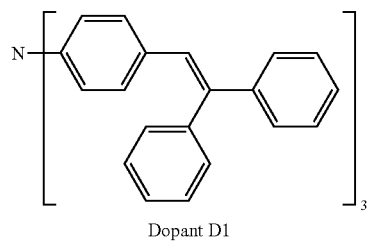

Dopant D1

As can be seen from Examples 92 and 93 according to the invention in Table 6, OLEDs comprising the hole-transport material according to the invention (HTM1) exhibit significantly greater efficiency than with NaphDATA in accordance with the prior art as hole-transport material. The operating voltage is furthermore independent of the layer thickness of the hole-transport layer. This property is of major advantage for the construction of full-colour displays since the thickness of the pixels of the primary colours blue, green and red can be made the same by variation of the layer thickness of the hole-transport layer. The hole-transport material according to the invention can thus serve as thickness compensation layer here without adversely affecting the electro-optical properties of the device. As can be seen from the comparative examples, this is not the case for hole-transport material (NaphDATA) in accordance with the prior art: here, a significantly higher operating voltage is required at a greater layer thickness of the hole-transport layer.

TABLE 6

| Example | HTL 1 or HIL | HTL 2 | Max. efficiency (cd/A) | Voltage (V) at 1000 cd/m² | CIE |
|---|---|---|---|---|---|
| Example 92 | B89 (20 nm) | NPB (20 nm) | 8.9 | 5.4 | x = 0.16 y = 0.25 |
| Example 93 | B90 (20 nm) | NPB (20 nm) | 9.0 | 5.5 | x = 0.16 y = 0.25 |
| Example 94 (comparison) | NaphDATA (20 nm) | NPB (20 nm) | 7.5 | 6.1 | x = 0.16 y = 0.25 |

The invention claimed is:

1. A compound of the formula (1)

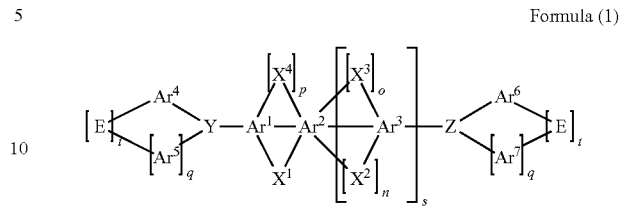

Formula (1)

wherein

Y and Z are, identically or differently, N, P, P=O, $PF_2$, P=S, As, As=O, As=S, Sb, Sb=O, Sb=S, C=O, O, S, Se, Te, S=O, $SO_2$, Se=O, $SeO_2$, Te=O or $TeO_2$;

$Ar^1$, $Ar^2$ and $Ar^3$ are on each occurrence, identically or differently, a benzene, or pyridine;

$Ar^4$, $Ar^5$, $Ar^6$ and $Ar^7$ are on each occurrence, identically or differently, an aromatic or heteroaromatic ring system having 5 to 40 aromatic ring atoms, which are optionally substituted by one or more radicals $R^1$;

E is on each occurrence, identically or differently, a single bond, $N(R^1)$, O,S, $C(R^1)_2$, $Si(R^1)_2$ or $B(R^1)$;

$R^1$ is on each occurrence, identically or differently, H, F, CN, $NO_2$, $Si(R^2)_3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by —$R^2C=CR^2$—, —C≡C—, $Si(R^2)_2$, $Ge(R^2)_2$, $Sn(R^2)_2$, C=O, C=S, C=Se, C=$NR^2$, —O—, —S—, —COO— or —$CONR^2$— and where one or more H atoms is optionally replaced by F, Cl, Br, I, CN or $NO_2$, or an aromatic or heteroaromatic ring system having 5 to 40 aromatic ring atoms, which is optionally substituted by one or more non-aromatic radicals $R^1$, or an aryloxy or heteroaryloxy group having 5 to 40 aromatic ring atoms, which is optionally substituted by one or more non-aromatic radicals $R^1$, or a combination of these systems; two or more substituents $R^1$ optionally form a mono- or polycyclic ring system with one another;

$R^2$ is on each occurrence, identically or differently, H or an aliphatic or aromatic hydrocarbon radical having 1 to 20 C atoms;

$X^1$ and $X^4$ are on each occurrence, identically or differently, a bridge which, with $Ar^1$ and $Ar^2$, defines a cyclic system selected from $C(R^1)_2$, $Si(R^1)_2$, C=O, C=$NR^1$, C=$C(R^1)_2$, O,S, S=O, $SO_2$, $N(R^1)$, $P(R^1)$, P(=O)$R^1$, P(=S)$R^1$, $B(R^1)$ or a combination of two, three or four of these groups;

$X^2$ and $X^3$ are on each occurrence, identically or differently, a bridge which, with $Ar^2$ and $Ar^3$, defines a cyclic ring system selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$, P(=O)$R^1$, P(=S)$R^1$ or a combination of two, three or four of these groups;

p=0;

one of the two indices n and o is equal to 1, and the other of the two indices n and o is equal to 0;

q and r are on each occurrence 1 if the corresponding central atom of the group Y or Z is an element from the $5^{th}$ main group and on each occurrence are equal to 0 if the corresponding central atom of the group Y or Z is an element from the 4th or 6th main group;

s is 1, 2 or 3; and t is on each occurrence, identically or differently, 0 or 1, where t=0 means that $R^1$ radicals are bonded instead of the group E; furthermore, t=0 if q=0 and t=0, if r=0.

2. The compound according to claim 1, wherein Y and Z, identically or differently, stand for nitrogen, C=O, phosphorus or P=O.

3. The compound according to claim 1, wherein $Ar^1$, $Ar^2$ and $Ar^3$, on each occurrence, stand for benzene.

4. The compound according to claim 3, wherein the compound of formula (1) is a compound of the formula (1a)

Formula (1a)

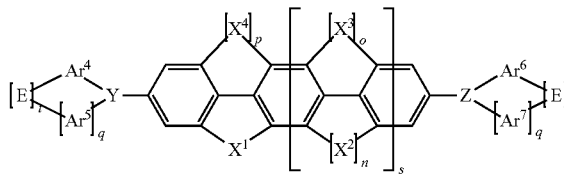

wherein

Y and Z are, identically or differently, N, P, P=O, $PF_2$, P=S, As, As=O, As=S, Sb, Sb=O Sb=S, C=O, O, S, Se, Te, S=O, $SO_2$, Se=O, $SeO_2$, Te=O or $TeO_2$;

$Ar^4$, $Ar^5$, $Ar^6$ and $Ar^7$ are on each occurrence, identically or differently, an aromatic or heteroaromatic ring system having 5 to 40 aromatic ring atoms, which are optionally substituted by one or more radicals $R^1$;

E is on each occurrence, identically or differently, a single bond, $N(R^1)$, O, S, $C(R^1)_2$, $Si(R^1)_2$ or $B(R^1)$;

$R^1$ is on each occurrence, identically or differently, H, F, CN, $NO_2$, $Si(R^2)_3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by —$R^2$C=$CR^2$—, —C≡C—, $Si(R^2)_2$, $Ge(R^2)_2$, $Sn(R^2)_2$, C=O, C=S, C=Se, C=$NR^2$, —O—, —S—, —COO— or —$CONR^2$— and where one or more H atoms is optionally replaced by F, Cl, Br, I, CN or $NO_2$, or an aromatic or heteroaromatic ring system having 5 to 40 aromatic ring atoms, which is optionally substituted by one or more non-aromatic radicals $R^1$, or an aryloxy or heteroaryloxy group having 5 to 40 aromatic ring atoms, which is optionally substituted by one or more non-aromatic radicals $R^1$, or a combination of these systems; two or more substituents $R^1$ optionally form a mono- or polycyclic ring system with one another;

$R^2$ is on each occurrence, identically or differently, H or an aliphatic or aromatic hydrocarbon radical having 1 to 20 C atoms;

$X^1$ and $X^4$ are on each occurrence, identically or differently, a bridge which, with $Ar^1$ and $Ar^2$, defines a cyclic system selected from $C(R^1)_2$, $Si(R^1)_2$, C=O, C=$NR^1$, C=$C(R^1)_2$, O, S, S=O, $SO_2$, $N(R^1)$, $P(R^1)$, $P(=O)R^1$, $P(=S)R^1$, $B(R^1)$ or a combination of two, three or four of these groups;

$X^2$ and $X^3$ are on each occurrence, identically or differently, a bridge which, with $Ar^2$ and $Ar^3$, defines a cyclic ring system selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$, $P(=O)R^1$, $P(=S)R^1$ or a combination of two, three or four of these groups;

p=0;

one of the two indices n and o is equal to 1, and the other of the two indices n and o is equal to 0;

q and r are on each occurrence 1 if the corresponding central atom of the group Y or Z is an element from the 5th main group and on each occurrence are equal to 0 if the corresponding central atom of the group Y or Z is an element from the 4th or 6th main group;

s is 1, 2 or 3; and t is on each occurrence, identically or differently, 0 or 1, where t=0 means that $R^1$ radicals are bonded instead of the group E; furthermore, t=0 if q=0 and t=0, if r=0.

5. The compound according to claim 1, wherein the symbols $Ar^4$, $Ar^5$, $Ar^6$ and $Ar^7$, identically or differently on each occurrence, stand for an aromatic or heteroaromatic ring system having 5 to 16 aromatic ring atoms, for a triarylamine or for spirobifluorene, each of which is optionally substituted by one or more radicals $R^1$.

6. The compound according to claim 1, wherein the symbol $R^1$, identically or differently on each occurrence, stands for H, F, CN, a straight-chain alkyl group having 1 to 5 C atoms or a branched alkyl group having 3 to 5 C atoms, where in each case one or more non-adjacent $CH_2$ groups is optionally replaced by —$R^2$C=$CR^2$—, —C≡C—, —O— or —S— and where one or more H atoms is optionally replaced by F, or a monovalent aryl or heteroaryl group having 2 to 16 C atoms, which is optionally substituted by one or more radicals $R^2$; two or more radicals $R^1$ optionally form a ring system with one another.

7. The compound according to claim 1, wherein the index p=0 and one of the two indices n and o =1, while the other of the two indices=0, having the structures of the formulae (1b) and (1c)

Formula (1b)

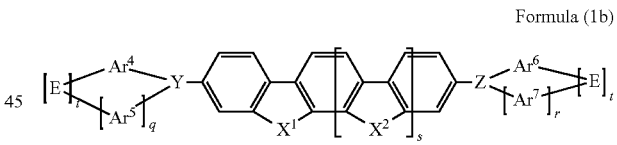

Formula (1c)

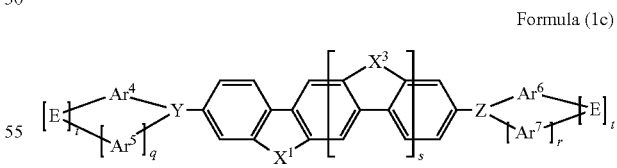

where the symbols and indices have the same meaning as described in claim 1.

8. The compound according to claim 1, wherein the symbols $X^1$, $X^2$, $X^3$ and $X^4$ on each occurrence, identically or differently, represent a bridge which, with $Ar^1$ and $Ar^2$ or with $Ar^2$ and $Ar^3$, defines a cyclic system selected from $C(R^1)_2$, C=O, C=$NR^1$, O, S, S=O $SO_2$, $N(R^1)$, $P(R^1)$, $P(=O)R^1$, $C(R^1)_2$—$C(R^1)_2$, $C(R^1)_2$—$C(R^1)_2$—$C(R^1)_2$, $C(R^1)_2$—O and $C(R^1)_2$—O—$C(R^1)_2$.

9. The compound according to claim 1, wherein the compound of formula (1) is a compound of the formula (1d)

Formel (1d)

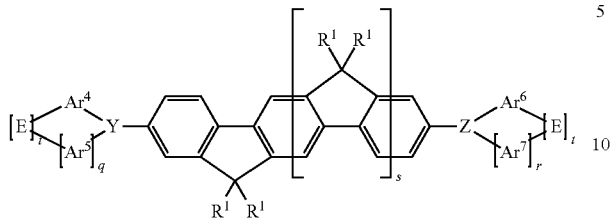

where the symbols and indices have the same meanings as described in claim 1.

10. The compound according to claim 9, wherein the radicals $R^1$ form a ring system with one another.

11. The compound according to claim 1, wherein Y=Z.

12. Organic electronic devices comprising at least one compound according to claim 1.

13. The organic electronic device according to claim 12, wherein the device is selected from the group consisting of organic electroluminescent device (OLED), organic field-effect transistor (O-FET), organic thin-film transistor (O-TFT), organic light-emitting transistor (O-LET), organic integrated circuit (O-IC), organic solar cell (O-SC), organic field-quench device (O-FQD), light-emitting electrochemical cell (LEC), organic photoreceptor and organic laser diode (O-laser).

14. An organic electroluminescent device comprising anode, cathode and at least one emitting layer, wherein the emitting layer comprises at least one compound according to claim 1.

15. The organic electroluminescent device according to claim 14, wherein the emitting layer comprises at least the compound and a host material and wherein the compound is used as emitter, and the host material in the emitting layer is selected from the classes of oligoarylenes, oligoarylenes containing fused aromatic groups, oligoarylenevinylenes, polypodal metal complexes, hole-conducting compounds, electron-conducting compounds, ketones, phosphine oxides, sulfoxides or atropisomers.

16. The organic electroluminescent device according to claim 14, wherein further layers selected from hole-injection layer, hole-transport layer, hole-blocking layer, electron-transport layer and/or electron-injection layer are present.

17. An organic electronic device which comprises the compound according to claim 1 is employed as hole-transport material in a hole-transport layer and/or in a hole-injection layer, and that the compound in these layers may optionally be doped by electron-acceptor compounds.

18. An organic electronic device which comprises the compound according to claim 1 is employed as electron-transport material in an electron-transport layer and/or as hole-blocking material in a hole-blocking layer and/or as triplet matrix material in an emitting layer.

19. A compound selected from structures (1) to (104)

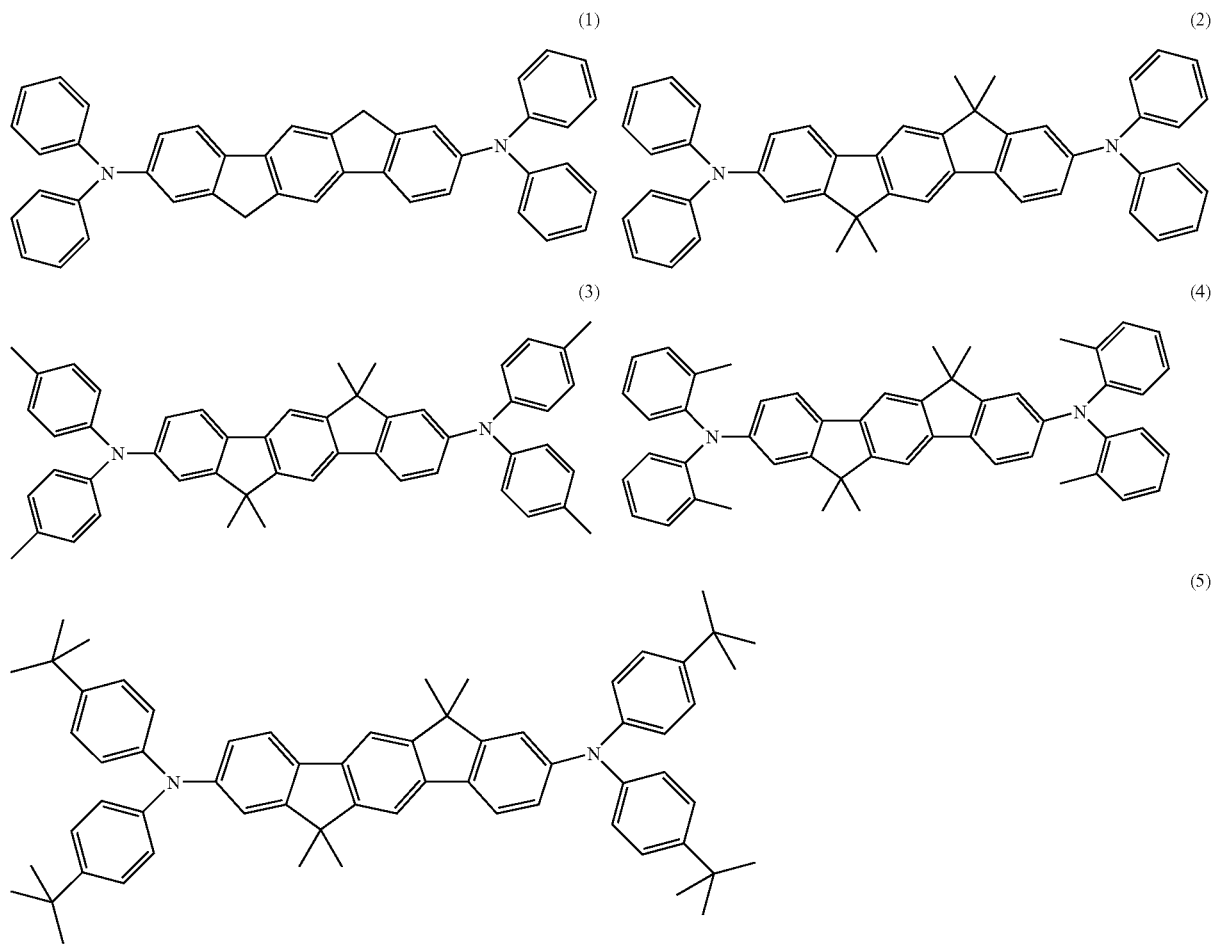

-continued
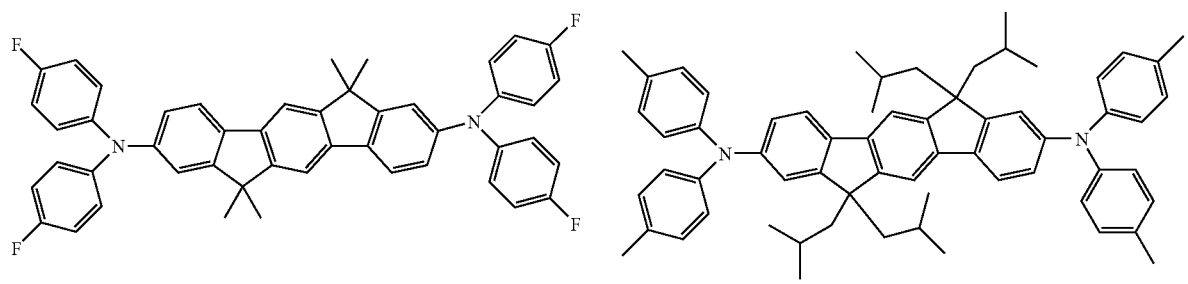
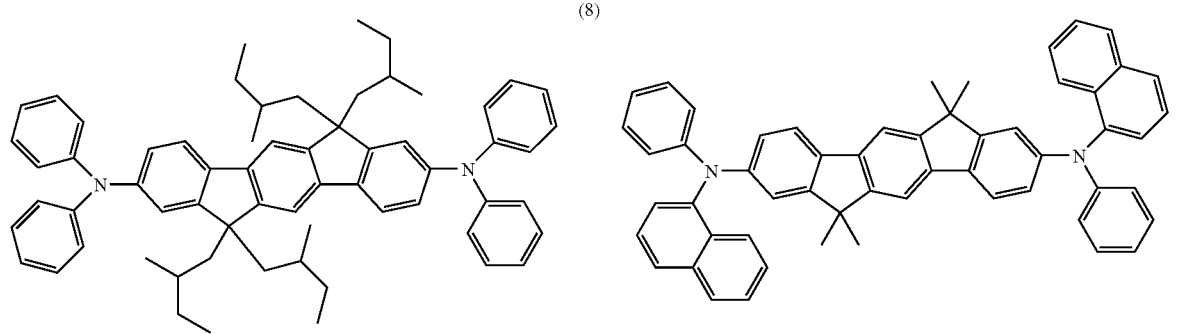
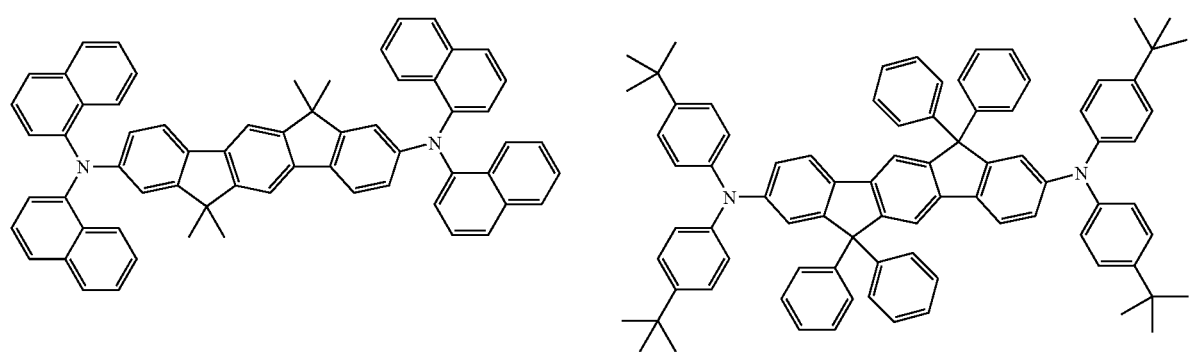
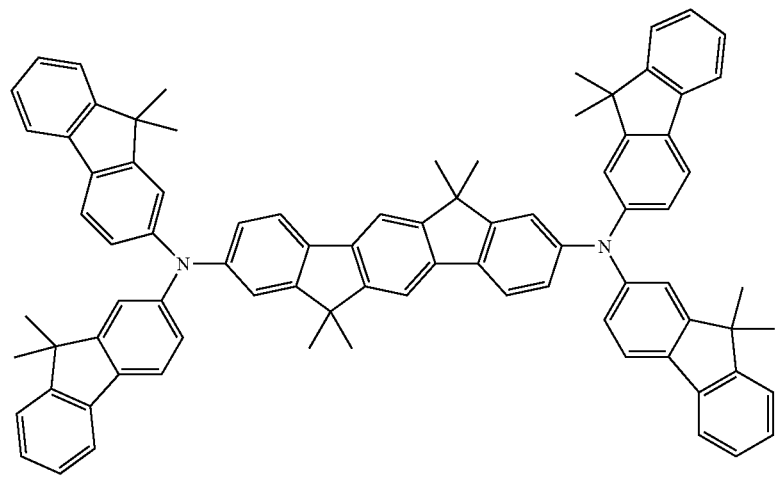

-continued
(13)
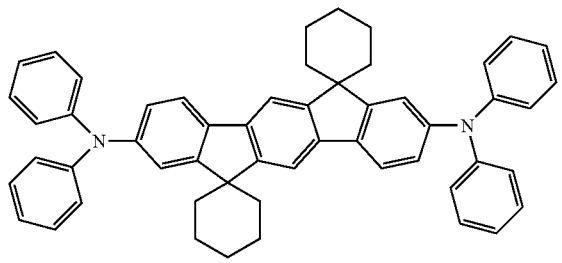
(14)
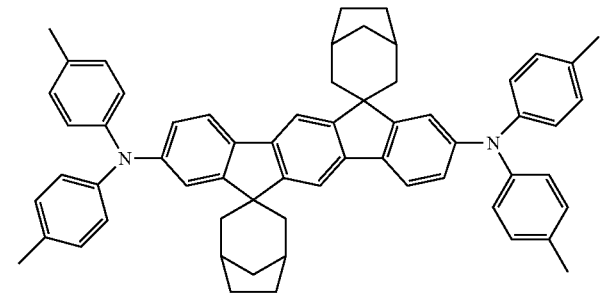
(15)
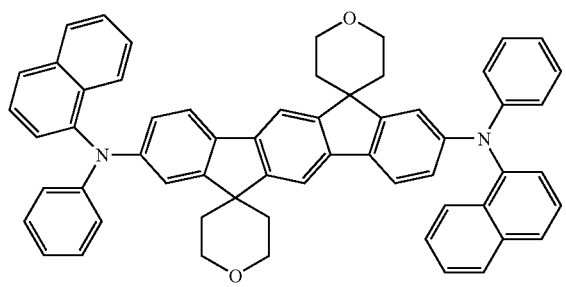
(16)
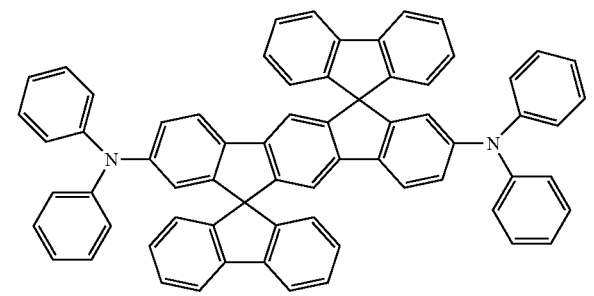
(17)
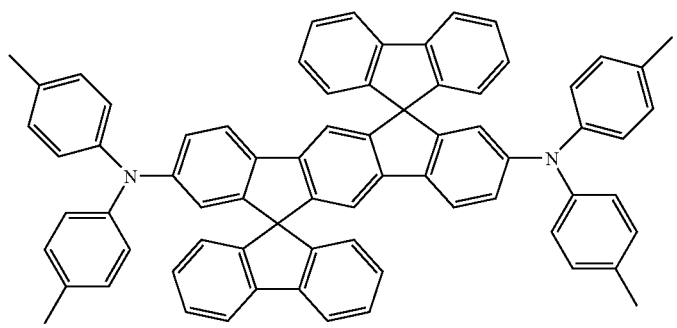
(18)
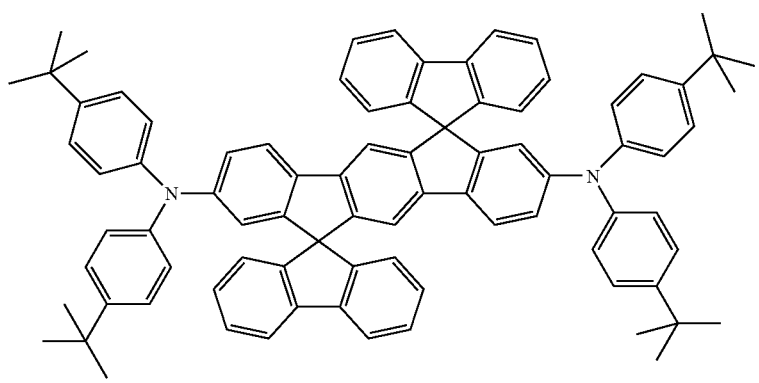
(19)
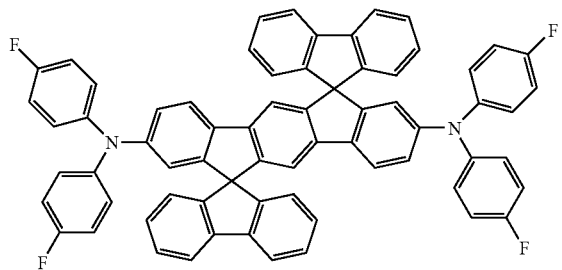
(20)
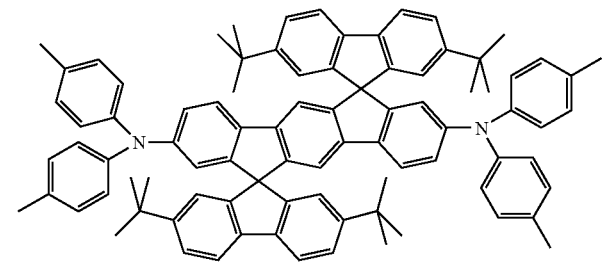

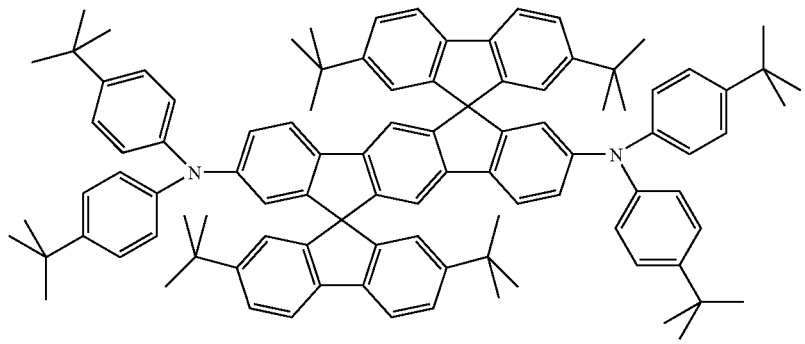
(21)
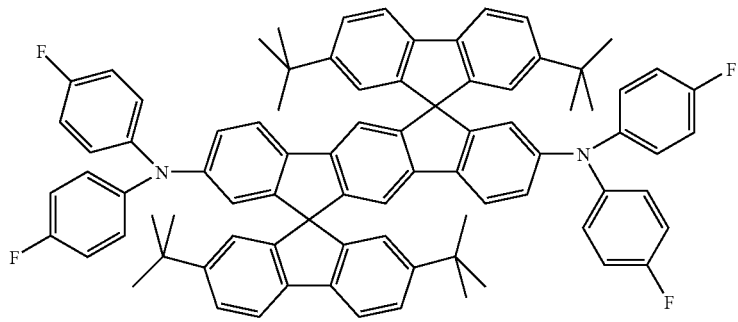
(22)
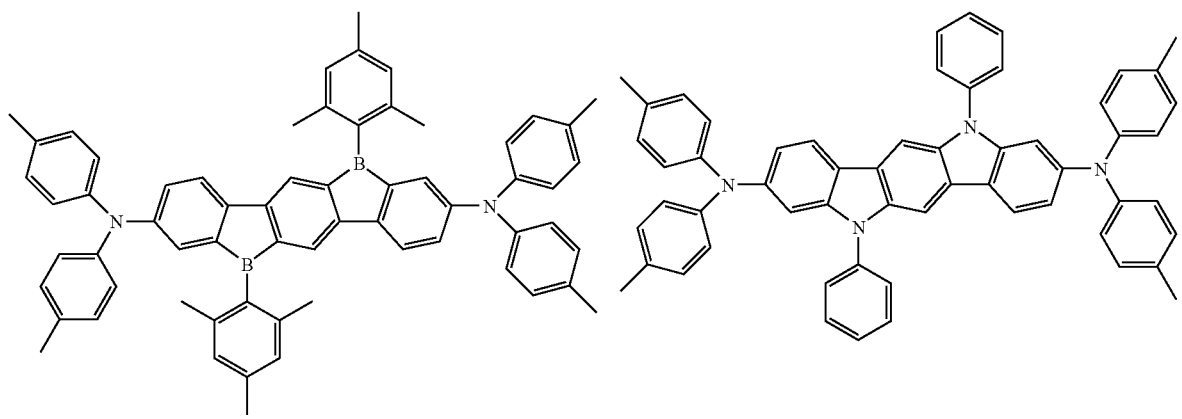
(23) (24)
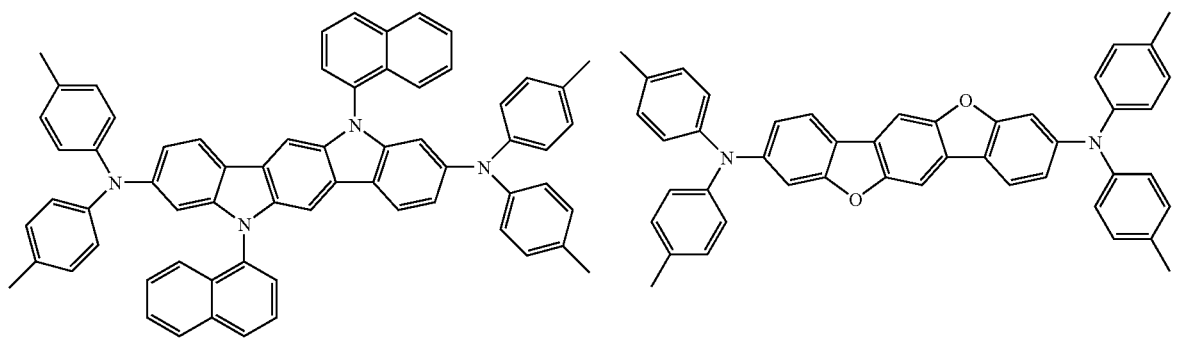
(25) (26)

-continued
(27)
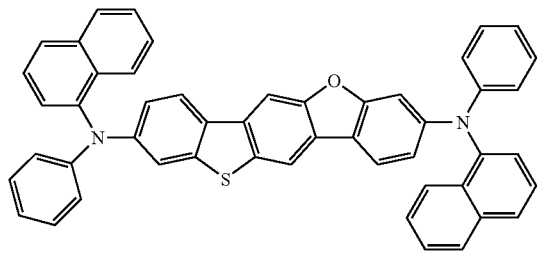
(28)
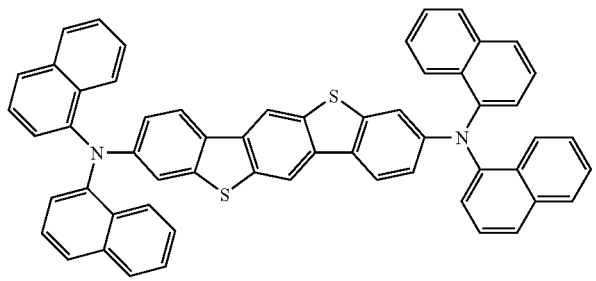
(29)
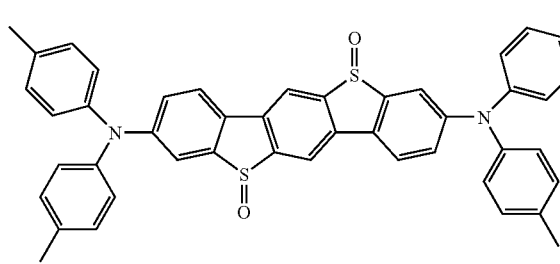
(30)
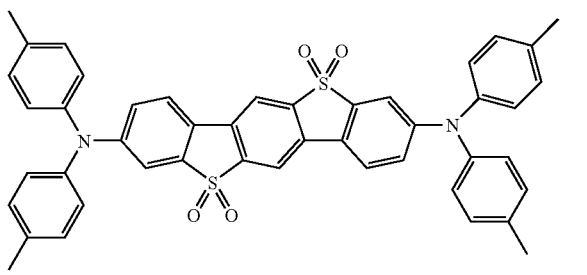
(31)
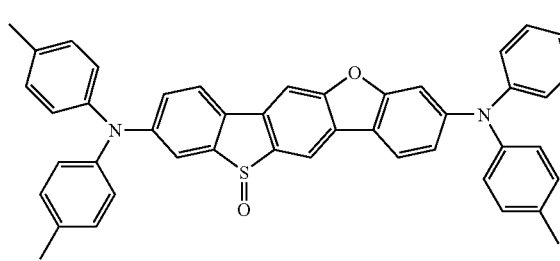
(32)
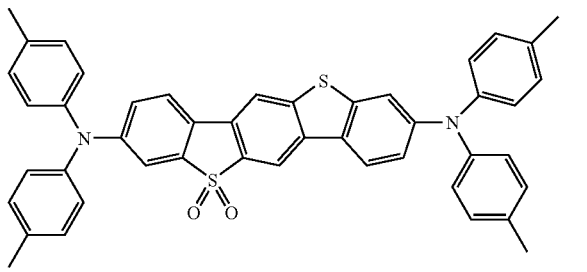
(33)
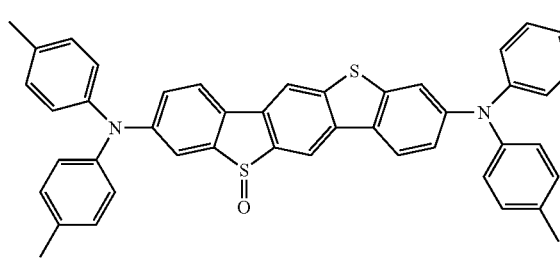
(34)
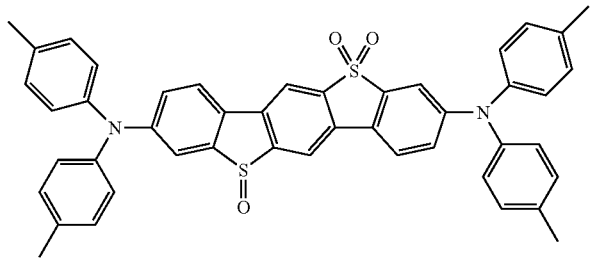
(35)
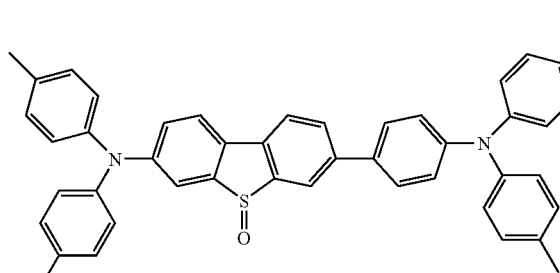
(36)
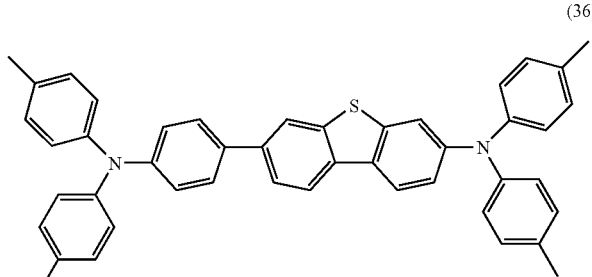

-continued
(37)
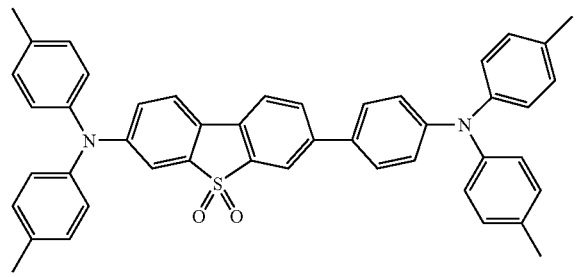
(38)
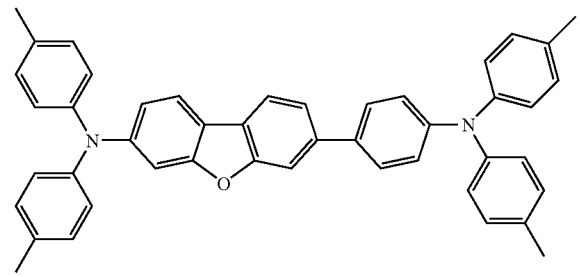
(39)
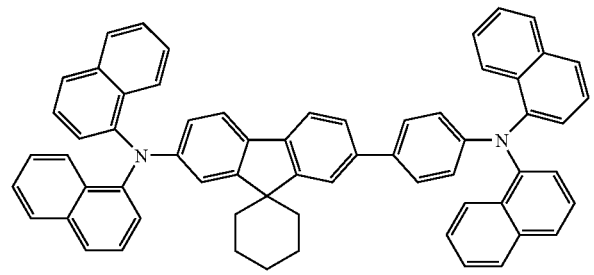
(40)
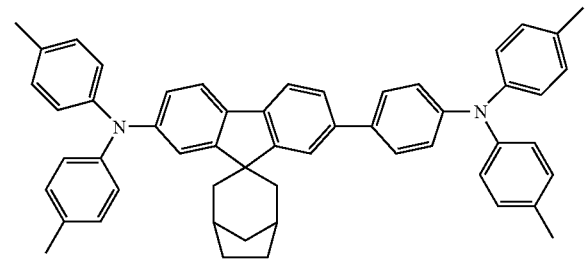
(41)
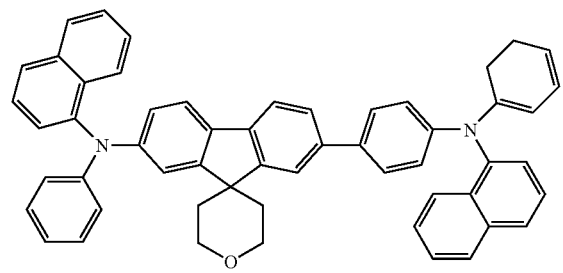
(42)
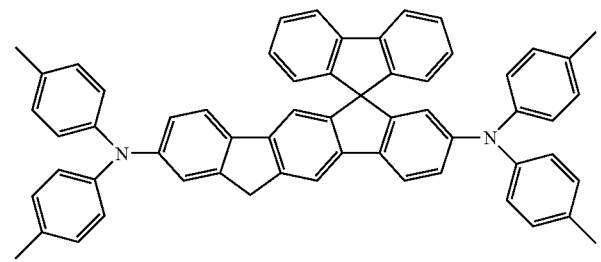
(43)
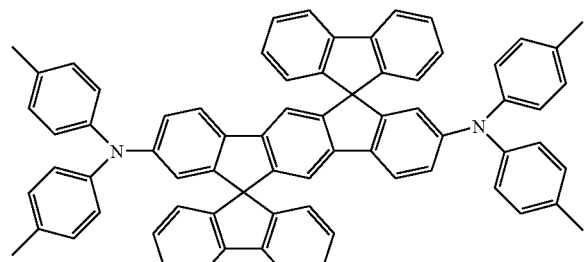
(44)
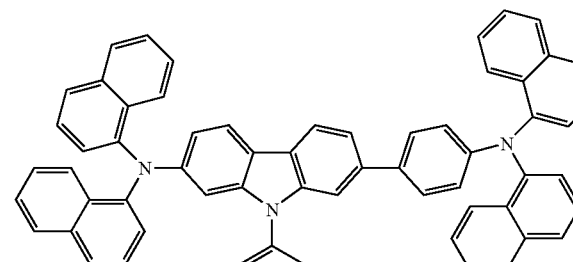
(45)
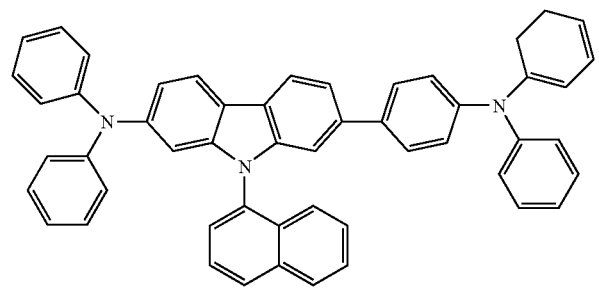
(46)
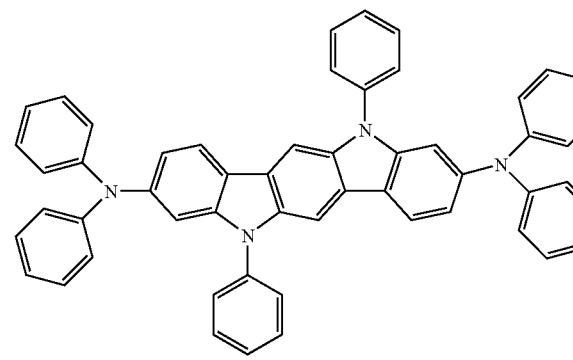

-continued
(47) (48)
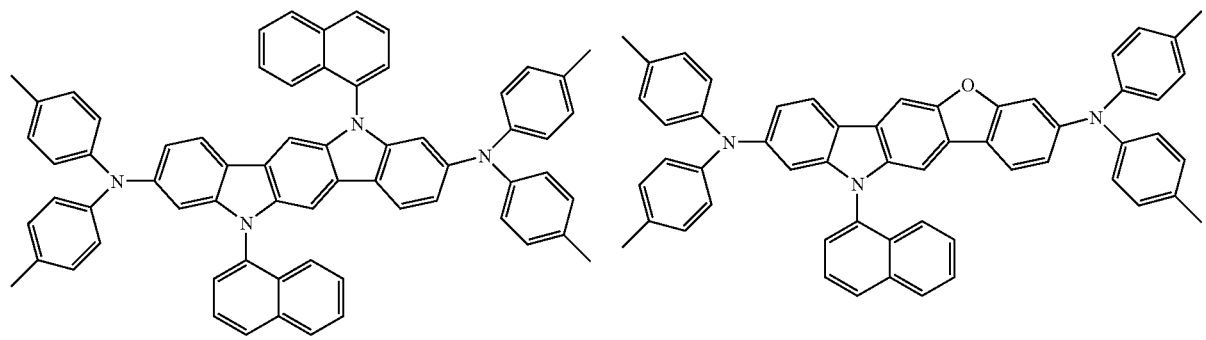
(49) (50)
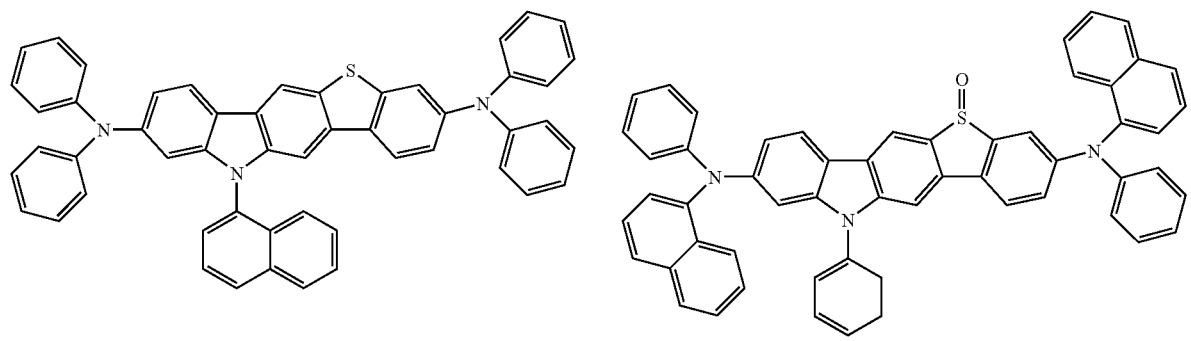
(51) (52)
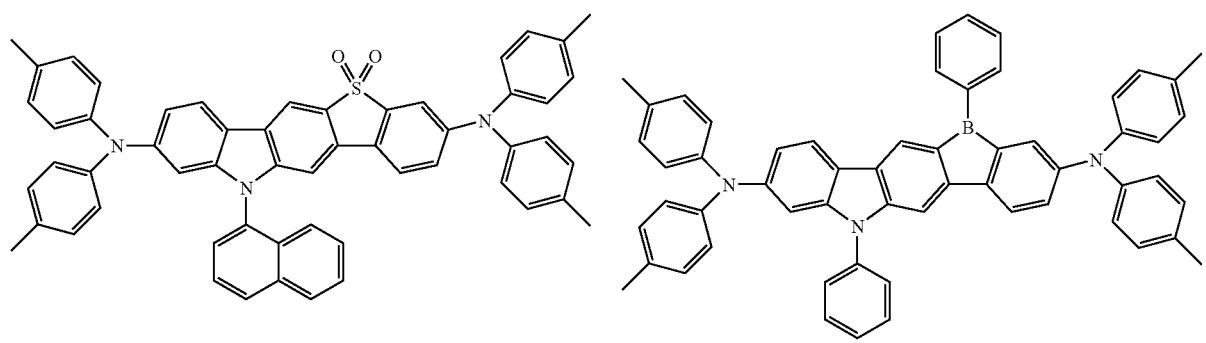
(53) (54)
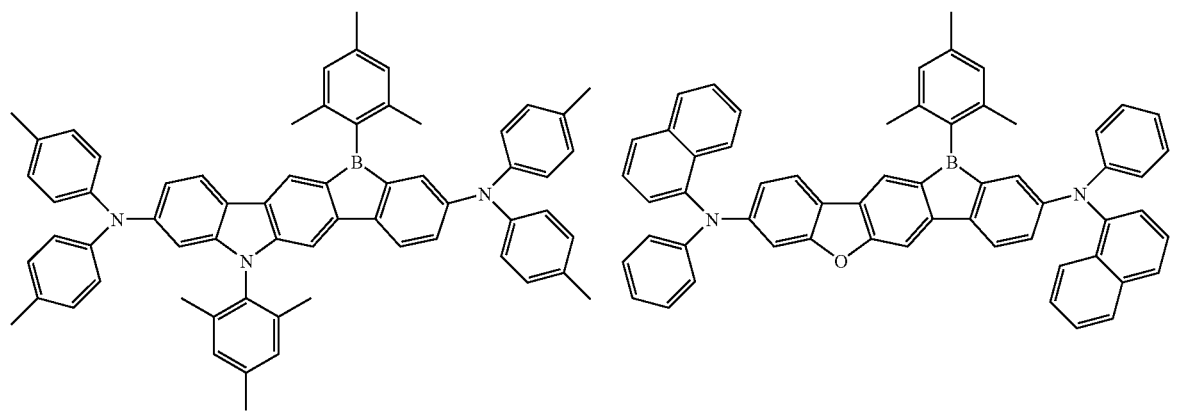

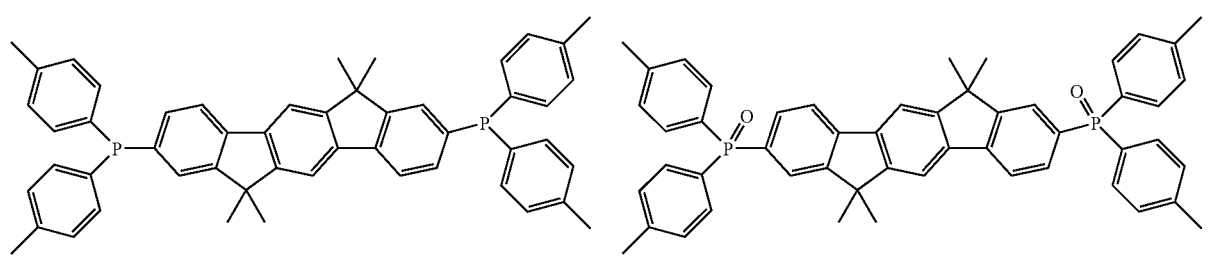
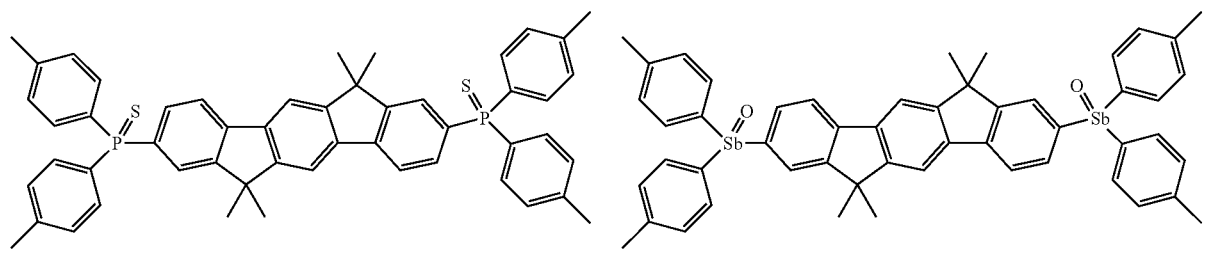
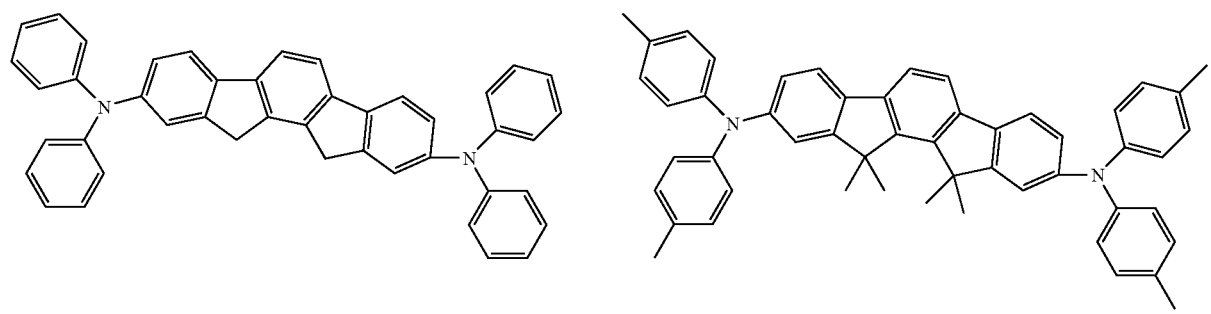
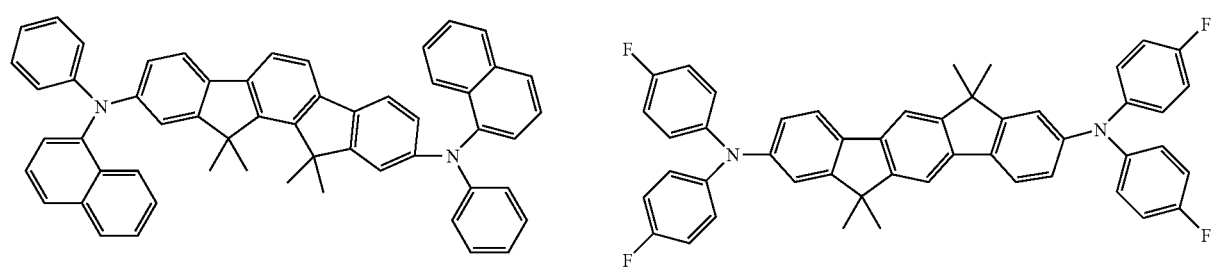

-continued
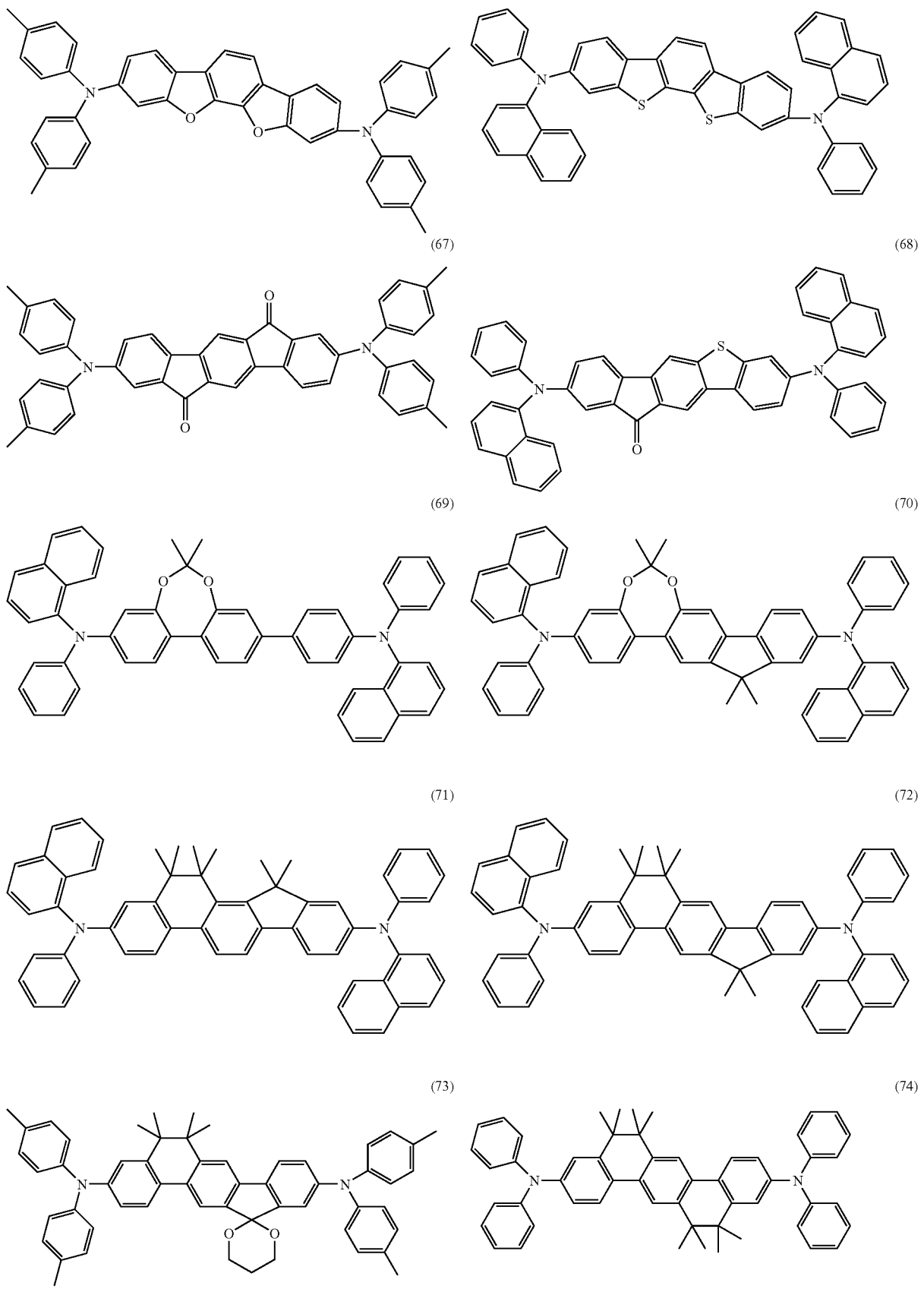

-continued
(75)
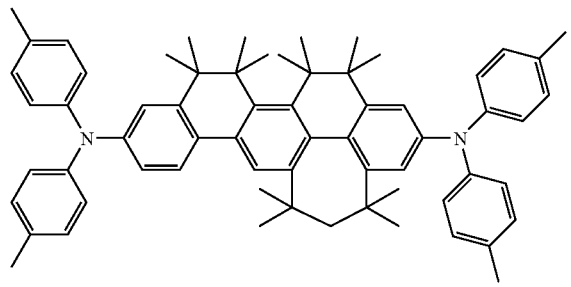
(76)
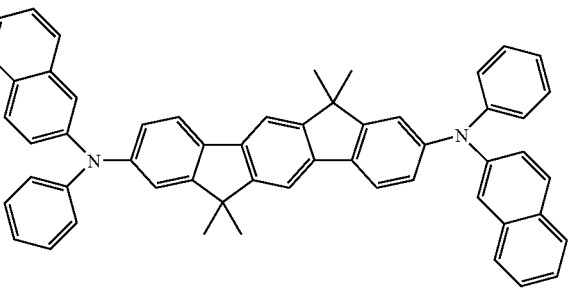
(77)
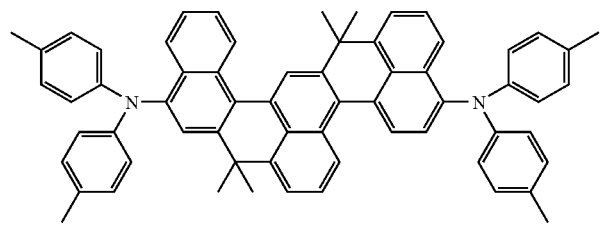
(78)
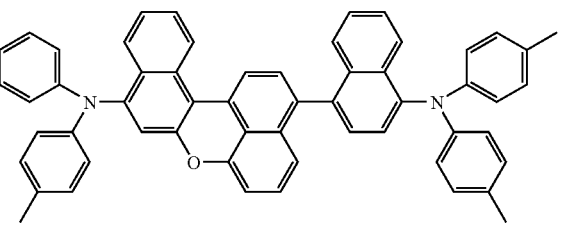
(79)
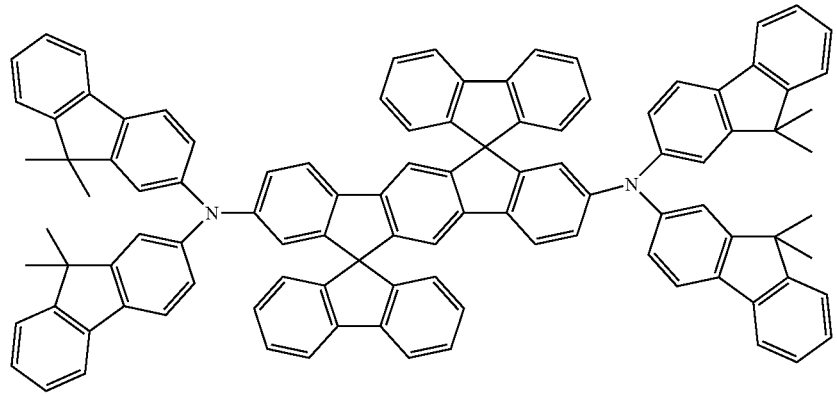
(80)
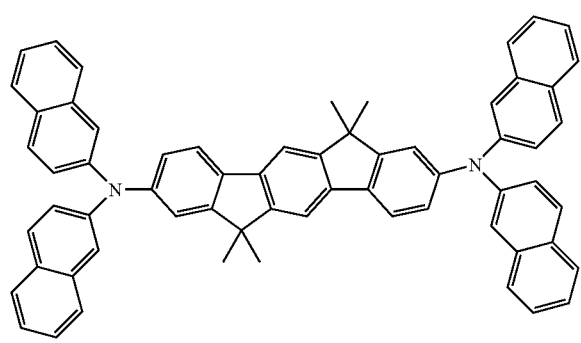
(81)
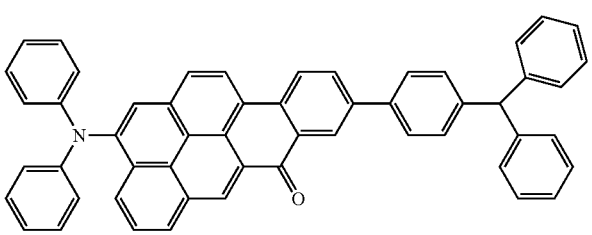
(82)
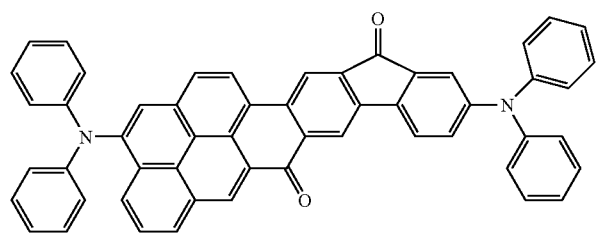
(83)
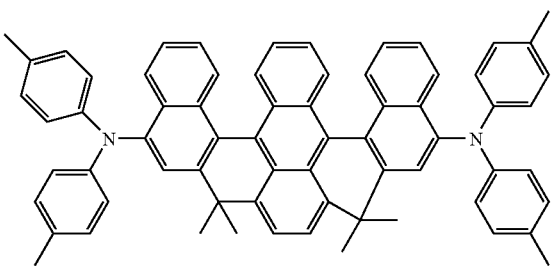

-continued
(84)
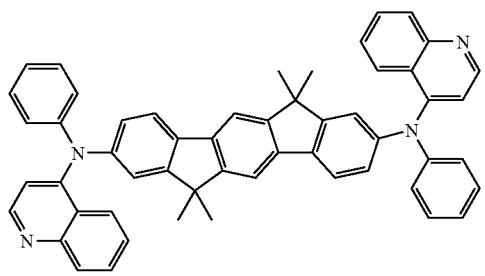
(85)
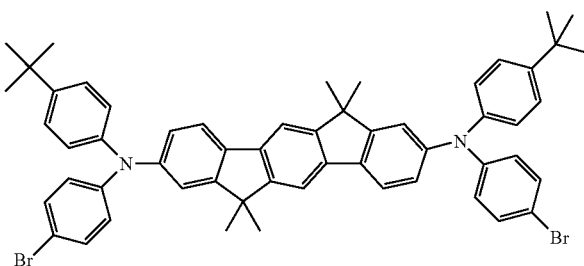
(86)
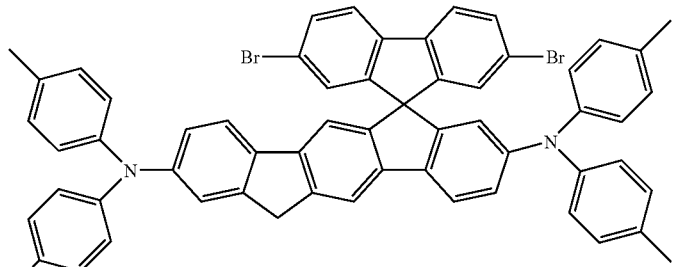
(87)
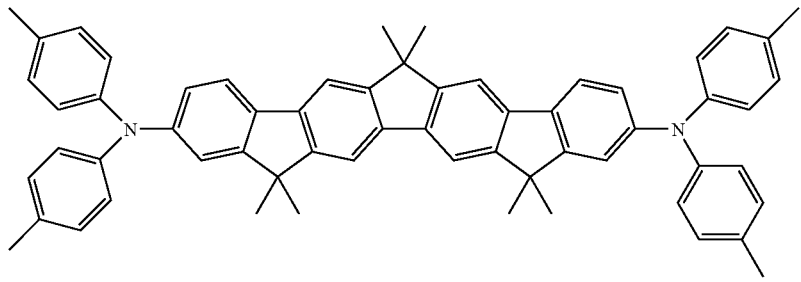
(88)
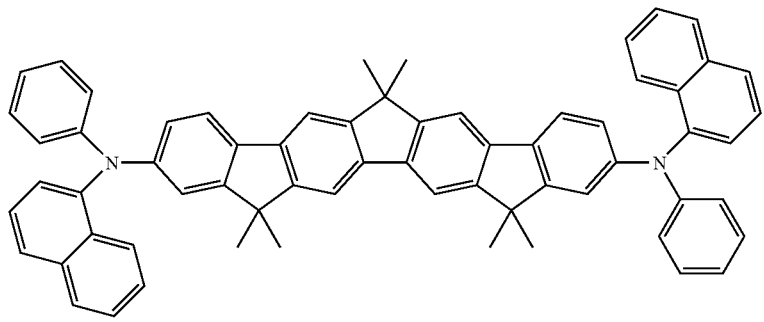
(89)
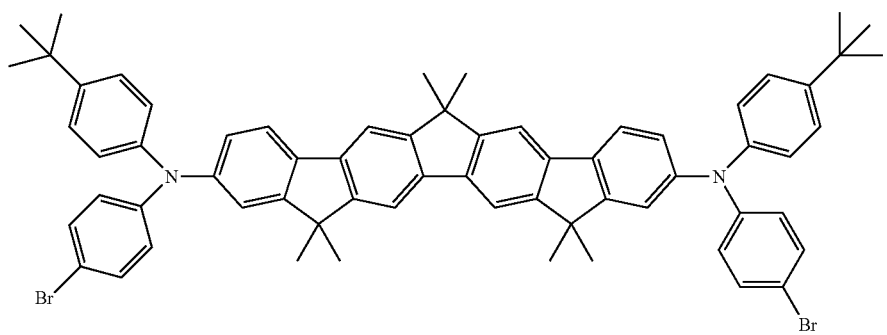

-continued
(90)
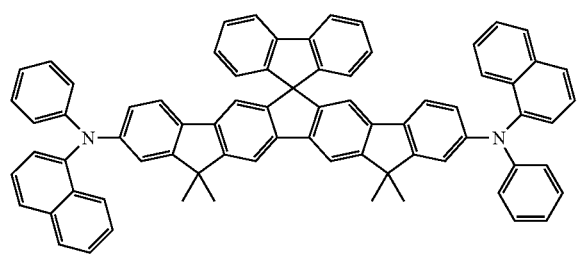
(91)
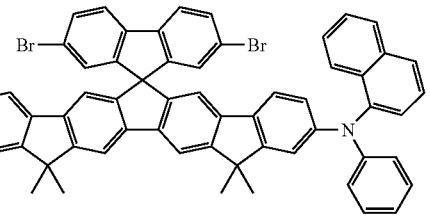
(92)
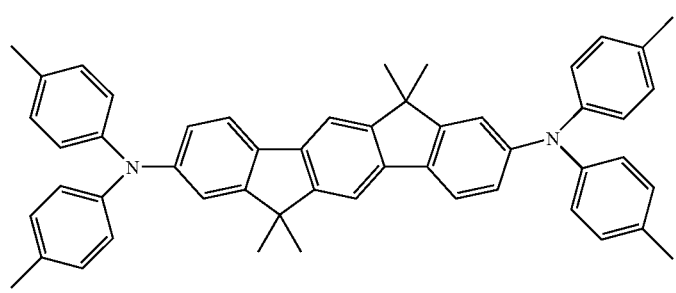
(93)
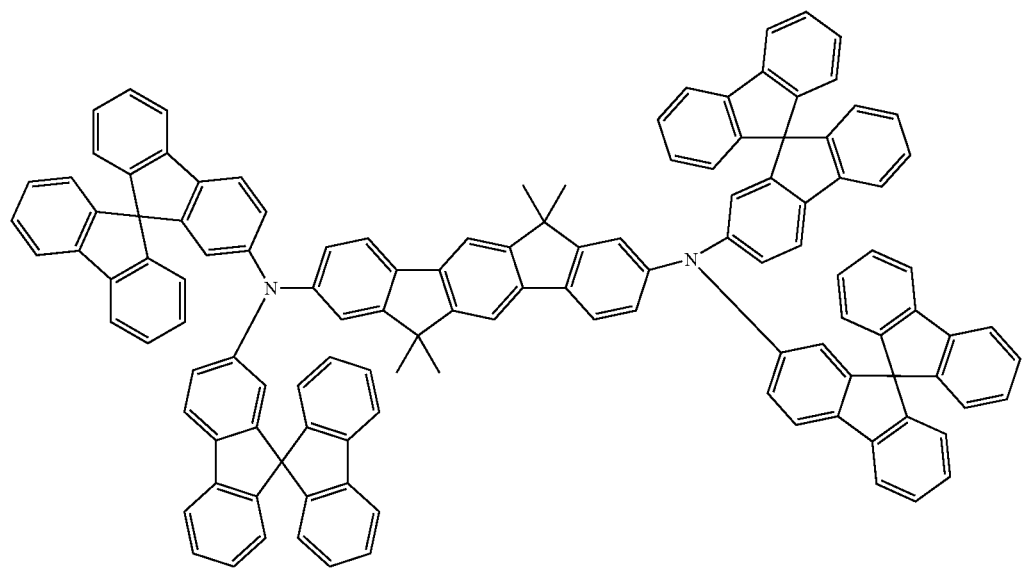

(94)
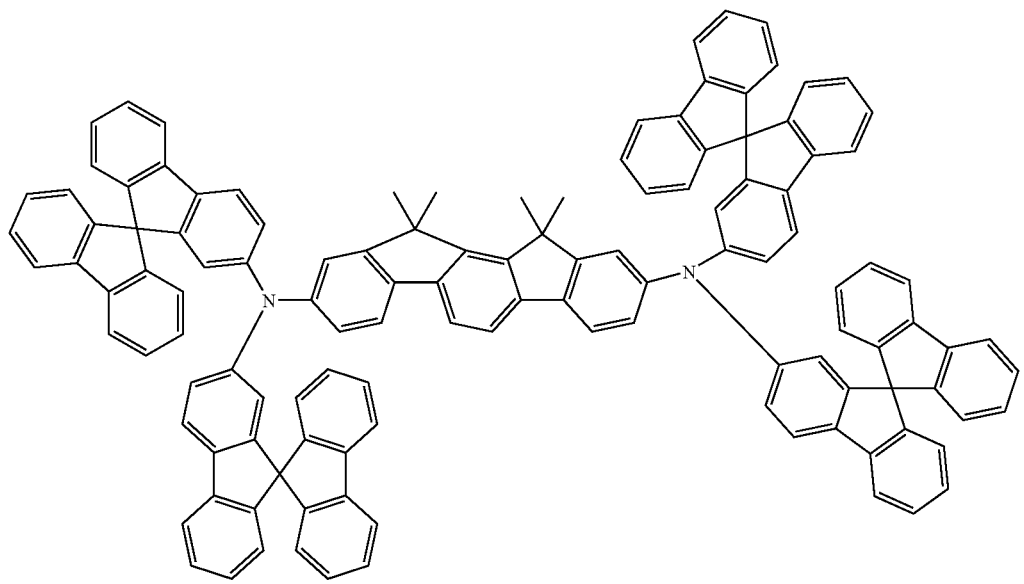
(95)
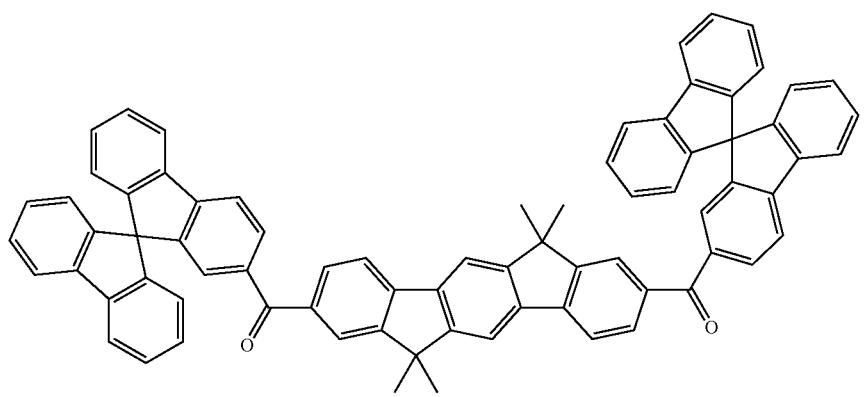
(96)
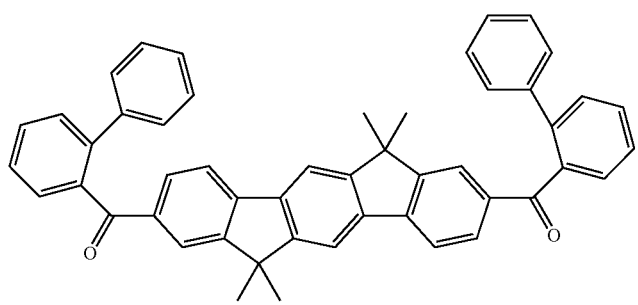

-continued
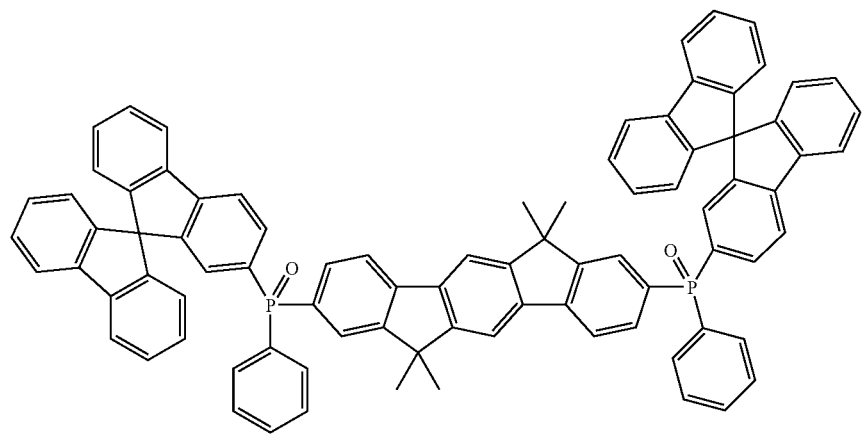
(97)
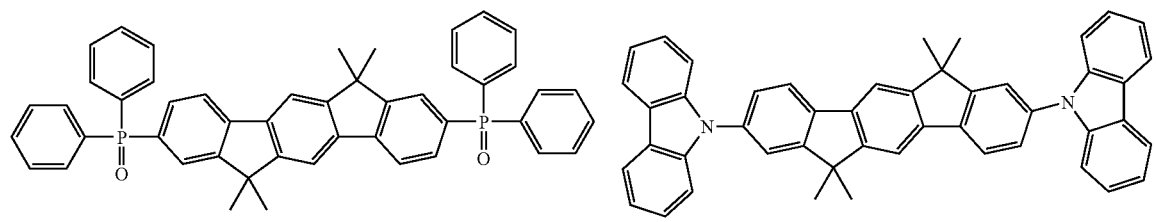
(98) (99)
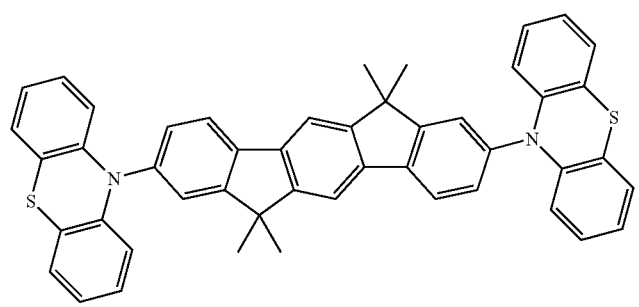
(100)
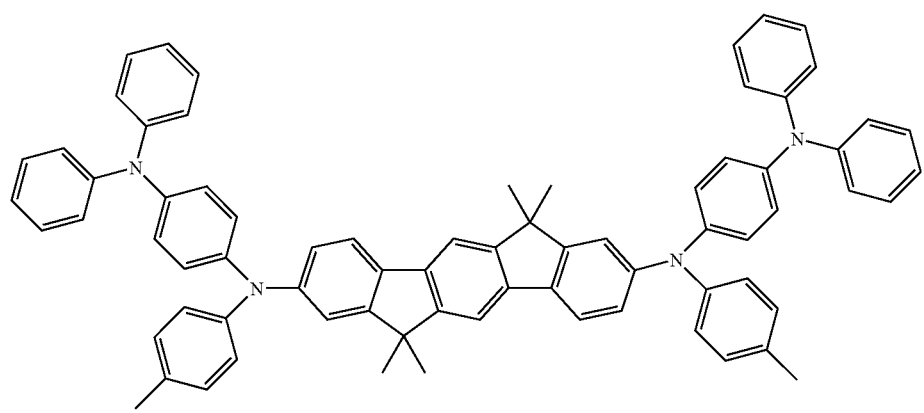
(101)

-continued
(102)
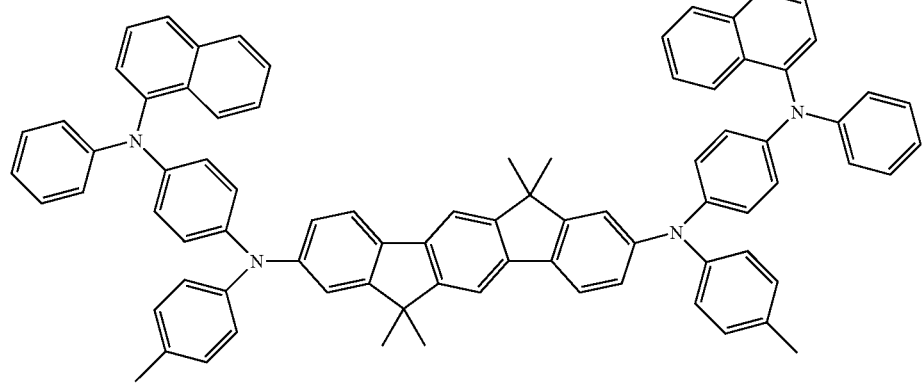
(103)
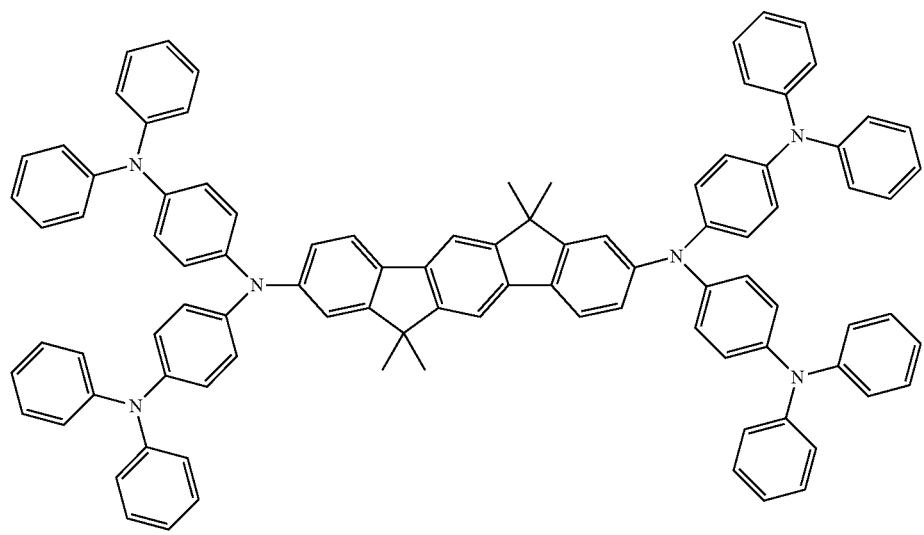
(104)
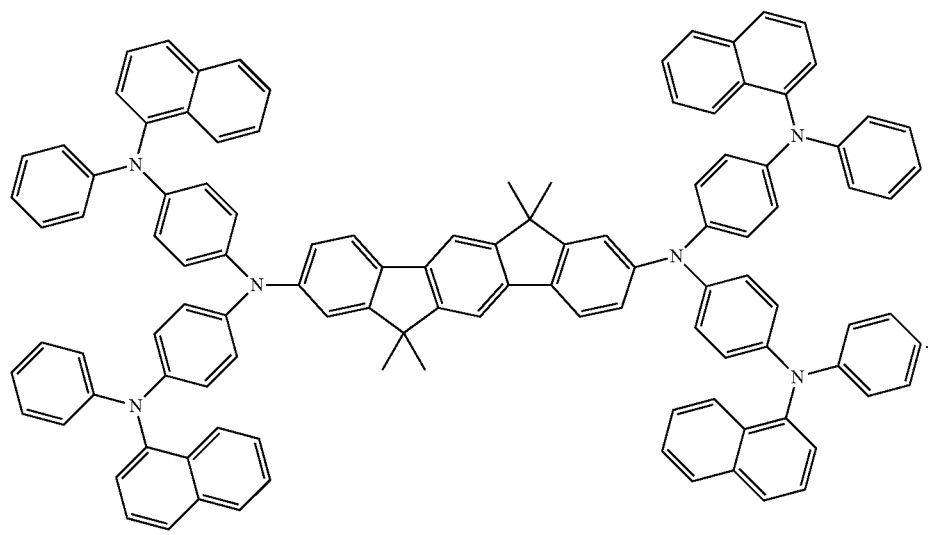

20. A conjugated, partially conjugated or non-conjugated polymer, oligomer or dendrimer comprising one or more compounds of the formula (1b)

Formula (1b)

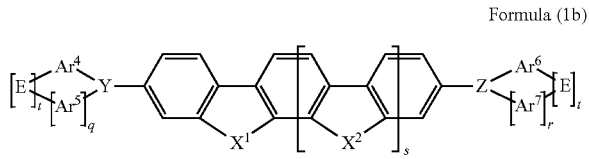

wherein

Y and Z are, identically or differently, N, P, P=O, $PF_2$, P=S, As, As=O, As=S, Sb, Sb=O, Sb=S, C=O, O, S, Se, Te, S=O, $SO_2$, Se=O, $SeO_2$, Te=O or $TeO_2$;

$Ar^4$, $Ar^5$, $Ar^6$ and $Ar^7$ are on each occurrence, identically or differently, an aromatic or heteroaromatic ring system having 5 to 40 aromatic ring atoms, which are optionally substituted by one or more radicals $R^1$;

E is on each occurrence, identically or differently, a single bond, $N(R^1)$, O, S, $C(R^1)_2$, $Si(R^1)_2$ or $B(R^1)$;

$R^1$ is on each occurrence, identically or differently, H, F, Cl, Br, I, CN, $NO_2$, $Si(R^2)_3$, $B(OR^2)_2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by —$R^2$C=$CR^2$—, —C≡C—, $Si(R^2)_2$, $Ge(R^2)_2$, $Sn(R^2)_2$, C=O, C=S, C=Se, C=$NR^2$, —O—, —S—, —COO— or —$CONR^2$— and where one or more H atoms is optionally replaced by F, Cl, Br, I, CN or $NO_2$, or an aromatic or heteroaromatic ring system having 5 to 40 aromatic ring atoms, which is optionally substituted by one or more non-aromatic radicals $R^1$, or an aryloxy or heteroaryloxy group having 5 to 40 aromatic ring atoms, which is optionally substituted by one or more non-aromatic radicals $R^1$, or a combination of these systems; two or more substituents $R^1$ optionally form a mono- or polycyclic ring system with one another;

$R^2$ is on each occurrence, identically or differently, H or an aliphatic or aromatic hydrocarbon radical having 1 to 20 C atoms;

$X^1$ are on each occurrence, identically or differently, a bridge which, with $Ar^1$ and $Ar^2$, defines a cyclic system selected from $C(R^1)_2$, $Si(R^1)_2$, C=O, C=$NR^1$, C=C$(R^1)_2$, O, S, S=O, $SO_2$, $N(R^1)$, $P(R^1)$, P(=O)$R^1$, P(=S)$R^1$, $B(R^1)$ or a combination of two, three or four of these groups;

$X^2$ are on each occurrence, identically or differently, a bridge which, with $Ar^2$ and $Ar^3$, defines a cyclic ring system selected from $B(R^1)$, $C(R^1)_2$, $Si(R^1)_2$, C=O, C=$NR^1$, C=C$(R^1)_2$, O, S, S=O,$SO_2$, $N(R^1)$, $P(R^1)$, P(=O)$R^1$, P(=S)$R^1$ or a combination of two, three or four of these groups;

q and r are on each occurrence 1 if the corresponding central atom of the group Y or Z is an element from the $5^{th}$ main group and on each occurrence are equal to 0 if the corresponding central atom of the group Y or Z is an element from the $4^{th}$ or $6^{th}$ main group;

s is 1, 2 or 3; and t is on each occurrence, identically or differently, 0 or 1, where t=0 means that $R^1$ radicals are bonded instead of the group E; furthermore, t=0 if q=0 and t=0, if r=0, wherein one or more radicals $R^1$ in the compound of the formula (1b) represent a bond to the polymer, oligomer or dendrimer.

21. The polymer, oligomer or dendrimer according to claim 20, wherein the polymer comprises recurring units selected from the group consisting of fluorenes, spirobifluorenes, para-phenylenes, carbazoles, thiophenes, dihydrophenanthrenes, indenofluorenes, phenanthrenes, aromatic ketones, metal complexes, triarylamines or a plurality of these units.

* * * * *